US010017787B2

(12) United States Patent
Anissimova et al.

(10) Patent No.: US 10,017,787 B2
(45) Date of Patent: Jul. 10, 2018

(54) PRODUCTION OF ALKENES FROM 3-HYDROXYCARBOXYLIC ACIDS VIA 3-HYDROXYCARBOXYL-NUCLEOTIDYLIC ACIDS

(71) Applicants: Global Bioenergies, Evry (FR); Scientist of Fortune S.A., Luxembourg (LU)

(72) Inventors: Maria Anissimova, Nozay (FR); Mathieu Allard, Saint Vrain (FR); Philippe Marliere, Tournai (BE)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 15/101,148

(22) PCT Filed: Dec. 2, 2014

(86) PCT No.: PCT/EP2014/076203
§ 371 (c)(1),
(2) Date: Jun. 2, 2016

(87) PCT Pub. No.: WO2015/082447
PCT Pub. Date: Jun. 11, 2015

(65) Prior Publication Data
US 2016/0298139 A1    Oct. 13, 2016

(30) Foreign Application Priority Data

Dec. 3, 2013 (EP) ..................................... 13195569

(51) Int. Cl.
| | |
|---|---|
| *C12P 5/02* | (2006.01) |
| *C12P 5/00* | (2006.01) |
| *C12P 7/42* | (2006.01) |
| *C12N 9/02* | (2006.01) |
| *C12N 9/90* | (2006.01) |
| *C12N 9/88* | (2006.01) |

(52) U.S. Cl.
CPC ............ *C12P 5/026* (2013.01); *C12N 9/0008* (2013.01); *C12P 5/007* (2013.01); *C12Y 102/99006* (2013.01)

(58) Field of Classification Search
CPC .... C12N 9/93; C12P 7/18; C12P 5/026; C12P 7/04; C12Y 401/01033
USPC .... 435/167, 146, 157, 194; 3/167, 146, 157, 3/194
See application file for complete search history.

(56) References Cited

FOREIGN PATENT DOCUMENTS

| WO | 2010001078 A2 | 1/2010 |
|---|---|---|
| WO | 2010001078 A3 | 1/2010 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
International Search Report and Written Opinion from corresponding PCT/EP2014/076203, dated Apr. 24, 2015.
European Search Report from corresponding EP 13195569.2, dated May 30, 2014.
Heidelberg et al., "Genome sequence of the dissimilatory metal ion-reducing bacterium Shewanella oneidesis", Nature Biotechnology, vol. 20., No. 11, Oct. 1, 2002, pp. 1118-1123, XP008128172, Nature Publishing Group, New York, NY.
Database Nucleotide, Jan. 31, 2014, "Shewanella oneidensis MR-1, complete genome", XP002724002, Database Accession No. AE014299.
Ladygina et al., "A review on microbial synthesis of hydrocarbons", Elsevier Ltd., Process Biochemistry, vol. 41, No. 5, May 1, 2006, Pushchino, Moscow Region,Russia, pp. 1001-1014, XP027984109.
Van Leeuwen et al., "Fermentative production of isobutene", Applied Microbiology and Biotechnology, vol. 93, No. 4, Jan. 11, 2012, pp. 1377-1387, Springer, Berlin, DE, XP035013024.
Fischer et al., "Production of C3 Hydrocarbons from Biomass via Hydrothermal Carboxylate Reforming", Industrial & Engineering Chemistry Research, vol. 50, No. 8, Apr. 20, 2011, pp. 4420-4424, Cambridge, Massachusetts, XP55116355.
Rude et al, "Terminal Olefin (1-Alkene) Biosynthesis by a Novel P450 Fatty Acid Decarboxylase from *Jeotgalicoccus* Species", Applied and Environmental Microbiology, vol . 77, No. 5, Mar. 1, 2011, pp. 1718-1727, South San Francisco, California, XP055107215.
Schmelz et al., "Adenylate-forming enzymes", Current Opinion in Structural Biology, vol. 19, No. 6, Dec. 1, 2009, pp. 666-671, Elsevier Ltd, GB, XP026801487.
Frias et al., "Purification and Characterization of OleA from Xanthomonas campestris and Demonstration of a Non-decarboxylative Claisen Condensation Reaction", The Journal of Biological Chemistry, vol. 286, No. 13, Jan. 25, 2011, pp. 10930-10938, XP055116336.
Sukovich et al., "Widespread Head-to-Head Hydrocarbon Biosynthesis in Bacteria and Role of OleA", Applied and Environmental Microbiology, vol. 76, No. 12, Apr. 23, 2010, pp. 3850-3862, XP055116387.
Sukovich et al., "Structure, Function, and Insights into the Biosynthesis of a Head-to-Head Hydrocarbon in Shewanella oneidensis Strain MR-1", Applied and Environmental Microbiology, vol. 76, No. 12, Apr. 23, 2010, pp. 3842-3849, XP055116385.

\* cited by examiner

*Primary Examiner* — Tekchand Saidha
*Assistant Examiner* — Mohammad Y Meah
(74) *Attorney, Agent, or Firm* — Michele M. Wales; Inhouse Patent Counsel, LLC

(57) ABSTRACT

The application describes a method for producing alkenes (for example propylene, ethylene, 1-butylene, isobutylene, isoamylene, butadiene or isoprene) from 3-hydroxycarboxylic acids via 3-hydroxycarboxyl-nucleotidylic acids.

15 Claims, 35 Drawing Sheets

Figure 1:
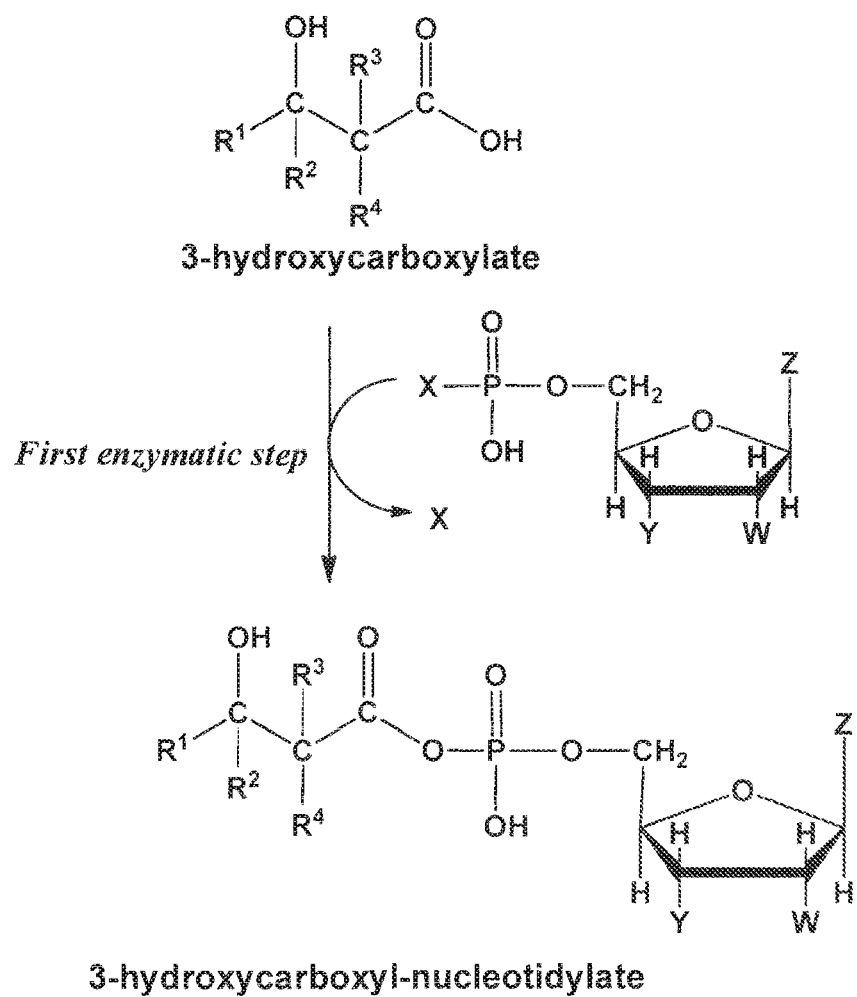

SEQUENCE LISTING

```
<160> NUMBER OF SEQ ID NOS: 12

<210> SEQ ID NO 1
<211> LENGTH: 542
<212> TYPE: PRT
<213> ORGANISM: Marinobacter aquaeolei

<400> SEQUENCE: 1

Met Thr Ser Ile Phe Asp Gln Gly Leu Glu Pro Arg Asp Ala Asn Tyr
1               5                   10                  15

Ala Val Gln Ser Pro Ile Asp Phe Ile Glu Arg Thr Ala Ser Val Tyr
                20                  25                  30

Pro Asp Tyr Pro Ala Ile Ile His Gly Ala Ile Arg Arg Thr Trp Ala
            35                  40                  45

Glu Thr Tyr Asp Arg Cys Leu Arg Leu Ala Ser Ala Leu Lys Gly Arg
        50                  55                  60

Gly Ile Gly Arg Gly Asp Thr Val Ala Val Met Leu Pro Asn Ile Pro
65                  70                  75                  80

Ala Met Val Glu Cys His Phe Gly Ile Pro Met Ile Gly Ala Val Leu
                85                  90                  95

Asn Thr Leu Asn Val Arg Leu Asp Ala Glu Ala Ile Ala Phe Met Leu
            100                 105                 110

Glu His Gly Glu Ala Lys Val Val Ile Ala Asp Arg Glu Phe Gly Gln
        115                 120                 125

Val Ile Lys Asp Ala Val Arg His Leu Glu His Lys Pro Leu Val Ile
    130                 135                 140

Asp Val Asp Pro Glu Tyr Gly Glu Gly Val Gln Val Ser Asp Leu
145                 150                 155                 160

Asp Tyr Glu Ala Phe Leu Gln Gly Gly Asp Pro Gln Phe Gln Trp Ser
                165                 170                 175

Phe Pro Asp Asn Glu Trp Asp Ala Ile Ser Leu Asn Tyr Thr Ser Gly
            180                 185                 190
```

Thr Thr Gly Asn Pro Lys Gly Val Val Tyr His His Arg Gly Ala Tyr
            195                 200                 205

Ile Asn Ala Leu Gly Asn Gln Thr Val Trp Ser Met Asp Met His Pro
    210                 215                 220

Val Tyr Leu Trp Thr Leu Pro Met Phe His Cys Asn Gly Trp Cys Phe
225                 230                 235                 240

Pro Trp Thr Ile Thr Ala Met Ala Gly Thr His Val Cys Leu Arg Arg
            245                 250                 255

Val Asp Pro Glu Lys Ile Leu Gln Leu Ile His Asp His Gln Val Thr
            260                 265                 270

His Met Cys Gly Ala Pro Ile Val Leu Asn Ala Leu Leu Asn Ala Ser
        275                 280                 285

Pro Glu Ala Lys Ala Gly Ile Asp His Glu Val Lys Ser Met Thr Ala
    290                 295                 300

Gly Ala Ala Pro Pro Ala Gln Val Ile Gly Ser Ile Glu Glu Met Gly
305                 310                 315                 320

Ile Lys Val Thr His Val Tyr Gly Leu Thr Glu Val Tyr Gly Pro Val
                325                 330                 335

Thr Val Cys Ala Trp Lys Ser Glu Trp Asp Glu Leu Pro Leu His Asp
            340                 345                 350

Arg Ala Lys Ile Lys Ala Arg Gln Gly Val Arg Tyr His Thr Leu Gly
        355                 360                 365

Gly Thr Met Val Ala Asp Pro Asn Thr Met Gln Pro Val Pro Lys Asp
    370                 375                 380

Gly Lys Thr Ile Gly Glu Ile Phe Leu Arg Gly Asn Thr Val Met Lys
385                 390                 395                 400

Gly Tyr Leu Lys Asn Pro Thr Ala Thr Glu Glu Ala Phe Arg Gly Gly
                405                 410                 415

Trp Phe His Thr Gly Asp Leu Ala Val Trp His Glu Asp Gly Tyr Met
            420                 425                 430

Glu Ile Lys Asp Arg Leu Lys Asp Ile Ile Ser Gly Gly Glu Asn
        435                 440                 445

Ile Ser Thr Ile Glu Val Glu Asp Thr Leu Tyr Arg His Pro Ala Val
    450                 455                 460

Leu Glu Ala Ala Val Val Ala Arg Pro Asp Glu Lys Trp Gly Glu Thr
465                 470                 475                 480

Pro Cys Ala Phe Ile Thr Leu Lys Pro Glu Ala Gly Asp Val Ser Glu
                485                 490                 495

Asp Asp Ile Ile Asn Phe Cys Arg Glu His Leu Ala Arg Phe Lys Val
            500                 505                 510

Pro Lys Thr Val Val Phe Thr Glu Leu Pro Lys Thr Ser Thr Gly Lys
        515                 520                 525

Ile Gln Lys Phe Val Leu Arg Asp Gln Ala Lys Asp Leu Asn
    530                 535                 540

<210> SEQ ID NO 2
<211> LENGTH: 542
<212> TYPE: PRT
<213> ORGANISM: Marinobacter algicola DG893

<400> SEQUENCE: 2

Met Asn Ser Ile Phe Asp Lys Gly Leu Glu Pro Thr Asp Ala Asn Asn
1               5                   10                  15

Ala Thr Leu Thr Pro Leu Asp Phe Leu Ala Arg Thr Ala Ser Val Tyr
            20                  25                  30

```
Pro Glu Tyr Pro Ala Val Ile His Gly Ala Thr Arg Arg Asn Trp Gln
            35                  40                  45

Gln Thr Tyr Glu Arg Cys Arg Leu Ala Ser Ala Leu Ala Asp Arg
 50                  55                  60

Gly Val Gly Lys Gly Asp Thr Val Ala Ala Met Leu Pro Asn Ile Pro
 65                  70                  75                  80

Pro Met Leu Glu Cys His Phe Gly Ile Pro Met Leu Gly Ala Val Leu
                 85                  90                  95

Asn Ala Leu Asn Thr Arg Leu Asp Ala Lys Ala Ile Ala Phe Met Leu
            100                 105                 110

Glu His Gly Glu Ala Lys Val Leu Ile Ala Asp Arg Glu Phe Gly Asp
            115                 120                 125

Val Ile Asn Glu Ala Val Gly Met Leu Asp Asn Pro Pro Gln Val Ile
130                 135                 140

Asp Val Asn Asp Pro Glu Phe Ser Gly Ala Gly Thr Gln Val Ser Asp
145                 150                 155                 160

Leu Asp Tyr Asp Ala Phe Val Ala Ser Gly Asp Pro Ala Phe Asp Trp
                165                 170                 175

Gln Met Pro Ala Asp Glu Trp Asp Ala Ile Ser Leu Cys Tyr Thr Ser
                180                 185                 190

Gly Thr Thr Gly Asn Pro Lys Gly Val Val Tyr His His Arg Gly Ala
            195                 200                 205

Tyr Glu Asn Ala Met Gly Asn Gln Ala Val Trp Ser Met Gly Met His
            210                 215                 220

Pro Val Tyr Leu Trp Thr Leu Pro Met Phe His Cys Asn Gly Trp Cys
225                 230                 235                 240

Phe Pro Trp Thr Ile Thr Ala Phe Ala Gly Thr His Val Cys Leu Arg
                245                 250                 255

Lys Val Glu Pro Glu Lys Ile Leu Gln Leu Ile Ser Glu His Lys Val
                260                 265                 270

Ser His Met Cys Gly Ala Pro Ile Val Leu Asn Thr Leu Leu Gly Ala
            275                 280                 285

Ser Glu Ala Ala Lys Ser Ser Phe Ser His Thr Val Gln Ala Met Thr
            290                 295                 300

Ala Gly Ala Ala Pro Pro Ala Lys Val Ile Glu Ala Ile Glu Asn Met
305                 310                 315                 320

Gly Phe Arg Val Thr His Val Tyr Gly Leu Thr Glu Val Tyr Gly Pro
                325                 330                 335

Val Thr Val Cys Ala Trp Lys Ser Glu Trp Asp Asp Leu Pro Val Glu
                340                 345                 350

Asp Arg Ala Arg Ile Lys Ala Arg Gln Gly Val Arg Tyr His Thr Leu
            355                 360                 365

Ala Gly Met Met Val Gly Asp Pro Glu Thr Met Glu Ala Val Pro Lys
            370                 375                 380

Asp Gly Asn Thr Ile Gly Glu Ile Phe Leu Arg Gly Asn Thr Val Met
385                 390                 395                 400

Lys Gly Tyr Leu Lys Asn Pro Lys Ala Thr Glu Glu Ala Phe Arg Gly
                405                 410                 415

Gly Trp Phe His Thr Gly Asp Leu Ala Val Trp His Ala Asp Gly Tyr
                420                 425                 430

Ala Glu Ile Lys Asp Arg Leu Lys Asp Ile Ile Ile Ser Gly Gly Glu
            435                 440                 445
```

```
Asn Ile Ser Thr Ile Glu Val Glu Asp Val Leu Tyr Arg His Pro Asp
        450                 455                 460

Ile Leu Glu Ala Ala Val Val Ala Arg Pro Asp Glu Lys Trp Gly Glu
465                 470                 475                 480

Thr Pro Cys Ala Phe Val Thr Leu Lys Pro Glu Ala Gly Glu Val Ser
                485                 490                 495

Glu Asp Asp Ile Ile Ala Phe Cys Arg Glu Arg Met Ala Lys Phe Lys
            500                 505                 510

Val Pro Lys Thr Ile Val Phe Ser Glu Leu Pro Lys Thr Ser Thr Gly
        515                 520                 525

Lys Ile Gln Lys Phe Val Leu Arg Asp Asp Ala Lys Lys Leu
    530                 535                 540

<210> SEQ ID NO 3
<211> LENGTH: 542
<212> TYPE: PRT
<213> ORGANISM: Marinobacter manganoxydans MnI7-9

<400> SEQUENCE: 3

Met Thr Ser Ile Phe Asp Gln Gly Leu Ala Pro Val Asp Ala Asn Tyr
1               5                   10                  15

Ala Val Gln Ser Pro Val Asp Phe Ile Glu Arg Thr Ala Thr Val Tyr
            20                  25                  30

Pro Glu Tyr Pro Ala Val Ile His Gly Ala Ile Arg Tyr Asn Trp Ala
        35                  40                  45

Gln Thr Tyr Glu Arg Cys Arg Arg Leu Ala Ser Ala Leu Lys Gly Arg
    50                  55                  60

Gly Ile Gly Arg Gly Asp Thr Val Ala Val Met Leu Pro Asn Ile Pro
65                  70                  75                  80

Ala Met Val Glu Ala His Phe Gly Val Pro Met Ile Gly Ala Val Leu
                85                  90                  95

Asn Thr Leu Asn Val Arg Leu Asp Ala Glu Ala Ile Ala Phe Met Leu
            100                 105                 110

Asp His Gly Glu Ala Lys Val Val Ile Ala Asp Arg Glu Phe Gly Glu
        115                 120                 125

Val Ile Arg Asp Ala Val Ser Arg Leu Asp Thr Lys Pro Leu Val Ile
    130                 135                 140

Asp Val Asp Asp Pro Glu Tyr Gly Glu Gly Val Gln Val Ser Asp Leu
145                 150                 155                 160

Asp Tyr Glu Ala Phe Leu Gln Glu Gly Asp Pro Ala Phe Gln Trp Ser
                165                 170                 175

Phe Pro Glu Asn Glu Trp Asp Ala Ile Ser Leu Asn Tyr Thr Ser Gly
            180                 185                 190

Thr Thr Gly Asn Pro Lys Gly Val Val Tyr His His Arg Gly Ala Tyr
        195                 200                 205

Ile Asn Ala Ile Gly Asn Gln Thr Val Trp Ser Met Asp Met His Pro
    210                 215                 220

Val Tyr Leu Trp Thr Leu Pro Met Phe His Cys Asn Gly Trp Cys Phe
225                 230                 235                 240

Pro Trp Thr Ile Thr Ala Met Ala Gly Thr His Val Cys Leu Arg Arg
                245                 250                 255

Val Asp Pro Glu Lys Ile Leu Gln Leu Ile Arg Asp His Gln Val Thr
            260                 265                 270

His Met Cys Gly Ala Pro Ile Val Leu Asn Ala Leu Leu Asn Val Pro
        275                 280                 285
```

-continued

Glu Ser Ala Lys Ala Gly Ile Asp His Asp Val Lys Ser Met Thr Ala
290                 295                 300

Gly Ala Ala Pro Pro Ala Gln Val Ile Gly Ala Ile Glu Glu Met Gly
305                 310                 315                 320

Ile Gln Val Thr His Val Tyr Gly Leu Thr Glu Val Tyr Gly Pro Val
                325                 330                 335

Thr Val Cys Ala Trp Lys Ser Glu Trp Asp Ala Leu Pro Leu His Asp
                340                 345                 350

Arg Ala Arg Lys Ala Arg Gln Gly Val Arg Tyr His Thr Leu Ala
                355                 360                 365

Gly Thr Met Val Gly Asp Pro Asn Thr Met Glu Pro Val Pro Lys Asp
370                 375                 380

Gly Lys Thr Ile Gly Glu Ile Phe Leu Arg Gly Asn Thr Val Met Lys
385                 390                 395                 400

Gly Tyr Leu Lys Asn Pro Lys Ala Thr Glu Glu Ala Phe Arg Gly Gly
                405                 410                 415

Trp Phe His Thr Gly Asp Leu Ala Val Trp His Glu Asp Gly Tyr Met
                420                 425                 430

Glu Ile Lys Asp Arg Leu Lys Asp Ile Ile Ser Gly Gly Glu Asn
                435                 440                 445

Ile Ser Thr Ile Glu Val Glu Asp Thr Leu Tyr Arg His Pro Ala Val
450                 455                 460

Leu Glu Ala Ala Val Val Ala Arg Pro Asp Glu Lys Trp Gly Glu Thr
465                 470                 475                 480

Pro Cys Ala Phe Val Thr Leu Lys Pro Glu Ala Gly Gln Val Ser Glu
                485                 490                 495

Glu Asp Ile Ile Asn Phe Cys Arg Glu His Leu Ala Arg Phe Lys Val
                500                 505                 510

Pro Lys Thr Ile Val Phe Ser Glu Leu Pro Lys Thr Ser Thr Gly Lys
                515                 520                 525

Ile Gln Lys Phe Val Leu Arg Asp Gln Ala Lys Glu Leu Asp
530                 535                 540

<210> SEQ ID NO 4
<211> LENGTH: 555
<212> TYPE: PRT
<213> ORGANISM: Burkholderia sp. RPE64

<400> SEQUENCE: 4

Met Thr His Ser Glu Glu Ile Met Thr Thr Pro Gly Ile Tyr Asp Glu
1               5                   10                  15

Gly Leu Pro Lys Thr Ala Ala Asn Phe Ala Val Met Thr Pro Leu Thr
                20                  25                  30

Phe Ile Glu Arg Ala Ala Ser Val Tyr Pro Asn Arg Pro Ala Val Val
                35                  40                  45

His Gly Asp Val Arg Arg Thr Trp Ser Glu Thr Tyr Ala Arg Thr Arg
            50                  55                  60

Arg Leu Ala Ser Ala Leu Ala Ala Arg Gly Ile Gly Val Gly Asp Thr
65              70                  75                  80

Val Ala Val Met Leu Pro Asn Thr Pro Glu Met Val Glu Ala His Phe
                85                  90                  95

Gly Val Pro Met Thr Gly Ala Val Leu Asn Ala Leu Asn Thr Arg Leu
                100                 105                 110

Asp Ala Ala Thr Leu Ala Phe Met Leu Thr His Gly Glu Ala Lys Ala
            115                 120                 125

-continued

```
Val Leu Val Asp Arg Glu Phe Ser Asp Val Met Arg Arg Ala Leu Glu
    130                 135                 140
Ser Val Pro Gln Lys Leu Leu Val Ile Asp Val Asp Asp Ser Gln Tyr
145                 150                 155                 160
Ala Gly Ala Gly Glu Arg Ile Gly Glu Ile Glu Tyr Glu Ala Leu Leu
                165                 170                 175
Ala Ser Gly Asp Pro Ala Tyr Glu Trp Thr Pro Pro Ser Asp Glu Trp
            180                 185                 190
Asn Ala Ile Cys Leu Asn Tyr Thr Ser Gly Thr Thr Gly Asn Pro Lys
        195                 200                 205
Gly Val Val Tyr His His Arg Gly Ala Tyr Thr Asn Ala Val Ser Asn
    210                 215                 220
Ile Leu Glu Trp Asp Met Pro Ala His Ala Val Tyr Leu Trp Thr Leu
225                 230                 235                 240
Pro Met Phe His Cys Asn Gly Trp Cys Phe Pro Trp Thr Ile Ala Ala
                245                 250                 255
Arg Ala Gly Val Asn Val Cys Leu Arg Arg Ile Asp Ala Lys Thr Val
            260                 265                 270
Phe Asp Leu Ile Arg Asn Glu Gly Val Thr His Tyr Cys Gly Ala Pro
        275                 280                 285
Ile Val Gln Asn Met Leu Val Asn Ala Pro Asp Glu Leu Lys Ala Gly
    290                 295                 300
Ile Ala Gln Lys Val Asn Ala Met Val Ala Gly Ala Ala Pro Pro Ala
305                 310                 315                 320
Ala Met Ile Glu Gly Met Glu Arg Met Gly Phe Gln Leu Thr His Val
                325                 330                 335
Tyr Gly Leu Thr Glu Val Tyr Gly Pro Ala Thr Val Cys Ala His Gln
            340                 345                 350
Ala Glu Trp Ser Glu Leu Asp Ile Gly Glu Arg Ala Arg Leu Asn Ala
        355                 360                 365
Arg Gln Gly Val Arg Tyr His Leu Gln Asp Ala Val Thr Val Arg Asp
    370                 375                 380
Pro Asp Thr Met Gln Leu Val Pro Pro Asp Gly Glu Thr Ile Gly Glu
385                 390                 395                 400
Ile Met Phe Arg Gly Asn Ile Ala Met Lys Gly Tyr Leu Lys Asn Ala
                405                 410                 415
Ala Ala Thr Glu Glu Ala Phe Arg Gly Gly Trp Phe His Thr Gly Asp
            420                 425                 430
Leu Ala Val Ala Tyr Pro Asp Gly Tyr Val Arg Ile Lys Asp Arg Ser
        435                 440                 445
Lys Asp Ile Ile Ile Ser Gly Gly Glu Asn Ile Ser Ser Ile Glu Val
    450                 455                 460
Glu Asp Val Leu Tyr Arg His Pro Ala Val Leu Ala Val Ala Val Val
465                 470                 475                 480
Ala Lys Pro Asp Ala Arg Trp Gly Glu Thr Pro Cys Ala Phe Val Glu
                485                 490                 495
Leu Lys Thr Gly Val His Val Ser Gly Glu Glu Leu Ile Ala His Cys
            500                 505                 510
Lys Gln His Leu Ala Gly Phe Lys Val Pro Arg Ala Ile Glu Phe Cys
        515                 520                 525
```

Glu Leu Pro Lys Thr Ser Thr Gly Lys Ile Gln Lys Phe Glu Leu Arg
            530                 535                 540

Lys Arg Ala Gly Ser Val Thr Ala Ile Asp Val
545                 550                 555

<210> SEQ ID NO 5
<211> LENGTH: 540
<212> TYPE: PRT
<213> ORGANISM: Pseudomonas putida

<400> SEQUENCE: 5

Met Ser Ile Tyr Ala Gln Gly Leu Met Pro Ala Val Asn His Val
1               5                   10                  15

Ala Leu Thr Pro Leu Ser Phe Ile Glu Arg Thr Ala Ala Val Tyr Gly
            20                  25                  30

Asn Tyr Pro Ala Val Ile His Gly Ala Ile Arg Arg Asn Trp Gln Glu
            35                  40                  45

Thr Tyr Gln Arg Cys Arg Arg Leu Ala Ser Ala Leu Ala Gly Arg Gly
        50                  55                  60

Ile Gly Arg Gly Asp Thr Val Ala Val Met Leu Pro Asn Thr Pro Thr
65                  70                  75                  80

Met Leu Glu Ala His Phe Gly Val Pro Met Thr Gly Ala Val Leu Asn
                85                  90                  95

Thr Leu Asn Val Arg Leu Asp Ala Glu Ala Ile Ala Phe Met Leu Gln
            100                 105                 110

His Gly Glu Ala Lys Val Leu Ile Thr Asp Arg Glu Phe His Ala Val
        115                 120                 125

Ile Glu Gly Ala Leu Ala Leu Leu Glu His Pro Pro Leu Val Val Asp
130                 135                 140

Val Asp Asp Pro Glu Tyr Gly Glu Gly Arg Ala Val Ser Gln Leu Asp
145                 150                 155                 160

Tyr Glu Ala Leu Leu Asn Glu Gly Asp Pro Glu Phe Ala Trp Glu Trp
                165                 170                 175

Pro Asp Asp Glu Trp Gln Ala Ile Ser Leu Asn Tyr Thr Ser Gly Thr
            180                 185                 190

Thr Gly Asn Pro Lys Gly Val Val Tyr His His Arg Gly Ala Tyr Leu
        195                 200                 205

Asn Ala Leu Gly Asn Gln Met Thr Trp Ala Met Gly His Arg Pro Val
210                 215                 220

Tyr Leu Trp Thr Leu Pro Met Phe His Cys Asn Gly Trp Cys Tyr Pro
225                 230                 235                 240

Trp Thr Ile Thr Ala Leu Ala Gly Thr His Val Phe Leu Arg Arg Val
                245                 250                 255

Asp Pro Gln Lys Ile Leu Thr Leu Ile Arg Glu His Lys Val Ser His
            260                 265                 270

Leu Cys Gly Ala Pro Ile Val Leu Asn Ala Leu Val Asn Met Pro Glu
        275                 280                 285

Ala Ala Lys Ala Ala Ile Glu His Pro Val Gln Ala Met Val Ala Gly
290                 295                 300

Ala Ala Pro Pro Ala Lys Val Ile Gly Ala Val Glu Glu Met Gly Ile
305                 310                 315                 320

Lys Val Thr His Thr Tyr Gly Leu Thr Glu Val Tyr Gly Pro Val Thr
                325                 330                 335

Val Cys Ala Trp His Asp Glu Trp Asp Ala Leu Ser Leu Glu Glu Arg
            340                 345                 350

```
Ala Arg Ile Lys Ser Arg Gln Gly Val Arg Tyr Pro Thr Leu Asp Gly
            355                 360                 365

Leu Met Val Ala Asp Pro Gln Thr Leu Gln Pro Val Pro Arg Asp Gly
    370                 375                 380

Asn Thr Leu Gly Glu Ile Phe Met Arg Gly Asn Thr Val Met Lys Gly
385                 390                 395                 400

Tyr Leu Lys Asn Pro Glu Ala Thr Ala Glu Ala Phe Arg Gly Gly Trp
                405                 410                 415

Phe His Thr Gly Asp Leu Ala Val Trp His Ala Asp Gly Tyr Ile Glu
            420                 425                 430

Ile Lys Asp Arg Leu Lys Asp Ile Ile Ile Ser Gly Gly Glu Asn Ile
        435                 440                 445

Ser Thr Ile Glu Val Glu Asp Ala Leu Tyr Lys His Pro Ala Val Leu
    450                 455                 460

Glu Ala Ala Val Val Ala Arg Pro Asp Glu Lys Trp Gly Glu Thr Pro
465                 470                 475                 480

Cys Ala Phe Val Ala Leu Lys Pro Gly Arg Glu Asp Thr Arg Glu Ala
                485                 490                 495

Asp Ile Thr Ser Trp Cys Arg Glu His Leu Ala Gly Phe Lys Val Pro
            500                 505                 510

Lys Thr Val Val Phe Gly Glu Leu Pro Lys Thr Ser Thr Gly Lys Ile
        515                 520                 525

Gln Lys Tyr Val Leu Arg Asp Arg Ala Lys Ala Leu
    530                 535                 540

<210> SEQ ID NO 6
<211> LENGTH: 546
<212> TYPE: PRT
<213> ORGANISM: Pseudomonas oleovorans

<400> SEQUENCE: 6

Met Leu Gly Gln Met Met Arg Asn Gln Leu Val Ile Gly Ser Leu Val
1               5                   10                  15

Glu His Ala Ala Arg Tyr His Gly Ala Arg Glu Val Val Ser Val Glu
            20                  25                  30

Thr Ser Gly Glu Val Thr Arg Ser Cys Trp Lys Glu Val Glu Leu Arg
        35                  40                  45

Ala Arg Lys Leu Ala Ser Ala Leu Gly Lys Met Gly Leu Thr Pro Ser
    50                  55                  60

Asp Arg Cys Ala Thr Ile Ala Trp Asn Asn Ile Arg His Leu Glu Val
65                  70                  75                  80

Tyr Tyr Ala Val Ser Gly Ala Gly Met Val Cys His Thr Ile Asn Pro
                85                  90                  95

Arg Leu Phe Ile Glu Gln Ile Thr Tyr Val Ile Asn His Ala Glu Asp
            100                 105                 110

Lys Val Val Leu Leu Asp Asp Thr Phe Leu Pro Ile Ile Ala Glu Ile
        115                 120                 125

His Gly Ser Leu Pro Lys Val Lys Ala Phe Val Leu Met Ala His Asn
    130                 135                 140

Asn Ser Asn Ala Ser Ala Gln Met Pro Gly Leu Ile Ala Tyr Glu Asp
145                 150                 155                 160

Leu Ile Gly Gln Gly Asp Asp Asn Tyr Ile Trp Pro Asp Val Asp Glu
                165                 170                 175
```

Asn Glu Ala Ser Ser Leu Cys Tyr Thr Ser Gly Thr Thr Gly Asn Pro
            180                 185                 190

Lys Gly Val Leu Tyr Ser His Arg Ser Thr Val Leu His Ser Met Thr
        195                 200                 205

Thr Ala Met Pro Asp Thr Leu Asn Leu Ser Ala Arg Asp Thr Ile Leu
    210                 215                 220

Pro Val Val Pro Met Phe His Val Asn Ala Trp Gly Thr Pro Tyr Ser
225                 230                 235                 240

Ala Ala Met Val Gly Ala Lys Leu Val Leu Pro Gly Pro Ala Leu Asp
                245                 250                 255

Gly Ala Ser Leu Ser Lys Leu Ile Ala Ser Glu Gly Val Ser Ile Ala
            260                 265                 270

Leu Gly Val Pro Val Val Trp Gln Gly Leu Leu Ala Ala Gln Ala Gly
        275                 280                 285

Asn Gly Ser Lys Ser Gln Ser Leu Thr Arg Val Val Gly Gly Ser
    290                 295                 300

Ala Cys Pro Ala Ser Met Ile Arg Glu Phe Asn Asp Ile Tyr Gly Val
305                 310                 315                 320

Glu Val Ile His Ala Trp Gly Met Thr Glu Leu Ser Pro Phe Gly Thr
                325                 330                 335

Ala Asn Thr Pro Leu Ala His His Val Asp Leu Ser Pro Asp Glu Lys
            340                 345                 350

Leu Ser Leu Arg Lys Ser Gln Gly Arg Pro Pro Tyr Gly Val Glu Leu
        355                 360                 365

Lys Ile Val Asn Asp Glu Gly Ile Arg Leu Pro Glu Asp Gly Arg Ser
370                 375                 380

Lys Gly Asn Leu Met Ala Arg Gly His Trp Val Ile Lys Asp Tyr Phe
385                 390                 395                 400

His Ser Asp Pro Gly Ser Thr Leu Ser Asp Gly Trp Phe Ser Thr Gly
                405                 410                 415

Asp Val Ala Thr Ile Asp Ser Asp Gly Phe Met Thr Ile Cys Asp Arg
            420                 425                 430

Ala Lys Asp Ile Ile Lys Ser Gly Gly Glu Trp Ile Ser Thr Val Glu
        435                 440                 445

Leu Glu Ser Ile Ala Ile Ala His Pro His Ile Val Asp Ala Ala Val
    450                 455                 460

Ile Ala Ala Arg His Glu Lys Trp Asp Glu Arg Pro Leu Leu Ile Ala
465                 470                 475                 480

Val Lys Ser Pro Asn Ser Glu Leu Thr Ser Gly Glu Val Cys Asn Tyr
                485                 490                 495

Phe Ala Asp Lys Val Ala Arg Trp Gln Ile Pro Asp Ala Ala Ile Phe
            500                 505                 510

Val Glu Glu Leu Pro Arg Asn Gly Thr Gly Lys Ile Leu Lys Asn Arg
        515                 520                 525

Leu Arg Glu Lys Tyr Gly Asp Ile Leu Leu Arg Ser Ser Ser Val
    530                 535                 540

Cys Glu
545

<210> SEQ ID NO 7
<211> LENGTH: 1174
<212> TYPE: PRT
<213> ORGANISM: Nocardia iowensis

<400> SEQUENCE: 7

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
    210                 215                 220

Asp Ala Val Arg Ala Arg Gly Arg Asp Leu Pro Ala Ala Pro Leu Phe
225                 230                 235                 240

Val Pro Asp Thr Asp Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
            260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
    290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
            340                 345                 350

Arg Tyr Gln Ser Glu Leu Asp Arg Arg Ser Val Ala Gly Ala Asp Leu
        355                 360                 365

Asp Thr Leu Asp Arg Glu Val Lys Ala Asp Leu Arg Gln Asn Tyr Leu
    370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

```
Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
            435                 440                 445

Leu Gly Tyr Phe Arg Thr Asp Arg Pro His Pro Arg Gly Glu Leu Leu
        450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
            500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
                725                 730                 735

Pro Thr Phe Thr Ser Val His Gly Gly Ser Glu Ile Arg Ala Ala
            740                 745                 750

Asp Leu Thr Leu Asp Lys Phe Ile Asp Ala Arg Thr Leu Ala Ala Ala
        755                 760                 765

Asp Ser Ile Pro His Ala Pro Val Pro Ala Gln Thr Val Leu Leu Thr
770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Ala Arg Lys Arg Leu Asp Ser Ala Phe Asp Ser Gly
            820                 825                 830
```

```
Asp Pro Gly Leu Leu Glu His Tyr Gln Gln Leu Ala Ala Arg Thr Leu
            835                 840                 845

Glu Val Leu Ala Gly Asp Ile Gly Asp Pro Asn Leu Gly Leu Asp Asp
    850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
    930                 935                 940

Val Arg Val Arg Glu Ser Tyr Ala Asn Gly Tyr Gly Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Ser Asp Met Ile Leu Ala His Ser Arg Tyr
            980                 985                 990

Ala Gly Gln Leu Asn Val Gln Asp Val Phe Thr Arg Leu Ile Leu Ser
        995                 1000                1005

Leu Val Ala Thr Gly Ile Ala Pro Tyr Ser Phe Tyr Arg Thr Asp Ala
    1010                1015                1020

Asp Gly Asn Arg Gln Arg Ala His Tyr Asp Gly Leu Pro Ala Asp Phe
1025                1030                1035                1040

Thr Ala Ala Ala Ile Thr Ala Leu Gly Ile Gln Ala Thr Glu Gly Phe
                1045                1050                1055

Arg Thr Tyr Asp Val Leu Asn Pro Tyr Asp Asp Gly Ile Ser Leu Asp
            1060                1065                1070

Glu Phe Val Asp Trp Leu Val Glu Ser Gly His Pro Ile Gln Arg Ile
        1075                1080                1085

Thr Asp Tyr Ser Asp Trp Phe His Arg Phe Glu Thr Ala Ile Arg Ala
    1090                1095                1100

Leu Pro Glu Lys Gln Arg Gln Ala Ser Val Leu Pro Leu Leu Asp Ala
1105                1110                1115                1120

Tyr Arg Asn Pro Cys Pro Ala Val Arg Gly Ala Ile Leu Pro Ala Lys
                1125                1130                1135

Glu Phe Gln Ala Ala Val Gln Thr Ala Lys Ile Gly Pro Glu Gln Asp
            1140                1145                1150

Ile Pro His Leu Ser Ala Pro Leu Ile Asp Lys Tyr Val Ser Asp Leu
        1155                1160                1165

Glu Leu Leu Gln Leu Leu
    1170

<210> SEQ ID NO 8
<211> LENGTH: 564
<212> TYPE: PRT
<213> ORGANISM: Shewanella amazonensis

<400> SEQUENCE: 8

Met Asn Ala Asn Leu Cys Arg His Leu Val Ser Ala Ala Gln Ala Gln
1               5                   10                  15

Pro Gln Gly Leu Ala Val Ala Val Gln Arg His Arg Phe Gly Lys Pro
            20                  25                  30
```

```
Pro Arg Gly Ile Gly Glu Leu Cys Tyr Asp Glu Leu Thr Leu Ser Glu
         35                  40                  45

Leu Asn Arg Arg Ser Asp Ala Ile Ala His Gly Leu Asn Ala Ile Gly
     50                  55                  60

Leu Asn Ala Gly Asp Lys Ala Val Leu Met Val Thr Pro Gly Leu Asp
 65                  70                  75                  80

Phe Phe Ala Leu Thr Phe Ala Leu Phe Lys Ala Gly Ile Ile Pro Val
                 85                  90                  95

Met Val Asp Pro Gly Met Gly Ile Lys Asn Leu Gly Gln Cys Phe Asp
             100                 105                 110

Glu Ala Ala Pro Asp Ala Phe Ile Gly Ile Pro Lys Ala His Val Ala
         115                 120                 125

Arg Met Leu Phe Ser Trp Gly Lys Lys Thr Val Thr Gln Leu Val Thr
     130                 135                 140

Val Gly Arg Gly Leu Lys Leu Trp Gly Gly Asn Thr Leu Val Gln Ile
145                 150                 155                 160

Glu Lys His Gly Gln Asp Met Gly Pro Tyr Pro Met Thr Leu Leu Asp
             165                 170                 175

Glu Gln Ala Leu Cys Ala Ile Leu Phe Thr Ser Gly Ser Thr Gly Val
         180                 185                 190

Pro Lys Gly Val Glu Tyr Ser His Gln Met Phe Glu Ala Gln Ile Gln
     195                 200                 205

Ala Leu Lys Gln Asp Tyr Gly Ile Arg His Gly Glu Arg Asp Leu Ser
     210                 215                 220

Thr Phe Pro Leu Phe Ala Leu Phe Gly Pro Ala Leu Gly Met Ala Ser
225                 230                 235                 240

Ile Val Pro Cys Met Asp Ala Ser Arg Pro Ile Lys Ala Lys Pro Glu
             245                 250                 255

Tyr Leu Phe Lys Ala Ile Ala Asp Tyr Gln Cys Thr Asn Leu Phe Leu
         260                 265                 270

Asn Pro Ala Leu Leu Asp Lys Leu Gly Arg Tyr Gly Glu Ala Asn Ala
     275                 280                 285

Leu Thr Leu Asn Gly Val Arg Arg Val Ile Ser Ala Gly Ala Pro Ala
     290                 295                 300

Ser Ile Asp Ala Ile Asn Arg Phe Arg Gln Ile Leu Pro Pro Asp Ala
305                 310                 315                 320

Pro Val Leu Asn Ser Tyr Gly Ala Thr Glu Gly Leu Pro Leu Cys Phe
             325                 330                 335

Val Gly Ser Asp Glu Leu Leu Ala Ser Gly Glu Val Thr Ala Lys Gly
         340                 345                 350

Gly Gly Ile Leu Val Gly Lys Pro Val Gln Gly Val Ala Leu Glu Ile
     355                 360                 365

Ile Ala Ile Asp Glu Ala Pro Ile Ala Glu Trp Gln Asp Glu Leu Lys
     370                 375                 380

Leu Gln Pro Tyr Glu Ile Gly Glu Ile Val Val Lys Gly Pro Met Val
385                 390                 395                 400

Ser Arg Ala Tyr Tyr His Arg Asp Glu Ala Thr Ser Ile Ala Lys Ile
             405                 410                 415

Ala Asp Asp Gly Glu Phe Trp His Arg Met Gly Asp Leu Gly Tyr Leu
         420                 425                 430

Asp Glu Leu Gly Arg Leu Trp Met Cys Gly Arg Lys Ala His Arg Val
     435                 440                 445
```

```
Asp Ala Thr Glu Gly Gly Ala Phe Ser Lys Arg Tyr Phe Ser Ile Pro
    450                 455                 460

Cys Glu Arg Ile Phe Asn Thr His Pro Leu Val Ala Arg Ser Ala Leu
465                 470                 475                 480

Val Gly Val His Arg His Gly Asp Lys Ile Pro Leu Val Cys Leu Glu
                485                 490                 495

Leu Glu Arg Ser Gln Ala Cys Asn Asn Ala Ser Ser Leu Tyr Arg Glu
            500                 505                 510

Leu Arg Glu Met Ala Glu Ala His Glu Ile Thr Gln Gly Ile Asp Phe
        515                 520                 525

Phe Leu Ile His Glu Ser Phe Pro Met Asp Val Arg His Asn Ala Lys
    530                 535                 540

Ile Phe Arg Glu Lys Leu Ala Leu Trp Ala Glu Lys Gln Leu Ser Gly
545                 550                 555                 560

Gly Leu Asn Lys

<210> SEQ ID NO 9
<211> LENGTH: 563
<212> TYPE: PRT
<213> ORGANISM: Shewanella loihica

<400> SEQUENCE: 9

Met Ser Glu Thr Ile Gln Val Gly Ala Asn Leu Cys Arg His Leu Asn
1               5                   10                  15

Arg Ala Ala Lys Glu Ala Pro Asn Glu Leu Ala Val Ala Val Gln Lys
            20                  25                  30

Ala Cys Gly Val Leu Asn Lys Gln Leu Glu Tyr Gln Glu Leu Asn Phe
        35                  40                  45

Ala Lys Leu Asp Ala Met Ser Asp Ile Leu Ala His Gly Leu Tyr Ala
    50                  55                  60

Tyr Gly Ile Lys Arg Gly Ala Lys Ala Val Leu Met Val Thr Pro Ser
65                  70                  75                  80

Leu Glu Phe Phe Ala Leu Thr Phe Ala Leu Phe Lys Ala Gly Ile Val
                85                  90                  95

Pro Ile Leu Val Asp Pro Gly Met Gly Val Lys Asn Leu Lys Gln Cys
            100                 105                 110

Phe Gln Glu Ala Glu Pro Asp Ala Phe Ile Gly Ile Pro Lys Ala His
        115                 120                 125

Leu Ala Arg Arg Leu Phe Gly Trp Gly Lys Ser Ser Leu Thr His Leu
    130                 135                 140

Val Thr Val Gly Gly Ser Lys Leu Trp Gly Gly Ala Ser Leu Glu Gln
145                 150                 155                 160

Leu Lys Gln Leu Gly Gln Gly Lys Gly Pro Phe Ser Met Ala Gln Leu
                165                 170                 175

Asp Cys Asp Glu Met Cys Ala Ile Leu Phe Thr Ser Gly Ser Thr Gly
            180                 185                 190

Thr Pro Lys Gly Val Val Tyr Ser His Arg Met Phe Glu Ala Gln Ile
        195                 200                 205

Ser Ala Leu Lys His Asp Tyr Gln Ile Ala Pro Gly Glu Arg Asp Leu
    210                 215                 220

Ala Thr Phe Pro Leu Phe Ser Leu Phe Gly Pro Ala Leu Gly Met Ala
225                 230                 235                 240

Ser Ile Val Pro Asp Met Asp Ala Ser Lys Pro Ile Thr Ala Asn Pro
                245                 250                 255
```

```
Asp Tyr Ile Phe Ala Ala Ile Glu Arg Tyr Ala Cys Thr Asn Met Phe
            260                 265                 270

Val Asn Pro Ala Leu Ile Glu Arg Leu Gly Gln Ala Gly Thr Ser Arg
        275                 280                 285

Asp Gln Lys Val Lys Leu Gly Ser Leu Lys Arg Val Ile Ser Ala Gly
    290                 295                 300

Ala Pro Ala Thr Ile Ala Ser Ile Lys Arg Phe Ser Glu Met Leu Thr
305                 310                 315                 320

Ser Asp Ala Pro Val Leu Asn Ser Tyr Gly Ala Thr Glu Ser Leu Pro
                325                 330                 335

Leu Ser Met Ile Thr Ser His Glu Leu Phe Asp Thr Thr Glu Val Thr
            340                 345                 350

Asp Asn Gly Gly Gly Ile Cys Val Gly Lys Pro Ile Asp Gly Val Ser
        355                 360                 365

Met His Ile Ile Asp Ile Asp Glu Ala Glu Ile Pro Thr Trp Ser Ala
    370                 375                 380

Asp Leu Cys Leu Pro Arg Glu Gln Ile Gly Glu Ile Val Val Gln Gly
385                 390                 395                 400

Pro Met Val Ser Ala Ser Tyr Tyr Arg Arg Asp Lys Ala Thr Ala Gln
                405                 410                 415

Ala Lys Ile Phe Asp Asp Gln Gly Gln His Tyr His Arg Met Gly Asp
            420                 425                 430

Leu Gly Tyr Leu Asp Asn Gln Gly Arg Leu Trp Met Cys Gly Arg Lys
        435                 440                 445

Ala His Arg Val Asp Cys Arg Val Asp Gly Gln Pro Arg Arg Tyr Phe
    450                 455                 460

Ser Ile Pro Cys Glu Arg Ile Tyr Asn Thr His Ser Asp Ile Lys Arg
465                 470                 475                 480

Ser Ala Leu Val Gly Ile Lys Val Lys Gly Glu Met Gln Pro Leu Ile
                485                 490                 495

Cys Leu Glu Leu Glu Gln Gly Leu Ser Cys Ser Asn Ala Ala Ala Leu
            500                 505                 510

Tyr Thr Glu Leu Arg Leu Leu Gly Glu Ala His Ser Gln Thr Gln Gly
        515                 520                 525

Ile Thr Arg Phe Leu Ile His Pro Gly Phe Pro Val Asp Ile Arg His
    530                 535                 540

Asn Ala Lys Ile Phe Arg Glu Lys Leu Ala Val Trp Ala Gln Ser Thr
545                 550                 555                 560

Tyr Lys Glu

<210> SEQ ID NO 10
<211> LENGTH: 552
<212> TYPE: PRT
<213> ORGANISM: Stenotrophomonas maltophilia

<400> SEQUENCE: 10

Met Asn Arg Pro Cys Asn Ile Ala Ala Arg Leu Pro Glu Leu Ala Arg
1               5                   10                  15

Glu Arg Pro Asp Gln Ile Ala Ile Arg Cys Pro Gly Arg Arg Gly Ala
            20                  25                  30

Gly Asn Gly Met Ala Ala Tyr Asp Val Thr Leu Asp Tyr Arg Gln Leu
        35                  40                  45

Asp Ala Arg Ser Asp Ala Met Ala Ala Gly Leu Ala Gly Tyr Gly Ile
    50                  55                  60
```

Gly Arg Gly Val Arg Thr Val Val Met Val Arg Pro Ser Pro Glu Phe
65                  70                  75                  80

Phe Leu Leu Met Phe Ala Leu Phe Lys Leu Gly Ala Val Pro Val Leu
                85                  90                  95

Val Asp Pro Gly Ile Asp Lys Arg Ala Leu Lys Gln Cys Leu Asp Glu
            100                 105                 110

Ala Gln Pro Glu Ala Phe Ile Gly Ile Pro Leu Ala His Val Ala Arg
        115                 120                 125

Leu Val Leu Arg Trp Ala Pro Ser Ala Thr Arg Leu Val Thr Val Gly
    130                 135                 140

Arg Arg Leu Gly Trp Gly Gly Thr Thr Leu Ala Ala Leu Glu Arg Ala
145                 150                 155                 160

Gly Ala Asn Gly Gly Pro Met Leu Ala Ala Thr Asp Gly Glu Asp Met
                165                 170                 175

Ala Ala Ile Leu Phe Thr Ser Gly Ser Thr Gly Val Pro Lys Gly Val
            180                 185                 190

Val Tyr Arg His Arg His Phe Val Gly Gln Ile Gln Leu Leu Gly Ser
        195                 200                 205

Ala Phe Gly Met Glu Ala Gly Gly Val Asp Leu Pro Thr Phe Pro Pro
    210                 215                 220

Phe Ala Leu Phe Asp Pro Ala Leu Gly Leu Thr Ser Val Ile Pro Asp
225                 230                 235                 240

Met Asp Pro Thr Arg Pro Ala Gln Ala Asp Pro Ala Arg Leu His Asp
                245                 250                 255

Ala Ile Gln Arg Phe Gly Val Thr Gln Leu Phe Gly Ser Pro Ala Leu
            260                 265                 270

Met Arg Val Leu Ala Arg His Gly Arg Pro Leu Pro Thr Val Thr Arg
        275                 280                 285

Val Thr Ser Ala Gly Ala Pro Val Pro Pro Asp Val Val Ala Thr Ile
    290                 295                 300

Arg Ser Leu Leu Pro Ala Asp Ala Gln Phe Trp Thr Pro Tyr Gly Ala
305                 310                 315                 320

Thr Glu Cys Leu Pro Val Ala Val Glu Gly Arg Glu Leu Glu Arg
                325                 330                 335

Thr Arg Ala Ala Thr Glu Ala Gly Ala Gly Thr Cys Val Gly Ser Val
            340                 345                 350

Val Glu Pro Asn Glu Val Arg Ile Ile Ala Ile Asp Asp Ala Pro Leu
        355                 360                 365

Pro Asp Trp Ser Gln Ala Arg Val Leu Phe Thr Gly Glu Val Gly Glu
    370                 375                 380

Ile Thr Val Ala Gly Pro Thr Ala Thr Asp Ser Tyr Phe Asn Arg Pro
385                 390                 395                 400

Gln Ala Thr Ala Ala Lys Ile Ser Glu Thr Leu Ala Asp Gly Ser
                405                 410                 415

Val Arg Val Val His Arg Met Gly Asp Val Gly Tyr Phe Asp Ala Gln
            420                 425                 430

Gly Arg Leu Trp Phe Cys Gly Arg Lys Thr His Arg Val Glu Thr Ala
        435                 440                 445

His Gly Pro Leu Tyr Thr Glu Gln Val Glu Pro Val Phe Asn Thr Val
    450                 455                 460

Pro Gly Val Ala Arg Thr Ala Leu Val Gly Val Gly Pro Ala Gly Ala
465                 470                 475                 480

-continued

Gln Val Pro Val Leu Cys Val Glu Leu Gln Arg Gly Gln Ser Asp Ser
485 490 495

Pro Ala Leu Gln Glu Ala Leu Arg Ala His Ala Ala Ala Arg Ala Pro
500 505 510

Glu Ala Gly Leu Gln His Phe Leu Val His Pro Ala Phe Pro Val Asp
515 520 525

Ile Arg His Asn Ala Lys Ile Gly Arg Glu Lys Leu Ala Val Trp Ala
530 535 540

Ser Thr Glu Leu Glu Lys Arg Ala
545 550

<210> SEQ ID NO 11
<211> LENGTH: 556
<212> TYPE: PRT
<213> ORGANISM: Xanthomonas campestris pv. campestris

<400> SEQUENCE: 11

Met Gly Asp Asn Gly Arg Met Thr Thr Leu Cys Asn Ile Ala Ala Ser
1 5 10 15

Leu Pro Arg Leu Ala Arg Glu Arg Pro Asp Gln Ile Ala Ile Arg Cys
20 25 30

Pro Gly Gly Arg Gly Ala Asn Gly Met Ala Ala Tyr Asp Val Thr Leu
35 40 45

Ser Tyr Ala Glu Leu Asp Ala Arg Ser Asp Ala Ile Ala Ala Gly Leu
50 55 60

Ala Leu His Gly Ile Gly Arg Gly Val Arg Ala Val Val Met Val Arg
65 70 75 80

Pro Ser Pro Glu Phe Phe Leu Leu Met Phe Ala Leu Phe Lys Ala Gly
85 90 95

Ala Val Pro Val Leu Val Asp Pro Gly Ile Asp Lys Arg Ala Leu Lys
100 105 110

Gln Cys Leu Asp Glu Ala Gln Pro Gln Ala Phe Ile Gly Ile Pro Leu
115 120 125

Ala Gln Leu Ala Arg Arg Leu Leu Arg Trp Ala Pro Ser Ala Thr Gln
130 135 140

Ile Val Thr Val Gly Gly Arg Tyr Cys Trp Gly Gly Val Thr Leu Ala
145 150 155 160

Arg Val Glu Arg Asp Gly Ala Gly Ala Gly Ser Gln Leu Ala Asp Thr
165 170 175

Ala Ala Asp Asp Val Ala Ala Ile Leu Phe Thr Ser Gly Ser Thr Gly
180 185 190

Val Pro Lys Gly Val Val Tyr Arg His Arg His Phe Val Gly Gln Ile
195 200 205

Glu Leu Leu Arg Asn Ala Phe Asp Met Gln Pro Gly Gly Val Asp Leu
210 215 220

Pro Thr Phe Pro Pro Phe Ala Leu Phe Asp Pro Ala Leu Gly Leu Thr
225 230 235 240

Ser Val Ile Pro Asp Met Asp Pro Thr Arg Pro Ala Thr Ala Asp Pro
245 250 255

Arg Lys Leu His Asp Ala Met Thr Arg Phe Gly Val Thr Gln Leu Phe
260 265 270

Gly Ser Pro Ala Leu Met Arg Val Leu Ala Asp Tyr Gly Gln Pro Leu
275 280 285

Pro Asn Val Arg Leu Ala Thr Ser Ala Gly Ala Pro Val Pro Pro Asp
290 295 300

Val Val Ala Lys Ile Arg Ala Leu Leu Pro Ala Asp Ala Gln Phe Trp
305                 310                 315                 320

Thr Pro Tyr Gly Ala Thr Glu Cys Leu Pro Val Ala Ala Ile Glu Gly
            325                 330                 335

Arg Thr Leu Asp Ala Thr Arg Thr Ala Thr Glu Ala Gly Ala Gly Thr
        340                 345                 350

Cys Val Gly Gln Val Val Ala Pro Asn Glu Val Arg Ile Ile Ala Ile
    355                 360                 365

Asp Asp Ala Ala Ile Pro Glu Trp Ser Gly Val Arg Val Leu Ala Ala
370                 375                 380

Gly Glu Val Gly Glu Ile Thr Val Ala Gly Pro Thr Thr Thr Asp Thr
385                 390                 395                 400

Tyr Phe Asn Arg Asp Ala Ala Thr Arg Asn Ala Lys Ile Arg Glu Arg
                405                 410                 415

Cys Ser Asp Gly Ser Glu Arg Val Val His Arg Met Gly Asp Val Gly
            420                 425                 430

Tyr Phe Asp Ala Glu Gly Arg Leu Trp Phe Cys Gly Arg Lys Thr His
        435                 440                 445

Arg Val Glu Thr Ala Thr Gly Pro Leu Tyr Thr Glu Gln Val Glu Pro
    450                 455                 460

Ile Phe Asn Val His Pro Gln Val Arg Arg Thr Ala Leu Val Gly Val
465                 470                 475                 480

Gly Thr Pro Gly Gln Gln Pro Val Leu Cys Val Glu Leu Gln Pro
                485                 490                 495

Gly Val Ala Ala Ser Ala Phe Ala Glu Val Glu Thr Ala Leu Arg Ala
            500                 505                 510

Val Gly Ala Ala His Pro His Thr Ala Gly Ile Ala Arg Phe Leu Arg
        515                 520                 525

His Ser Gly Phe Pro Val Asp Ile Arg His Asn Ala Lys Ile Gly Arg
    530                 535                 540

Glu Lys Leu Ala Ile Trp Ala Ala Gln Gln Arg Val
545                 550                 555

<210> SEQ ID NO 12
<211> LENGTH: 564
<212> TYPE: PRT
<213> ORGANISM: Chloroflexus aurantiacus

<400> SEQUENCE: 12

Met Arg Asn Glu Glu Gln Thr Ala Ala Arg Val Thr Phe Thr Val Val
1               5                   10                  15

Ala Gly Ala Asn Val Ala Arg His Leu Pro Leu Met Ala Arg Glu Arg
                20                  25                  30

Pro Asp Gln Thr Ala Val Val Ser Gly Val Gly Arg Asp Arg Ala Gly
            35                  40                  45

Lys Val Ile Tyr Arg Arg Gln Ser Phe Ala Gly Leu His Ala Ala Ser
    50                  55                  60

Asp Arg Leu Ala Trp Gly Leu Thr Ala Tyr Gly Leu Arg Lys Gly Met
65                  70                  75                  80

Arg Val Leu Leu Met Val Pro Ala Gly Val Pro Leu Ile Ser Leu Thr
                85                  90                  95

Phe Ala Leu Met Lys Ala Gly Cys Val Pro Ile Leu Ile Asp Pro Ala
            100                 105                 110

Met Gly Arg Arg Asn Leu Ala Gln Cys Ile Ala Glu Val Glu Pro Glu
    115                 120                 125

```
Ala Phe Ile Gly Val Pro Arg Ala His Leu Leu Arg Leu Ile Phe Pro
130                 135                 140

Arg Ser Cys Ala Thr Ile Arg Tyr Ala Val Ser Val Gly Pro Ala Leu
145                 150                 155                 160

Pro Gly Ala Ala Ala Leu Arg Glu Leu Asp Ile Pro Met Lys Thr Ala
                165                 170                 175

Phe Pro Leu Ala Asp Met Arg Ser Asp Asp Pro Ala Ala Ile Val Phe
                180                 185                 190

Thr Ser Gly Ser Thr Gly Thr Pro Lys Gly Val Leu Tyr Thr His Gly
                195                 200                 205

Met Phe Glu Ala Gln Ile His Thr Leu Arg Asp Leu Phe Gly Ile Ala
210                 215                 220

Ala Gly Glu Val Glu Met Pro Ala Phe Pro Leu Phe Ala Leu Phe Asn
225                 230                 235                 240

Val Ala Leu Gly Val Thr Ser Ala Ile Pro Ile Asp Pro Thr Arg
                245                 250                 255

Pro Ala Gln Cys Asp Pro Ala Ala Val Val Glu Phe Ile Arg Asp Leu
                260                 265                 270

Gly Val Thr Ser Thr Phe Gly Ser Pro Ala Ile Trp Glu Lys Val Thr
                275                 280                 285

Ala Tyr Cys Leu Thr His Gly Ile Gln Leu Pro Ser Leu Arg Arg Val
290                 295                 300

Leu Met Ala Gly Ala Pro Val Pro Ile His Leu His Glu Arg Leu His
305                 310                 315                 320

Arg Ile Leu Ser Pro Thr Ala Asp Ser Phe Thr Pro Tyr Gly Ala Thr
                325                 330                 335

Glu Ala Leu Pro Val Thr Ser Ile Ser Gly Arg Glu Val Leu Ala Ala
                340                 345                 350

His Thr Glu Tyr Pro Ser Pro Leu Ala Gly Thr Cys Ile Gly Tyr Pro
                355                 360                 365

Val Pro Gly Val Glu Val Ala Ile Ile Pro Ile Thr Asp Glu Pro Ile
                370                 375                 380

His Ala Trp Gln Asp Thr His Arg Leu Pro Pro Gly Val Ile Gly Glu
385                 390                 395                 400

Ile Cys Val Ser Gly Ala Thr Val Thr His Thr Tyr Val Gly Arg Pro
                405                 410                 415

Gln Ala Thr Ala Leu Ala Lys Ile Ser Asp Gly Asn Arg Ile Trp His
                420                 425                 430

Arg Met Gly Asp Leu Gly Tyr Phe Asp Glu Arg Gly Arg Leu Trp Phe
                435                 440                 445

Tyr Gly Arg Lys Ser Gln Arg Val Ile Thr Ala His Gly Thr Leu Phe
                450                 455                 460

Thr Glu Pro Val Glu Arg Leu Phe Asn Gln His Pro Ala Val Ala Arg
465                 470                 475                 480

Ser Ala Leu Val Gly Ile Gly Lys Pro Gly Thr Gln Leu Pro Val Val
                485                 490                 495

Val Val Glu Arg Arg Asp Arg Ala Ile Ser Thr Ser Gln Leu Ile
                500                 505                 510

Arg Glu Leu Arg Gln Leu Ala Thr Thr Thr Glu Thr Ala Ile Ile
                515                 520                 525

Gln Thr Phe Leu Ile His Pro Ser Phe Pro Val Asp Ile Arg His Asn
530                 535                 540
```

| Ala | Lys | Ile | Phe | Arg | Glu | Gln | Leu | Ala | Asp | Trp | Ala | Ala | Arg | Arg | Leu |
|---|---|---|---|---|---|---|---|---|---|---|---|---|---|---|---|
| 545 | | | | | 550 | | | | | 555 | | | | | 560 |

Cys Ile Pro Val

PRODUCTION OF ALKENES FROM 3-HYDROXYCARBOXYLIC ACIDS VIA 3-HYDROXYCARBOXYL-NUCLEOTIDYLIC ACIDS

CROSS-REFERENCE TO RELATED APPLICATIONS

This application is a § 371 National Stage Application of PCT/EP2014/076203, filed Dec. 2, 2014, which claims priority to EP 13195569.2, filed Dec. 3, 2013. All of these documents (PCT/EP2014/076203 and EP 13195569.2) are hereby incorporated by reference in their entirety.

The present invention relates to a method for generating alkenes through a biological process. More specifically, the invention relates to a method for producing alkenes (for example propylene, ethylene, 1-butylene, isobutylene, isoamylene, butadiene or isoprene) from 3-hydroxycarboxylic acids via 3-hydroxycarboxyl-nucleotidylic acids.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Ethylene, the simplest alkene, lies at the heart of industrial organic chemistry: it is the most widely produced organic compound in the world. It is used in particular to produce polyethylene, a major plastic. Ethylene can also be converted to many industrially useful products by reaction (of oxidation, of halogenation).

Propylene holds a similarly important role: its polymerization results in a plastic material, polypropylene. The technical properties of this product in terms of resistance, density, solidity, deformability, and transparency are unequalled. The worldwide production of polypropylene has grown continuously since its invention in 1954.

Butylene exists in four forms, one of which, isobutylene, enters into the composition of methyl-tert-butyl-ether (MTBE), an anti-knock additive for automobile fuel. Isobutylene can also be used to produce isooctane, which in turn can be reduced to isooctane (2,2,4-trimethylpentane); the very high octane rating of isooctane makes it the best fuel for so-called "gasoline" engines.

Amylene, hexene and heptene exist in many forms according to the position and configuration of the double bond. These products have real industrial applications but are less important than ethylene, propylene or butenes.

All these alkenes are currently produced by catalytic cracking of petroleum products (or by a derivative of the Fisher-Tropsch process in the case of hexene, from coal or gas). Their cost is therefore naturally indexed to the price of oil. Moreover, catalytic cracking is sometimes associated with considerable technical difficulties which increase process complexity and production costs. In the alkene chemical family, isoprene (2-methyl-1,3-butadiene) is the terpene motif which, through polymerization, leads to rubber. Other terpenes might be developed, by chemical, biological or mixed pathways, as usable products such as biofuels or to manufacture plastics. WO2008/113041 proposes a biological process for producing hydrocarbons from renewal resources in which the microorganism converts a substrate containing a fatty acyl chain. The production of alkenes, in particular terminal alkenes (ethylene mono- or di-substituted at position 2: $H_2C=C(R^1)(R^2)$) has apparently been less extensively investigated. The conversion of isovalerate to isobutylene by the yeast *Rhodotorula minuta* has been described (Fujii T. et al., Appl. Environ. Microbiol., 1988, 54:583), but the efficiency of this reaction, characterized by a very low value of the turnover number ($k_{cat}$ is $1 \times 10^{-5}$ sec$^{-1}$), is far from permitting an industrial application. Large-scale biosynthesis of isobutylene by this pathway seems highly unfavorable, since it would require the synthesis and degradation of one molecule of leucine to form one molecule of isobutylene. Also, the enzyme catalyzing the reaction uses heme as cofactor, poorly lending itself to recombinant expression in bacteria and to improvement of enzyme parameters. Other microorganisms have been described as being marginally capable of naturally producing isobutylene from isovalerate; the yields obtained are even lower than those obtained with *Rhodotorula minuta* (Fukuda H. et al, Agric. Biol. Chem., 1984, 48:1679).

The same studies have also described the natural production of propylene: many microorganisms are capable of producing propylene, once again with an extremely low yield. The production of ethylene by plants has long been known (Meigh et al, 1960, Nature, 186:902). According to the metabolic pathway elucidated, methionine is the precursor of ethylene (Adams and Yang, PNAS, 1979, 76:170). Conversion of 2-oxoglutarate has also been described (Ladygina N et al., Process Biochemistry 2006, 41:1001). Since the production of a two-carbon molecule of ethylene consumes a four- or five-carbon molecule precursor, these pathways appear materially and energetically unfavorable for their industrial application.

WO2010/001078 describes a process for producing alkenes by enzymatic conversion of 3-hydroxyalkanoic acids with an enzyme having the activity of a decarboxylase. Such a method is advantageous because it helps to avoid the use of petroleum products, to lower the costs of producing plastics and fuels and can have a considerable global environmental impact by allowing carbon to be stored in solid form. Although the method described in WO 2010/001078 allows producing alkenes by enzymatic reactions, there is still a need for further methods allowing the production of alkenes in biological systems which can be extended to an industrial scale. The present application addresses this need.

The present invention relates to a method for producing an alkene characterized in that it comprises the conversion of a 3-hydroxycarboxylate through a biological process, in particular an enzymatic process, wherein a 3-hydroxycarboxylate is, in a first step, enzymatically converted into a 3-hydroxycarboxyl-nucleotidylate and wherein the thus produced 3-hydroxycarboxyl-nucleotidylate is subsequently converted into the alkene. The enzymatic conversion of the 3-hydroxycarboxylate in the first step into a 3-hydroxycarboxyl-nucleotidylate comprises a nucleotidylation reaction. The conversion of the produced 3-hydroxycarboxyl-nucleotidylate into the alkene comprises an elimination of carbon dioxide and denucleotidylation. When used in the present invention, the suffix "-ate/-oate" can interchangeable denote either the carboxylate ion (COO—) or carboxylic acid (COOH).

The term "3-hydroxycarboxylate", as used herein, denotes a molecule responding to the following general formula I:

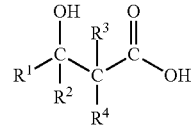

Formula I in which $R^1$ and $R^3$ are independently selected from hydrogen (—H), methyl (—CH$_3$), ethyl (—CH$_2$—CH$_3$), isopropyl (—CH$_2$(CH$_3$)$_2$), vinyl (—CH=CH$_2$) and isopropenyl (—C(CH$_3$)=CH$_2$) and in which $R^2$ and $R^4$ are independently selected from hydrogen (—H) and methyl (—CH$_3$).

According to a method of the invention the 3-hydroxycarboxylate is enzymatically converted together with a co-substrate responding to the following general formula II:

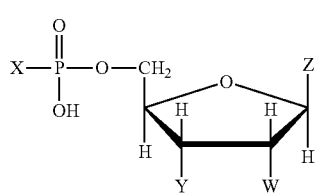

Formula II wherein X is selected from the group consisting of

O—PO$_3$H$_2$ monophosphate,

O—PO$_2$H—O—PO$_3$H$_2$ diphosphate, and

O—SO$_3$H sulfate, and wherein Y is selected from the group consisting of

OH hydroxyl and

O—PO$_3$H$_2$ monophosphate, and wherein Z is a nucleobase selected from the group consisting of adenine, guanine, thymine, cytosine, uracil and hypoxanthine, and wherein W is selected from the group consisting of hydrogen (—H) and hydroxyl (OH)

into the corresponding 3-hydroxycarboxyl-nucleotidylate of the following general formula III:

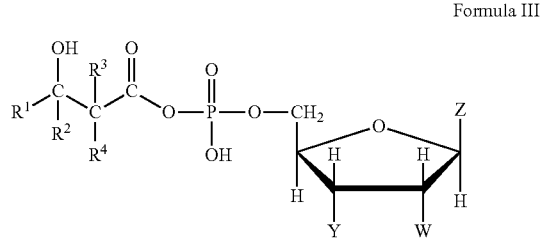

Formula III in which $R^1$, $R^2$, $R^3$ and $R^4$ have the same meaning as specified above in connection with formula I and wherein W, Y and Z have the same meaning as specified above in connection with formula II.

According to a method of the present invention the thus produced 3-hydroxycarboxyl-nucleotidylate is further converted into an alkene.

The alkene produced by the method according to the present invention is a molecule which responds to the following general formula IV:

Formula IV in which $R^1$, $R^2$, $R^3$ and $R^4$ have the same meaning as specified above in connection with formula I.

In preferred embodiments the 3-hydroxycarboxylate which is converted in the method according to the invention is selected from a 3-hydroxycarboxylate as specified in the following Table 1 and is converted into a corresponding alkene as indicated in Table 1.

TABLE 1

| 3-hydroxycarboxylic acid | | Corresponding alkene | |
| --- | --- | --- | --- |
| name | formula | name | formula |
| 3-hydroxypropionate | ![OH-CH(H)-CH(H)-CO2H] | ethylene | H$_2$C=CH$_2$ |
| 3-hydroxybutyrate | ![H3C-CH(OH)-CH(H)(H)-CO2H] | propylene | H$_3$C-CH=CH$_2$ |
| 2-methyl-3-hydroxypropionate | ![HO-CH(H)-C(CH3)(H)-CO2H] | propylene | H$_3$C-CH=CH$_2$ |
| 3-hydroxypentanoate | ![H3C-CH2-CH(OH)-CH(H)-CO2H] | but-1-ene | H$_3$C-CH$_2$-CH=CH$_2$ |

TABLE 1-continued

| 3-hydroxycarboxylic acid | | Corresponding alkene | |
|---|---|---|---|
| name | formula | name | formula |
| 2-(hydroxymethyl)butyrate | [structure] | but-1-ene | [structure] |
| 2-methyl-3-hydroxybutyrate | [structure] | (Z) but-2-ene | [structure] |
| 2-methyl-3-hydroxybutyrate | [structure] | (E) but-2-ene | [structure] |
| 3-hydroxy-3-methylbutyrate | [structure] | 2-methylpropylene aka isobutene | [structure] |
| 2,2-dimethyl-3-hydroxypropionate | [structure] | 2-methylpropylene aka isobutene | [structure] |
| 2-methyl-3-hydroxypentanoate | [structure] | (Z) pent-2-ene aka (Z) 2-amylene | [structure] |
| 2-ethyl-3-hydroxybutyrate | [structure] | (Z) pent-2-ene aka (Z) 2-amylene | [structure] |
| 2-methyl-3-hydroxypentanoate | [structure] | (E) pent-2-ene aka (E) 2-amylene | [structure] |
| 2-ethyl-3-hydroxybutyrate | [structure] | (E) pent-2-ene aka (E) 2-amylene | [structure] |
| 2,3-dimethyl-3-hydroxybutyrate | [structure] | 2-methylbut-2-ene aka isoamylene | [structure] |

TABLE 1-continued

| 3-hydroxycarboxylic acid | | Corresponding alkene | |
|---|---|---|---|
| name | formula | name | formula |
| 2,2-dimethyl-3-hydroxybutyrate | [structure] | 2-methylbut-2-ene aka isoamylene | [structure] |
| 3-methyl-3-hydroxypentanoate | [structure] | 2-methylbut-1-ene | [structure] |
| 2-methyl-2-(hydroxymethyl)butyrate | [structure] | 2-methylbut-1-ene | [structure] |
| 4-methyl-3-hydroxypentanoate | [structure] | 3-methylbut-1-ene | [structure] |
| 2-(hydroxymethyl)-3-methylbutyrate | [structure] | 3-methylbut-1-ene | [structure] |
| 3-hydroxypent-4-enoate | [structure] | 1,3-butadiene | [structure] |
| 2-(hydroxymethyl)but-3-enoate | [structure] | 1,3-butadiene | [structure] |
| 3-hydroxy-4-methylpent-4-enoate | [structure] | 2-methyl-1,3-butadiene aka isoprene | [structure] |
| 3-hydroxy-3-methylpent-4-enoate | [structure] | 2-methyl-1,3-butadiene aka isoprene | [structure] |
| 2-(hydroxymethyl)-2-methylbut-3-enoate | [structure] | 2-methyl-1,3-butadiene aka isoprene | [structure] |

TABLE 1-continued

| 3-hydroxycarboxylic acid | | Corresponding alkene | |
|---|---|---|---|
| name | formula | name | formula |
| 2-(hydroxymethyl)-3-methylbut-3-enoate | 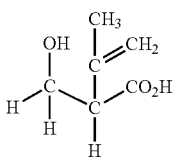 | 2-methyl-1,3-butadiene aka isoprene | 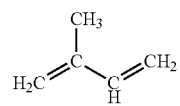 |

As described above, according to the method of the invention a 3-hydroxycarboxylate is first converted into a 3-hydroxycarboxyl-nucleotidylate. This is achieved by a nucleotidylation reaction, i.e. a reaction in which a nucleotidyl group is transferred from the co-substrate (Formula II) to the carboxyl group of the 3-hydroxycarboxylate. The general reaction is shown in FIG. 1.

Examples for the co-substrate according to formula II are ribonucleotides, such as ATP, CTP, GTP, UTP and ITP, with ATP being preferred, and ADP, CDP, GCP UDP and IDP, with ADP being preferred. Other examples are desoxyribonucleotides, such as dATP, dCTP, dGTP, dTTP and dITP. Further examples are 3'-phosphoadenosin-5'-phosphosulfate (PAPS) or adenosin-5'-phosphosulfate (APS).

In a preferred embodiment, Z is adenine. In another preferred embodiment, Z is adenine and W is H. In a further preferred embodiment, Z is adenine, W is H and X is monophosphate or diphosphate. In another preferred embodiment, Z is adenine, W is H, X is sulfate and Y is OH or monophosphate. In another particularly preferred embodiment Z is adenine, W and Y are OH. In another preferred embodiment Z is adenine, W is H and Y is OH. In a further preferred embodiment Z is adenine, W and Y are OH and X is monophosphate or diphosphate. In another preferred embodiment, Z is adenine, W is OH, X is sulfate, Y is OH or monophosphate.

In a preferred embodiment, the conversion of the 3-hydroxycarboxylate in the first step of the method according to the invention leads to a 3-hydroxycarbonyl-adenylate.

Figure 2A:
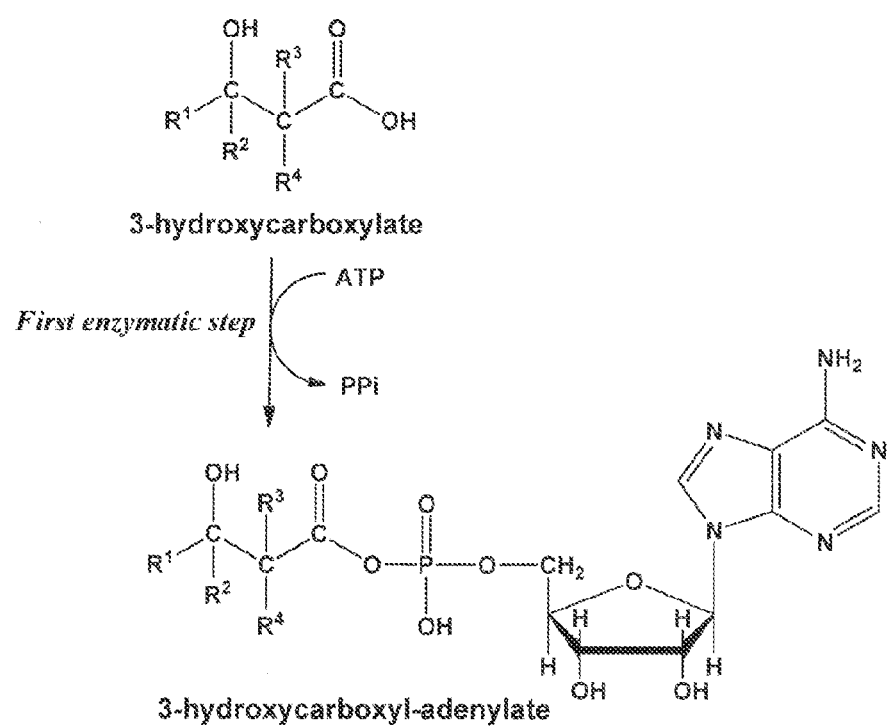
Figure 2B:
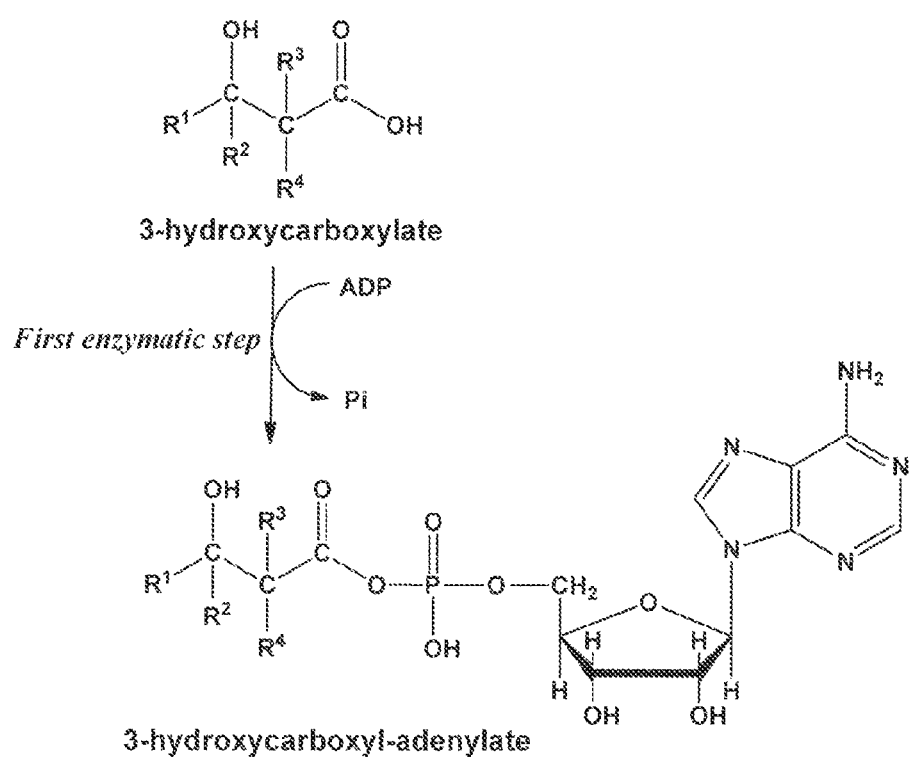
Figure 3:
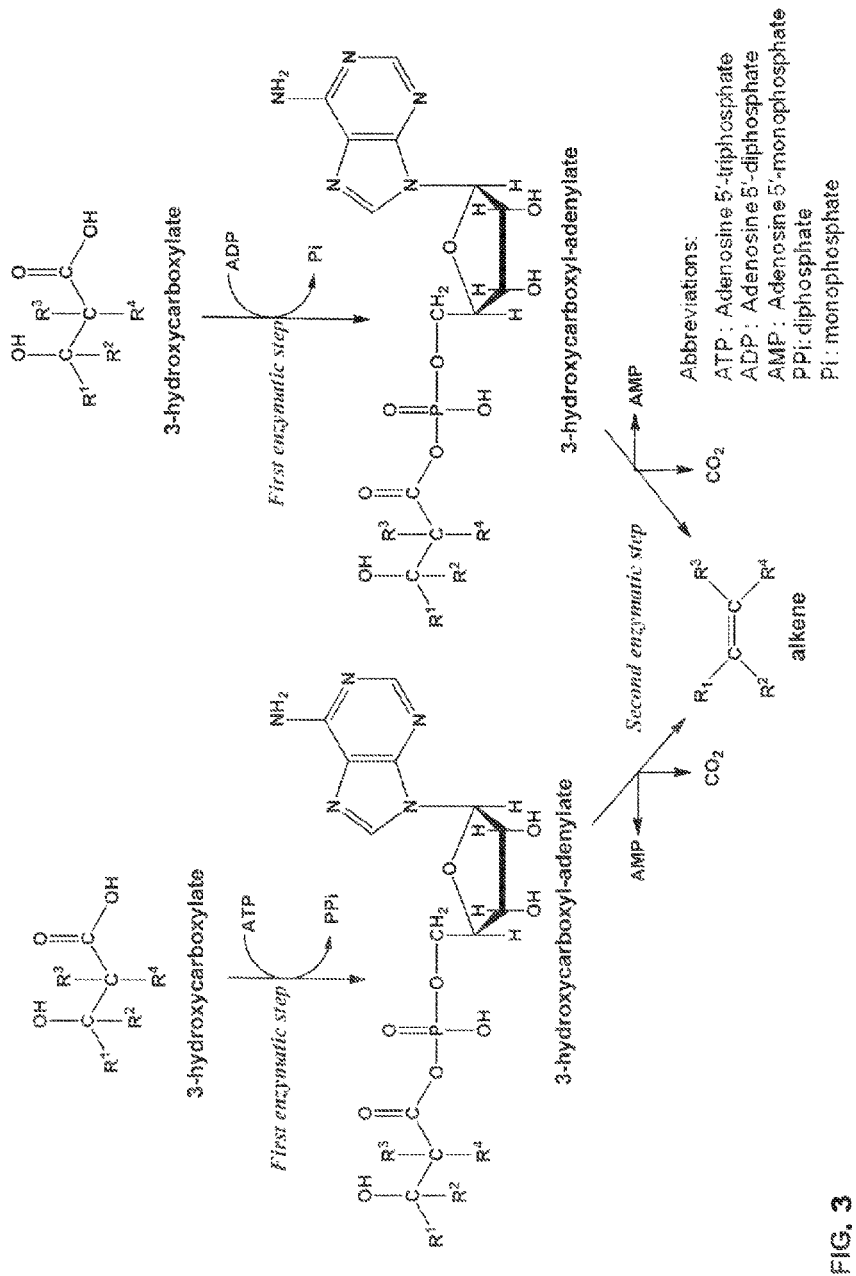

In one preferred embodiment, the co-substrate of the formula II is ATP or ADP and the first enzymatic conversion is an adenylation. The reaction is schematically shown in FIG. 2. The scheme for the overall reaction leading to the alkene is shown in FIG. 3.

The conversion of the 3-hydroxycarboxylate into the 3-hydroxycarboxyl-nucleotidylate according to the method of the present invention can preferably be achieved by an enzymatic reaction, in particular by the use of an enzyme which catalyzes the transfer of a nucleotidyl group onto a molecule.

In one embodiment of the method according to the invention enzymes which are classified as an "adenylate forming enzyme" are used for the conversion of the 3-hydroxycarboxylate into a 3-hydroxycarboxyl-nucleotidylate. The term "adenylate forming enzyme" is understood to mean an enzyme which is capable of catalysing the following reaction:

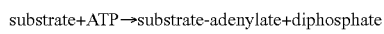

(see, e.g., Schmelz and Naismith (Curr. Opin. Struc. Biol. 19 (2009), 666-671; Linne et al., FEBS Letters 581 (2007), 905-910). Although ATP is indicated as the co-substrate, it is known that adenylate-forming enzymes can use other co-substrates such as ADP, UTP, CTP, GTP and ITP. Thus, in the scope of the present invention the term "adenylate-forming" is not limiting in the sense that the enzymes only produce an adenylated product, but is only used as the established term used in the art but also covers the possibility that the respective enzymes can use other co-substrates as defined in Formula II. Preferably the group on the substrate to which the nucleotidyl moiety is transferred is a carboxylic group. As described in Schmelz and Naismith (loc. cit.) adenylating enzymes activate the otherwise unreactive carboxylic acid by transforming the normal hydroxyl leaving group into adenosine monophosphate. These enzymes share the following common structural features referenced in different databases:

1. InterPro database (InterPro44.0; Release Sep. 25, 2013)
   IPR020845, AMP-binding, conserved site (http://www.ebi.ac.uk/interpro/entry/IPR020845)
   IPR000873 (http://www.ebi.ac.uk/interpro/entry/IPR000873)
2. Prosite
   PS00455 (http://prosite.expasy.org/PS00455)
   Description: Putative AMP-binding domain signature.
   Pattern: [LIVMFY]-{E}-{VES}-[STG]-[STAG]-G-[ST]-[STEI]-[SG]-x-[PASLIVM]-[KR].
   (Entry name AMP_BINDING; Accession number PS00455; Entry type PATTERN; Date May 1991 (CREATED); December 2004 (DATA UPDATE); October 2013 (INFO UPDATE). Pattern [LIVMFY]-{E}-{VES}-[STG]-[STAG]-G-[ST]-[STEI]-[SG]-x-[PASLIVM]-[KR])
3. Pfam
   The accession number for these enzymes in the Pfam database is PF00501.

Adenylate forming enzymes are, e.g., described in Schmelz and Naismith (Curr. Opin. Struc. Biol. 19 (2009), 666-671). Based on sequence analysis a superfamily of adenylate forming enzymes has been identified which can be subdivided into three closely related sub-families.

The first sub-family (referred to as Class I) comprises the following sub-classes:
  the adenylation domains of non-ribosomal peptide synthetases (NRPS);
  the acyl- or aryl-CoA synthetases;
  the (luciferase) oxidoreductases; and
  the adenylation domain of polyketide synthase (PKS).
Also the AMP-dependent synthetases and ligases described herein further below can be classified into this class.

The second sub-family (referred to as Class II) comprises:
  the aminoacyl-tRNA synthetases.

The third sub-family (referred to as Class III) comprises:
  the NIS enzymes.
  NIS enzymes are enzymes involved in the NRPS-independent siderophores (NIS) synthesis.

In a preferred embodiment the method according to the present invention employs an enzyme which belongs to the above, mentioned Class I.

In one embodiment the enzyme belongs to Class I and to the subclass comprising the adenylation domains of non-ribosomal peptide synthetases (NRPS) (Marahiel, Chem. Rev. 97 (1997), 2651-2673; Sundlov et al., Chem Biol. 19 (2012), 188-198; Sundlov et al., Acta Cryst. D69 (2013). 1482-1492; May et al., PNAS 99 (2002), 12120-12125; Keating, Biochemistry 39 (2000), 4729-4739).

In another embodiment the enzyme belongs to Class I and to the subclass comprising the acyl- or aryl-CoA synthetases (Soupene and Kuypers, Exp Biol Med 233 (2008), 507-521; Mashek et al., Future Lipidol. 2 (2007), 465-476; Ehlting et al., The Plant Journal 27(2001), 455-465).

In another embodiment the enzyme belongs to Class I and to the subclass comprising the (luciferase) oxidoreductases. One representative example of such an enzyme and a preferred enzyme to be used in a method according to the present invention is the firefly luciferase (Oba et al., FEBS Letters 540 (2003), 251-254).

In another embodiment the enzyme belongs to Class I of adenylate forming enzymes and to the subclass comprising the adenylation domain of a polyketide synthase (PKS). A representative example of this group of enzymes is the polyketide-peptide synthase of *Xanthomonas albilineans* (Huang et al., Microbiology 147 (2001), 631-642).

Enzymes which belong to the above mentioned Class I of adenylate forming enzymes are classified in the EC 6.2.1 superfamily. In principle any enzyme classified as EC 6.2.1 can be employed in a method according to the present invention. Examples for such adenylate forming enzymes are:

EC 6.2.1.1 acetate:CoA ligase (AMP forming);
EC 6.2.1.2 butanoate:CoA ligase (AMP forming);
EC 6.2.1.3 long-chain fatty acid:CoA ligase (AMP-forming);
EC 6.2.1.12 4-Coumarate-CoA ligase;
EC 6.2.1.20 long-chain-fatty-acid:[acyl-carrier protein] ligase (AMP-forming);
EC 6.2.1.33 4-chlorobenzoate:CoA ligase; and
EC 6.2.1.36 3-hydroxypropionate:CoA ligase (AMP-forming).

All the enzymes of this group share common structural motifs which are referenced in the InterPro (InterPro44.0; Release Sep. 25, 2013) as InterPro IPR020845, AMP-binding, conserved site (http://www.ebi.ac.uk/interpro/entry/IPR020845) and IPR000873 (http://www.ebi.ac.uk/interpro/entry/IPR000873). The accession number for these enzymes in the Pfam database is PF00501.

Thus, in one preferred embodiment the enzymatic conversion of the 3-hydroxycarboxylate into a corresponding 3-hydroxycarboxyl-nucleotidylate can, e.g., be achieved by the use of an acetate:CoA ligase (AMP forming) (EC 6.2.1.1). Acetate:CoA ligases are enzymes which catalyze the following reaction:

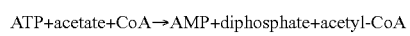
ATP+acetate+CoA→AMP+diphosphate+acetyl-CoA

The reaction is a two-step reaction which involves the formation of an acetyl-AMP intermediate from acetate and ATP and the transfer of the acetyl group to CoA. These enzymes are present in most living organisms from bacteria to humans.

The occurrence of these enzymes has been described for a large number of organisms, including prokaryotes and eukaryotes, in particular, bacteria, algae, fungi, plants and animals, e.g. for *S. cerevisiae, Moorella thermoacetica, Pyrococcus furiosus, Archaeoglobus fulgidus, Methanothermobacter thermoautotropicus, Methanosaeta concilii, Methanosarcina* sp., *Bacillus subtilis, Salmonella enteric, Aliivibrio fischeri, E. coli, Holoarcula marismortui, Bradyrhizobium japonicum, Oryctolagus cuniculus, Ovis aries, Penicillium chrysogenum, Phycomyces blakesleeanus, Cryptosporidium parvum, Emericella nidulans, Euglena gracilis, Pseudomonas aeruginosa, Pseudomonas putida, Pyrobaculum aerophilum, Rhodobacter sphaeroides, Roseovarius* sp., *Neurospora crassa, Pinus radiate, Spinacia oleracea, Taxus* sp., *Zea mays, Arabidopsis thaliana, Pisum sativum, Amaranthus* sp., *Hordeum vulgare, Rattus norvegicus, Mus musculus, Mormota monax, Bos taurus* and *Homo sapiens*. For the enzyme from *S. cerevisiae* the crystal structure has been disclosed e.g. in Jogl and Tong (Biochemistry 43 (2004), 1425-1431). In principle, any known acetate:CoA ligase can be employed in the method according to the invention. In one aspect of the present invention, an acetate:CoA ligase from *S. cerevisiae* is used (Jogl and Tong; loc. cit.).

In another preferred embodiment the enzymatic conversion of the 3-hydroxycarboxylate into a corresponding 3-hydroxycarboxyl-nucleotidylate can, e.g., be achieved by the use of a butanoate:CoA ligase (AMP forming) (EC 6.2.1.2). Butanoate:CoA ligases are enzymes which catalyze the following reaction:

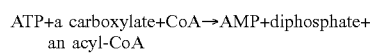
ATP+a carboxylate+CoA→AMP+diphosphate+ an acyl-CoA

These enzymes participate in butanoate metabolism. The occurrence of these enzymes has been described for a large number of organisms, including prokaryotes and eukaryotes, in particular, bacteria, algae, fungi, plants and animals, e.g. for *Streptomyces coelicolor, Mycobacterium avium, Penicillium chrysogenum, Paecilomyces variotii, Pseudomonas aeruginosa, Dictyostelium discoideum, Cavia porcellus, Ovis aries, Sus scrofa, Bos taurus, Mus musculus, Rattus norvegicus*, and *Homo sapiens*.

In another preferred embodiment the enzymatic conversion of the 3-hydroxycarboxylate into a corresponding 3-hydroxycarboxyl-nucleotidylate can, e.g., be achieved by the use of a long-chain fatty acid:CoA ligase (AMP-forming) (EC 6.2.1.3) (also known as fatty acyl-CoA synthetases; FACS). These enzymes catalyze the following reaction:

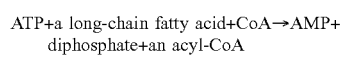
ATP+a long-chain fatty acid+CoA→AMP+ diphosphate+an acyl-CoA

One of the key features of this catalysis is the formation of an adenylated intermediate, i.e. fatty acyl-AMP. This activation step involves the linking of the carboxyl group of the fatty acid through an acyl bond to the phosphoryl group of AMP.

These enzymes play a central role in the intermediary metabolism by catalyzing the formation of fatty acyl-CoA. Accordingly, they occur basically in all organisms and have been described, e.g., for *S. cerevisiae, E. coli, Pseudomonas aeruginosa, Pseudomonas chlororaphis, Caulobacter vibrioides, Mycobacterium tuberculosis, Trypanosoma brucei, Emericella nidulans, Yarrowia lipolytica, Plasmodium falciparum, Plasmodium knowlesi, Ceanorhabditis elegans, Drosophila melanogaster, Mortierella alpina, Thalassiosira pseudonana, Photinus pyralis, Tribolium castaneum, Oryctolagus cuniculus, Komagataella pastoris, Luciola cruciata, Notothenia coriiceps, Pisum sativum, Zea mays, Arabidopsis thaliana, Ulmus* sp., *Brassica napus, Agrypnus binodulus, Bebesia bovis, Mus musculus, Rattus norvegicus, Sus scrofa* and *Homo sapiens*. In principle, any known long-chain fatty acid:CoA ligase can be employed in the method according to the invention. In one aspect of the present invention, a long-chain fatty acid:CoA ligase from *E. coli* is used. The enzyme in *E. coli* is encoded by the fadD gene (Weimar et al., J. Biol. Chem. 277 (2002), 29369-29376).

In another preferred embodiment the enzymatic conversion of the 3-hydroxycarboxylate into a corresponding 3-hydroxycarboxyl-nucleotidylate can, e.g., be achieved by the use of a 4-coumarate-CoA ligase (EC 6.2.1.12). 4-coumarate-CoA ligases are enzymes which catalyze the following reaction:

ATP+4-coumarate+CoA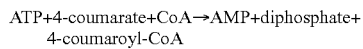AMP+diphosphate+
4-coumaroyl-CoA 4-coumarate-CoA ligases catalyze the formation of CoA thiol esters of 4-coumarate and other hydroxycinnamates in a two step reaction involving the formation of an adenylate intermediate. These enzymes are involved in phenylpropanoid biosynthesis. The occurrence of these enzymes has been described for a large number of organisms, in particular eukaryotes, and in particular fungi and plants, e.g. for *S. cerevisiae, Fragaria×ananassa, Oryza sativa, Lithospermum erythrorhizon, Eriobotrya japonica, Arabidopsis thaliana Physcomitrella patens, Ruta graveolens, Robinis pseudoacacia, Nicotiana tabacum, Vitis vinifera, Larix cajanderi, Larix gmelinii, Larix kaempferi, Larix kamtschatica, Larix sibirica, Larix, sukaczewii, Cocos nucifera, Pinus radiate, Camellia sinensis, Centaureum erythraea, Cephalocereus senilis, Forsythia suspensa, Glycine max, Gossypium hirsutum, Lolium perenne, Nicotiana tabacum, Metasequoia glyptostroboides, Paulownia tomentosa, Petroselinum crispum, Phyllostacchus bambusoides, Picea abies, Pinus taesa, Pisum sativum, Platycladus orientalis, Polysporus hispidus, Populus tomentosa, Populus tremuloides, Populus trichocarpa, Populus Canadensis, Prunus avium, Solanum tuberosum, Salix babylonica, Triticum* and *aestivum*. In principle, any known 4-coumarate-CoA ligase can be employed in the method according to the invention. In one embodiment the 4-coumarate-CoA ligase from *A. thaliana* is employed (Ehlting et al., Plant J. 27 (2001), 455-465).

In another preferred embodiment the enzymatic conversion of the 3-hydroxycarboxylate into a corresponding 3-hydroxycarboxyl-nucleotidylate can, e.g., be achieved by the use of a long-chain fatty acid:[acyl-carrier protein] ligase (AMP-forming) (EC 6.2.1.20). These enzymes catalyze the following reaction:

ATP+an acid+[acyl-carrier protein]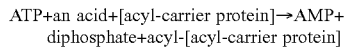AMP+
diphosphate+acyl-[acyl-carrier protein]

One of the key features of this catalysis is the formation of an adenylated intermediate, i.e. acyl-AMP. This activation step involves the linking of the carboxyl group of the acid through an acyl bond to the phosphoryl group of AMP.

These enzymes are involved in the fatty acid metabolism and they occur in various organisms. They have been described, e.g., for *Vibrio harveyi, Plasmodium falciparum, E. coli, Synechococcus elongates, Synechococcus sp., Rhodotorula glutinis, Arabidopsis thaliana* and *Allium ampeloprasum*. In *Vibrio harveyi* the enzyme is encoded by the aasS gene (Jiang et al., Biochemistry 45 (2006), 10008-10019). In principle, any known long-chain fatty acid:[acyl-carrier protein] ligase can be employed in the method according to the invention. In one embodiment the long-chain fatty acid: [acyl-carrier protein] ligase from *Vibrio harveyi* is employed.

In another preferred embodiment the enzymatic conversion of the 3-hydroxycarboxylate into a corresponding 3-hydroxycarboxyl-nucleotidylate can, e.g., be achieved by the use of a 4-chlorobenzoate:CoA ligase (AMP forming) (EC 6.2.1.33). 4-chlorobenzoate:CoA ligases are enzymes which catalyze the following reaction:

ATP+4-chlorobenzoate+CoA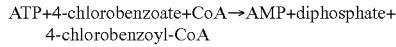AMP+diphosphate+
4-chlorobenzoyl-CoA

These enzymes participate in the degradation of 2,4-dichlorobenzoate. They catalyze 4-chlorobenzoyl-CoA formation in a two-step reaction consisting of the adenylation of 4-chlorobenzoate with ATP followed by acyl transfer from the 4-chlorobenzoyl-AMP intermediate to CoA. The occurrence of these enzymes has been described e.g. for bacteria of the geni *Alcaligenes, Pseudomonas* and *Arthrobacter*. The enzyme from *Pseudomonas* sp. strain CBS3 is, e.g., described in Chang et al. (Biochemistry 36 (1997), 15650-15659).

In another preferred embodiment the enzymatic conversion of the 3-hydroxycarboxylate into a corresponding 3-hydroxycarboxyl-nucleotidylate can, e.g., be achieved by the use of a 3-hydroxypropionate:CoA ligase (AMP forming) (EC 6.2.1.36). 3-hydroxypropionate:CoA ligases are enzymes which catalyze the following reaction:

ATP+3-hydroxypropionate+CoA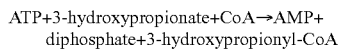AMP+
diphosphate+3-hydroxypropionyl-CoA

These enzymes catalyze a step in the 3-hydroxypropionate/4-hydroxybutyrate cycle. The occurrence of these enzymes has been described, e.g., for bacteria, in particular for *Sulfolobus tokodaii* and *Metallosphaera sedula* (Alber et al., J. Bacteriol. 190 (2008), 1383-1389). The enzyme from *Pseudomonas* sp. strain CBS3 is, e.g., described in Chang et al. (Biochemistry 36 (1997), 15650-15659). It is described in Chang et al. that the enzyme also activates propionate, acrylate, acetate and butyrate.

In a further preferred embodiment the enzymatic conversion of the 3-hydroxycarboxylate into a corresponding 3-hydroxycarboxyl-nucleotidylate can, e.g., be achieved by the use of the acyl-CoA synthetase from *Marinobacter algicola* showing the amino acid sequence shown in SEQ ID NO: 2 (see also Uniprot accession number A6EZ54). It is of course not only possible to use an enzyme having the amino acid sequence as shown in SEQ ID NO:2 but also enzymes with related sequences which show the activity of an acyl-CoA synthetase. Thus, in one preferred embodiment the method according to the present invention makes use of an acyl-CoA synthetase comprising the amino acid sequence shown in SEQ ID NO: 2 or a sequence which is at least x % identical to SEQ ID NO: 2 and which shows the activity of an acyl-CoA synthetase and can convert a 3-hydroxycarboxylate into a 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The appended Examples demonstrate that this enzyme is capable of converting, e.g., 3-hydroxypropionate and ATP, 3-hydroxyvalerate and ATP, 3-hydroxypent-4-enoate and ATP, 3-hydroxyisovalerate and ATP and 3-hydroxybutyrate and ATP into the corresponding 3-hydroxycarboxyl-nucleotidylates. It is also shown in the Examples that this enzyme can use ATP or ADP as a co-substrate.

In another preferred embodiment the enzymatic conversion of the 3-hydroxycarboxylate into a corresponding 3-hydroxycarboxyl-nucleotidylate can, e.g., be achieved by the use of the acyl-CoA synthetase from *Marinobacter manganoxidans* showing the amino acid sequence shown in SEQ ID NO: 3 (see also Uniprot accession number G6YPQ6). It is of course not only possible to use an enzyme having the amino acid sequence as shown in SEQ ID NO:3 but also enzymes with related sequences which show the activity of an acyl-CoA synthetase. Thus, in one preferred embodiment the method according to the present invention makes use of an acyl-CoA synthetase comprising the amino acid sequence shown in SEQ ID NO: 3 or a sequence which is at least x % identical to SEQ ID NO: 3 and which shows the activity of an acyl-CoA synthetase and can convert a 3-hydroxycarboxylate into 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

In a further preferred embodiment the enzymatic conversion of the 3-hydroxycarboxylate into a corresponding 3-hydroxycarboxyl-nucleotidylate can, e.g., be achieved by the use of an AMP-dependent synthetase and ligase. AMP-dependent synthetase and ligases share the common structural motifs which are referenced in the InterPro (InterPro44.0; Release Sep. 25, 2013) as InterPro IPR020845, AMP-binding, conserved site (http://www.ebi.ac.uk/interpro/entry/IPR020845) and IPR000873 (http://www.ebi.ac.uk/interpro/entry/IPR000873). In principle any AMP-dependent synthetase and ligase can be employed in a method according to the present invention.

In one preferred embodiment the AMP-dependent synthetase and ligase is an AMP-dependent synthetase and ligase of *Marinobacter aquaeolei* showing the amino acid sequence shown in SEQ ID NO:1 (see also Uniprot accession number A1U2F4). It is of course not only possible to use an enzyme having the amino acid sequence as shown in SEQ ID NO:1 but also enzymes with related sequences which show the activity of an AMP-dependent synthetase and ligase. Thus, in one preferred embodiment the method according to the present invention makes use of an AMP-dependent synthetase and ligase comprising the amino acid sequence shown in SEQ ID NO: 1 or a sequence which is at least x % identical to SEQ ID NO: 1 and which shows the activity of an AMP-dependent synthetase and ligase and can convert a 3-hydroxycarboxylate into 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The appended Examples demonstrate that this enzyme is capable of converting, e.g., 3-hydroxypropionate and ATP, 3-hydroxyvalerate and ATP, 3-hydroxypent-4-enoate and ATP, 3-hydroxyisovalerate and ATP and 3-hydroxybutyrate and ATP into the corresponding 3-hydroxycarboxyl-nucleotidylates. It is also shown that the corresponding 3-hydroxycarboxyl-nucleotidylate can be further converted into the corresponding alkene when the enzyme is used in combination with an OleC protein as described further below, preferably the OleC protein from *Shewanella amazonensis*, from *Xanthomonas campestris* or from *Chloroflexus aurantiacus*. This is, e.g., shown for the production of propylene from 3-hydroxybutyrate or for the production of 1-butene from 3-hydroxyvalerate or for the production of 1,3-butadiene from 3-hydroxypent-4-enoate or for the production of isobutene from 3-hydroxyisovalerate. Thus, in a preferred embodiment the method according to the present invention makes use of an AMP-dependent synthetase and ligase of *Marinobacter aquaeolei* as described herein-above and an OleC protein from *Shewanella amazonensis*, from *Xanthomonas campestris*, from *Stenotrophomonas maltophilia* or from *Chloroflexus aurantiacus* as described herein-below. More preferably, such a method is for producing propylene from 3-hydroxybutyrate or for producing 1-butene from 3-hydroxyvalerate or for producing 1,3-butadiene from 3-hydroxypent-4-enoate or for the production of isobutene from 3-hydroxyisovalerate.

In a further preferred embodiment the enzymatic conversion of the 3-hydroxycarboxylate into a corresponding 3-hydroxycarboxyl-nucleotidylate can, e.g., be achieved by the use of an AMP-dependent synthetase and ligase such as the AMP-dependent synthetase and ligase of *Burkholderia* sp. showing the amino acid sequence shown in SEQ ID NO: 4 (see also Uniprot accession number R4WRJ4). It is of course not only possible to use an enzyme having the amino acid sequence as shown in SEQ ID NO:4 or but also enzymes with related sequences which show the activity of an AMP-dependent synthetase and ligase. Thus, in one preferred embodiment the method according to the present invention makes use of an AMP-dependent synthetase and ligase comprising the amino acid sequence shown in SEQ ID NO: 4 or a sequence which is at least x % identical to SEQ ID NO: 4 and which shows the activity of an AMP-dependent synthetase and ligase and can convert a 3-hydroxycarboxylate into 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The appended Examples demonstrate that this enzyme is capable of converting, e.g., 3-hydroxypropionate and ATP, 3-hydroxyvalerate and ATP, 3-hydroxypent-4-enoate and ATP, 3-hydroxyisovalerate and ATP and 3-hydroxybutyrate and ATP into the corresponding 3-hydroxycarboxyl-nucleotidylates. It is also shown in the Examples that this enzyme can use ATP or ADP as a co-substrate. It is furthermore shown that the corresponding 3-hydroxycarboxyl-nucleotidylate can be further converted into the corresponding alkene when the enzyme is used in combination with an OleC protein as described further below, preferably the OleC protein from *Shewanella amazonensis* or from *Shewanella loihica*. This is, e.g., shown for the production of propylene from 3-hydroxybutyrate or of 1-butene from 3-hydroxyvalerate or of 1,3-butadiene from 3-hydroxypent-4-enoate. Thus, in a preferred embodiment the method according to the present invention makes use of an AMP-dependent synthetase and ligase of *Burkholderia* sp. as described herein-above and an OleC protein from *Shewanella amazonensis* or from *Shewanella loihica* as described herein-below. More preferably, such a method is for producing propylene from 3-hydroxybutyrate or for the production of 1-butene from 3-hydroxyvalerate or for the production of 1,3-butadiene from 3-hydroxypent-4-enoate.

In a further preferred embodiment the enzymatic conversion of the 3-hydroxycarboxylate into a corresponding 3-hydroxycarboxyl-nucleotidylate can, e.g., be achieved by the use of an AMP-dependent synthetase and ligase such as the AMP-dependent synthetase and ligase of *Pseudomonas putida* showing the amino acid sequence shown in SEQ ID NO: 5 (see also Uniprot accession number A5W2K0). It is of course not only possible to use an enzyme having the amino acid sequence as shown in SEQ ID NO: 5 but also enzymes with related sequences which show the activity of an AMP-dependent synthetase and ligase. Thus, in one preferred embodiment the method according to the present invention makes use of an AMP-dependent synthetase and ligase comprising the amino acid sequence shown in SEQ ID NO: 5 or a sequence which is at least x % identical to SEQ ID NO: 5 and which shows the activity of an AMP-dependent synthetase and ligase and can convert a 3-hydroxycarboxylate into 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The appended Examples demonstrate that this enzyme is capable of converting, e.g., 3-hydroxypropionate and ATP, 3-hydroxyvalerate and ATP, 3-hydroxypent-4-enoate and ATP, 3-hydroxyisovalerate and ATP and 3-hydroxybutyrate and ATP into the corresponding 3-hydroxycarboxyl-nucleotidylates.

In a further preferred embodiment the enzymatic conversion of the 3-hydroxycarboxylate into a corresponding 3-hydroxycarboxyl-nucleotidylate can, e.g., be achieved by the use of a medium-chain-fatty-acid-CoA ligase such as the medium-chain-fatty-acid-CoA ligase of *Pseudomonas oleovorans* showing the amino acid sequence shown in SEQ ID NO: 6 (see also van Beilen et al., Mol. Biol. 6 (1992), 3121-3136 and Uniprot accession number Q00594). It is of course not only possible to use an enzyme having the amino acid sequence as shown in SEQ ID NO: 6 but also enzymes with related sequences which show the activity of a medium-chain-fatty-acid-CoA ligase. Thus, in one preferred embodiment the method according to the present invention makes use of a medium-chain-fatty-acid-CoA ligase comprising the amino acid sequence shown in SEQ ID NO: 6 or a sequence which is at least x % identical to SEQ ID NO: 6 and which shows the activity of a medium-chain-fatty-acid-CoA ligase and can convert a 3-hydroxycarboxylate into 3-hydroxycarboxyl-nucleotidylate as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The appended Examples demonstrate that this enzyme is capable of converting, e.g., 3-hydroxypent-4-enoate and ATP into the corresponding 3-hydroxycarboxyl-nucleotidylate.

In another preferred embodiment the method according to the present invention employs an enzyme which belongs to the above mentioned Class II of adenylate forming enzymes. This class comprises the aminoacyl-tRNA synthetases. Enzymes belonging to this class are classified as EC 6.1.1. (Woese et al., Microbiology and Molecular Biology Reviews, 64 (2000), 202-236).

In another preferred embodiment the method according to the present invention employs an enzyme which belongs to the above mentioned Class III of adenylate forming enzymes. This class comprises NRPS-independent siderophore (NIS) adenylating enzymes (Challis, Chem. Bio. Chem, 6 (2005), 601-611).

In another embodiment of the method according to the invention enzymes which are classified as a "carboxylic acid reductases (CAR)" are used for the conversion of the 3-hydroxycarboxylate into a 3-hydroxycarboxyl-nucleotidylate.

The term "carboxylic acid reductases" is understood to mean an enzyme which is capable of catalysing the following reaction:

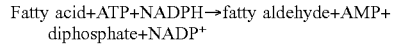
Fatty acid+ATP+NADPH→fatty aldehyde+AMP+ diphosphate+NADP⁺

The general function of these enzymes is, e.g., described in Akhtar et al. (PNAS 110 (2013), 87-92). These enzymes share the following common structural features referenced in different databases with the above-mentioned adenylate forming enzymes:

1. InterPro database (InterPro44.0; Release Sep. 25, 2013)
   IPR020845, AMP-binding, conserved site (http://www.ebi.ac.uk/interpro/entry/IPR020845)
   IPR000873 (http://www.ebi.ac.uk/interpro/entry/IPR000873)

2. Prosite
   PS00455 (http://prosite.expasy.org/PS00455)
   Description: Putative AMP-binding domain signature.
   Pattern: [LIVMFY]-{E}-{VES}-[STG]-[STAG]-G-[ST]-[STEI]-[SG]-x-[PASLIVM]-[KR].
   (Entry name AMP_BINDING; Accession number PS00455; Entry type PATTERN; Date May 1991 (CREATED); December 2004 (DATA UPDATE); October 2013 (INFO UPDATE). Pattern LIVMFY]-{E}-{VES}-[STG]-[STAG]-G-[ST]-[STEI]-[SG]-x-[PASLIVM]-[KR])

3. Pfam
   The accession number for these enzymes in the Pfam database is PF00501.

Moreover, the CAR enzymes can be classified as adenylate-forming enzymes since they catalyze in a first step a reaction which characterizes adenylate-forming enzymes, i.e. they activate the otherwise unreactive carboxylic acid of the fatty acid by transforming the normal hydroxyl leaving group into adenosine monophosphate. In particular, the reaction catalyzed by the CAR enzymes catalyze the overall reaction according to the following scheme:

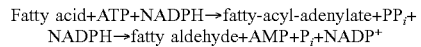
Fatty acid+ATP+NADPH→fatty-acyl-adenylate+PP$_i$+ NADPH→fatty aldehyde+AMP+P$_i$+NADP⁺

In one preferred embodiment, the carboxylic acid reductase is an enzyme which is classified in EC 1.2.99.6. In another preferred embodiment the NADPH-dependent carboxylic acid reductase is the carboxylic acid reductase from *Nocardia iowensis* showing the amino acid sequence shown in SEQ ID NO: 7. (Uniprot Q6RKB1; Venkitasubramanian et al., Enzyme and Microbial Technology 42 (2008), 130-137). It is of course not only possible to use an enzyme having the amino acid sequence as shown in SEQ ID NO: 7 but also enzymes with related sequences which show the activity of an NADPH-dependent carboxylic acid reductase. Thus, in one preferred embodiment the method according to the present invention makes use of an NADPH-dependent carboxylic acid reductase comprising the amino acid sequence shown in SEQ ID NO: 7 or a sequence which is at least x % identical to SEQ ID NO: 7 and which shows the activity of an NADPH-dependent carboxylic acid reductase and can convert a 3-hydroxycarboxylate into an alkene as described herein-above, with x being an integer between 25 and 100, preferably 30, 35, 40, 45, 50, 55, 60, 65, 70, 75, 80, 85, 90, 91, 92, 93, 94, 95, 96, 97, 98 or 99.

The Examples show the use of the NADPH-dependent carboxylic acid reductase from *Nocardia iowensis* (in combination with the OleC protein from *Shewanella amazonensis*) in the production of propylene from 3-hydroxybutyrate, of 1-butene from 3-hydroxyvalerate and of 1,3-butadiene from 3-hydroxypent-4-enoate. Thus, in a preferred embodiment the method according to the present invention is for the production of propylene from 3-hydroxybutyrate, of 1-butene from 3-hydroxyvalerate or of 1,3-butadiene from 3-hydroxypent-4-enoate and the enzymes employed are a carboxylic acid reductase, in particular an NADPH-dependent carboxylic acid reductase, most preferably the enzyme from *Nocardia iowensis* as described above in combination with an OleC protein as described further below, most preferably an OleC protein from *Shewanella amazonensis*.

As mentioned above, any co-substrate as shown in formula II can be employed in a method according to the present invention. Preferred are co-substrates in which Z is adenine and in particular the co-substrates ATP or ADP. However, in other embodiments the co-substrate can well be a co-substrate in which Z is another nucleobase, e.g., guanine, thymine, cytosine, uracil or hypoxanthine. It has been reported in Tanaka et al (Eur. J. Biochem. 98 (1979), 165-172) and in Alber et al. (J. Bacteriol. 190 (2007), 1383-1389) that adenylate forming enzymes are also able to use other co-substrates such as ADP, UTP, CTP, GTP and ITP apart from ATP.

Figure 4A:
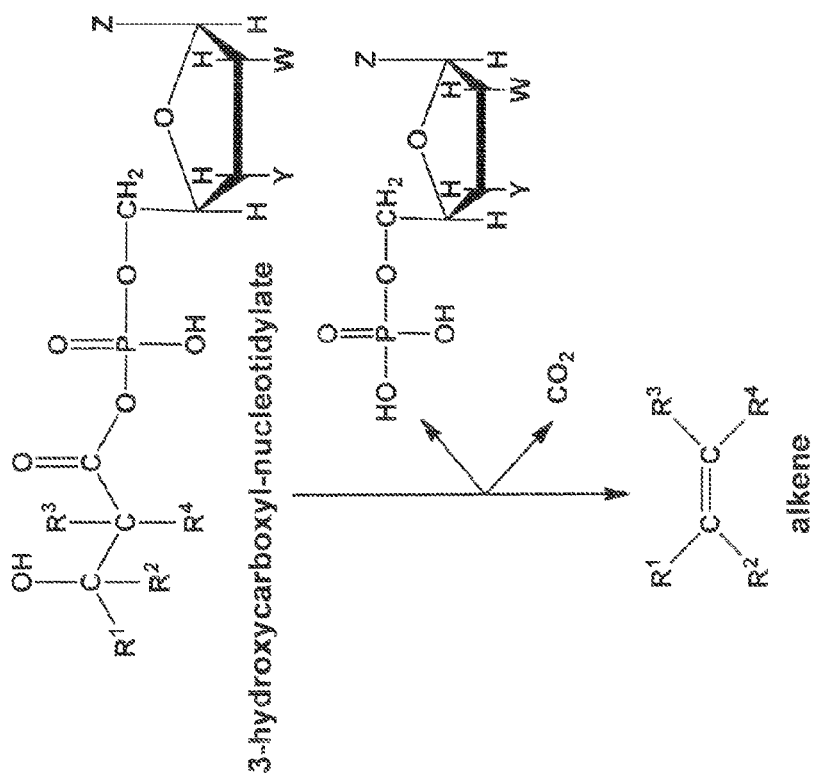

As described above, the obtained 3-hydroxycarboxyl-nucleotidylate is, according to the method of the present invention, further converted into a corresponding alkene. This conversion is achieved by an elimination of carbon dioxide, i.e. a decarboxylation reaction in which the nucleotide moiety and $CO_2$ are set free. The general scheme of this reaction is shown in FIG. 4A.

Figure 5:
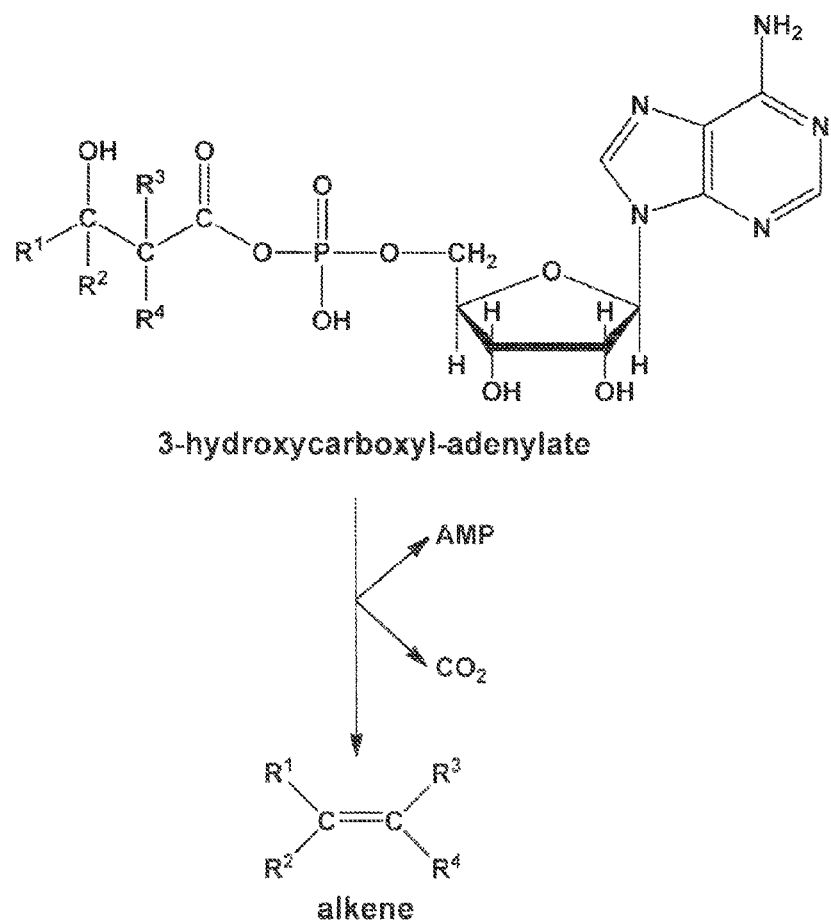

In particular, the conversion of the 3-hydroxycarboxyl-nucleotidylate into a corresponding alkene is achieved by an enzymatic decarboxylation, i.e. the decarboxylation is achieved by employing an enzyme. In a preferred embodiment, the 3-hydroxycarboxyl-nucleotidylate is a 3-hydroxycarbonyl-adenylate. The corresponding reaction scheme is shown in FIG. 5.

Suitable enzymes are in particular enzymes which are generally referred to as OleC-proteins.

In one preferred embodiment the enzyme employed in the first step of the method according to the present invention, i.e. the conversion of the 3-hydroxycarboxylate into a 3-hydroxycarboxyl-nucleotidylate, is different from the enzyme used in the second step of the method according to the present invention, i.e. the conversion of the 3-hydroxycarboxyl-nucleotidylate into the corresponding alkene. In particular, in one preferred embodiment the enzyme employed in the first step of the method according to the present invention, i.e. the conversion of the 3-hydroxycarboxylate into a 3-hydroxycarboxyl-nucleotidylate, is not an OleC protein as defined herein below.

The conversion of the 3-hydroxycarboxyl-nucleotidylate into the corresponding alkene can be achieved by a direct conversion of the 3-hydroxycarbonyl-nucleotidylate into the alkene. In the alternative, it is also possible that the 3-hydroxycarboxyl-nucleotidylate is first converted into a 3-hydroxynucleotydyl-carboxylate which is then further converted into the corresponding alkene (see FIG. 4B). It had been described in the Ph.D. thesis of Janice Alina Frias (2011; University of Minnesota, USA) that in particular OleC proteins probably catalyze a reaction in which a carboxyl-nucleotidylate is first converted into a nucleotydyl-carboxylate before being further converted.

Figure 29:
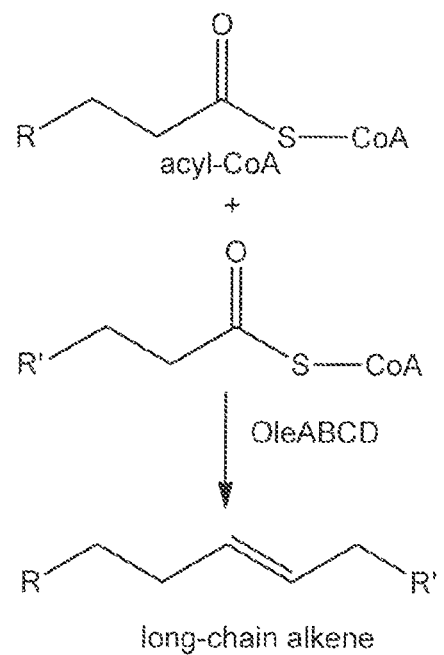

Thus, in a preferred embodiment, the enzyme employed in the second step of the method according to the present invention is an OleC protein. The OleC protein is a member of the AMP-dependent ligase/synthase superfamily (LuxE; acyl-adenylate/thioester-forming, acetyl-CoA synthetase-like (Sukovich et al., Appl. Environ. Microbiol. 76 (2010), 3850-3862)) and is known to be involved in polyolefinic hydrocarbon biosynthesis (Frias et al., Acta Cryst. F6 (2010), 1108-1110). Polyolefinic hydrocarbons were shown to be the product of a head-to-head fatty acid condensation biosynthetic pathway dependent on genes denoted as ole (olefin biosynthesis), in particular the ole ABCD gene cluster (Sukovich et al., Appl. Environ. Microbiol. 76 (2010), 3842-3849 and Sukovich et al., Appl. Environ. Microbiol. 76 (2010), 3850-3862). The general scheme of the reaction catalyzed by OleABCD is shown in FIG. 29. Wang and Lu (frontiers in Bioengineering and Biotechnology 1 (2013); Article 10) describe that a Claisen condensation of fatty acid derivatives is catalyzed by OleA to generate a β-ketoacid that can decarboxylate spontaneously to generate ketones. OleC is involved in a further reaction with the β-ketoacid intermediate generated by OleA (Frias et al., J. Biol. Chem. 286 (2011) 10930-10938; Sukovich et al., Appl. Environ. Microbiol. 76 (2010), 3842-3849).

Thus, the term "OleC protein" as used in the present invention refers to an AMP-dependent ligase/synthase. More preferably, it refers to an AMP-dependent ligase/synthase which can be allocated to the LuxE/AMP ligase family. The allocation to the LuxE/AMP ligase family is generally based on structural characteristics of the protein, for example its larger N-terminal domain sequence.

OleC proteins are structurally characterized by the feature that they have an AMP-binding domain. Preferably, the OleC protein shows an AMP-binding domain as defined in any of the following database entries:

1. InterPro database (InterPro44.0; Release Sep. 25, 2013)
   IPR020845, AMP-binding, conserved site (http://www.ebi.ac.uk/interpro/entry/IPR020845)
   IPR000873 (http://www.ebi.ac.uk/interpro/entry/IPR000873)
2. Prosite
   PS00455 (http://prosite.expasy.org/PS00455)
   Description: Putative AMP-binding domain signature.
   Pattern: [LIVMFY]-{E}-{VES}-[STG]-[STAG]-G-[ST]-[STEI]-[SG]-x-[PASLIVM]-[KR].
   (Entry name AMP_BINDING; Accession number PS00455; Entry type PATTERN; Date May 1991 (CREATED); December 2004 (DATA UPDATE); October 2013 (INFO UPDATE). Pattern [LIVMFY]-{E}-{VES}-[STG]-[STAG]-G-[ST]-[STEI]-[SG]-x-[PASLIVM]-[KR])
3. Pfam
   The accession number for these enzymes in the Pfam database is PF00501.

Moreover, the term "OleC protein" refers to a protein which is encoded by the ole ABCD gene cluster/operon.

Functionally, an OleC protein is characterized in that it is involved in polyolefinic hydrocarbon biosynthesis as described above, in particular in the biosynthesis of long chain olefins from alkyl-CoA (see FIG. 29).

Preferably the OleC protein is a protein which originates from an organism belonging to a genus selected from the group consisting of *Shewanella*, *Psychromonas*, *Stenotrophomonas*, *Xanthomonas* and *Chloroflexus*, more preferably from an organism belonging to a species selected from the group consisting of *Shewanella amazonensis*, *Shewanella loihica*, *Stenotrophomonas maltophilia*, *Xanthomonas campestris* and *Chloroflexus aurantiacus*. Even more preferably the organism is *Shewanella amazonensis* (strain ATCC BAA-1098/SB2B), *Shewanella loihica* (strain ATCC BAA-1088/PV-4), *Stenotrophomonas maltophilia* (strain R551-3), *Xanthomonas campestris* pv. *campestris* (strain ATCC 33913/NCPPB 528/LMG568) or *Chloroflexus aurantiacus* (strain ATCC 29364/DSM 6371Y-4-fl). In a particularly preferred embodiment the enzyme is an OleC enzyme the sequence of which is shown in Uniprot A1S4T5, Uniprot A3QDN4, Uniprot B4SSJ3, Uniprot Q8PDW6 and Uniprot B9LEI2.

In a preferred embodiment the enzymatic conversion of the 3-hydroxycarboxyl-nucleotidylate into a corresponding alkene can, e.g., be achieved by the use of an OleC protein of *Shewanella amazonensis* showing the amino acid sequence shown in SEQ ID NO: 8 (see also Uniprot accession number A1S4T5). It is of course not only possible to use an enzyme having the amino acid sequence as shown in SEQ ID NO:8 or but also enzymes with related sequences which show the activity of an OleC protein. Thus, in one preferred embodiment the method according to the present invention makes use of an OleC protein comprising the amino acid sequence shown in SEQ ID NO: 8 or a sequence which is at least x % identical to SEQ ID NO: 8 and which shows the activity of an OleC protein and can convert a 3-hydroxycarboxyl-nucleotidylate into an alkene as described herein-above, with x being an integer between 30 and 100, preferably 35, 40, 45, 50, 55, 60, 65, 70, 75, 80, 85, 90, 91, 92, 93, 94, 95, 96, 97, 98 or 99.

In a further preferred embodiment the enzymatic conversion of the 3-hydroxycarboxyl-nucleotidylate into a corresponding alkene can, e.g., be achieved by the use of an OleC protein of *Shewanella loihica* showing the amino acid sequence shown in SEQ ID NO: 9 (see also Uniprot accession number A3QDN4). It is of course not only possible to use an enzyme having the amino acid sequence as shown in SEQ ID NO:9 or but also enzymes with related sequences which show the activity of an OleC protein. Thus, in one preferred embodiment the method according to the present invention makes use of an OleC protein comprising the amino acid sequence shown in SEQ ID NO: 9 or a sequence which is at least x % identical to SEQ ID NO: 9 and which shows the activity of an OleC protein and can convert a 3-hydroxycarboxyl-nucleotidylate into an alkene as described herein-above, with x being an integer between 30 and 100, preferably 35, 40, 45, 50, 55, 60, 65, 70, 75, 80, 85, 90, 91, 92, 93, 94, 95, 96, 97, 98 or 99.

In a further preferred embodiment the enzymatic conversion of the 3-hydroxycarboxyl-nucleotidylate into a corresponding alkene can, e.g., be achieved by the use of an OleC protein of *Stenotrophomonas maltophilia* showing the amino acid sequence shown in SEQ ID NO: 10 (see also Uniprot accession number B4SSJ3). It is of course not only possible to use an enzyme having the amino acid sequence as shown in SEQ ID NO:10 or but also enzymes with related sequences which show the activity of an OleC protein. Thus, in one preferred embodiment the method according to the present invention makes use of an OleC protein comprising the amino acid sequence shown in SEQ ID NO: 10 or a sequence which is at least x % identical to SEQ ID NO: 10 and which shows the activity of an OleC protein and can convert a 3-hydroxycarboxyl-nucleotidylate into an alkene as described herein-above, with x being an integer between 30 and 100, preferably 35, 40, 45, 50, 55, 60, 65, 70, 75, 80, 85, 90, 91, 92, 93, 94, 95, 96, 97, 98 or 99.

In a further preferred embodiment the enzymatic conversion of the 3-hydroxycarboxyl-nucleotidylate into a corresponding alkene can, e.g., be achieved by the use of an OleC protein of *Xanthomonas campestris* showing the amino acid sequence shown in SEQ ID NO: 11 (see also Uniprot accession number Q8PDW6). It is of course not only possible to use an enzyme having the amino acid sequence as shown in SEQ ID NO:11 or but also enzymes with related sequences which show the activity of an OleC protein. Thus, in one preferred embodiment the method according to the present invention makes use of an OleC protein comprising the amino acid sequence shown in SEQ ID NO: 11 or a sequence which is at least x % identical to SEQ ID NO: 11 and which shows the activity of an OleC protein and can convert a 3-hydroxycarboxyl-nucleotidylate into an alkene as described herein-above, with x being an integer between 30 and 100, preferably 35, 40, 45, 50, 55, 60, 65, 70, 75, 80, 85, 90, 91, 92, 93, 94, 95, 96, 97, 98 or 99.

In a further preferred embodiment the enzymatic conversion of the 3-hydroxycarboxyl-nucleotidylate into a corresponding alkene can, e.g., be achieved by the use of an OleC protein of *Chloroflexus aurantiacus* showing the amino acid sequence shown in SEQ ID NO: 12 (see also Uniprot accession number B9LEl2). It is of course not only possible to use an enzyme having the amino acid sequence as shown in SEQ ID NO:12 or but also enzymes with related sequences which show the activity of an OleC protein. Thus, in one preferred embodiment the method according to the present invention makes use of an OleC protein comprising the amino acid sequence shown in SEQ ID NO: 12 or a sequence which is at least x % identical to SEQ ID NO: 12 and which shows the activity of an OleC protein and can convert a 3-hydroxycarboxyl-nucleotidylate into an alkene as described herein-above, with x being an integer between 30 and 100, preferably 35, 40, 45, 50, 55, 60, 65, 70, 75, 80, 85, 90, 91, 92, 93, 94, 95, 96, 97, 98 or 99.

Figure 6A:
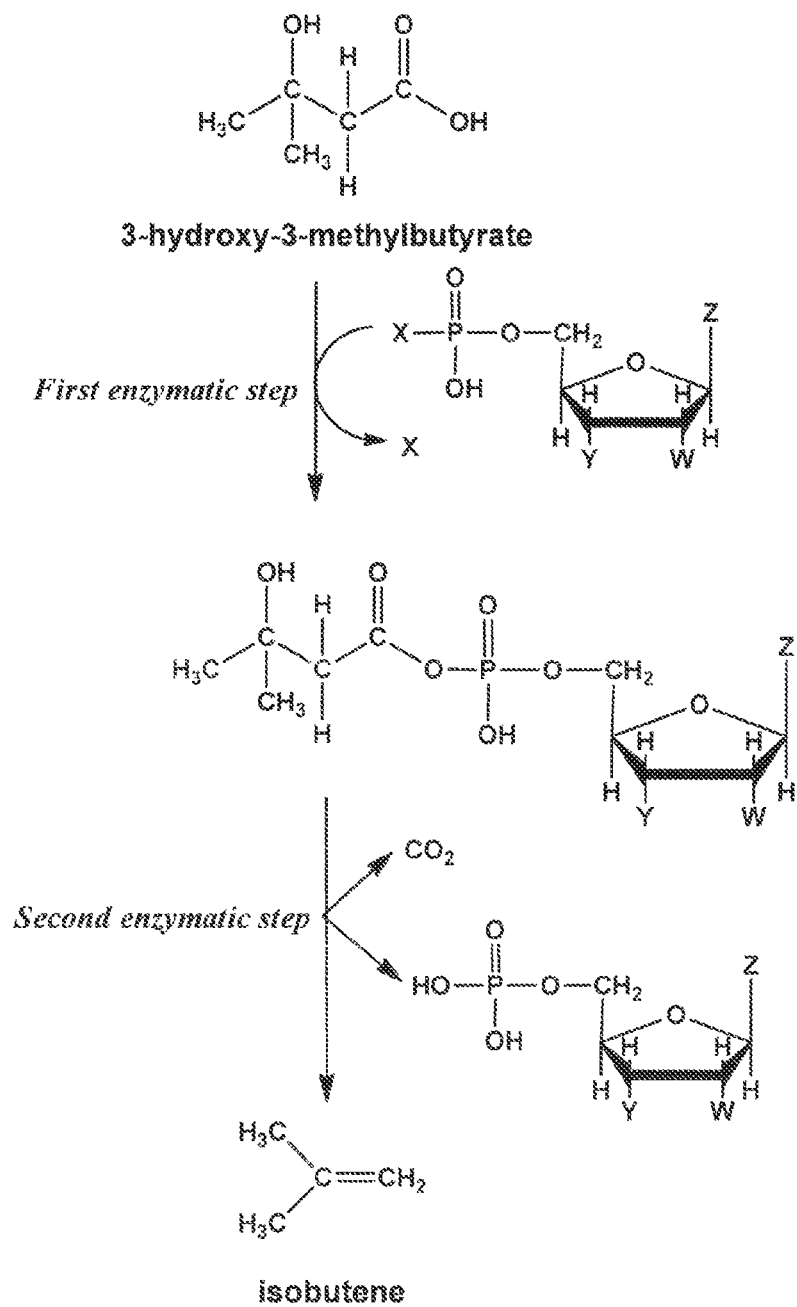
Figure 6B:
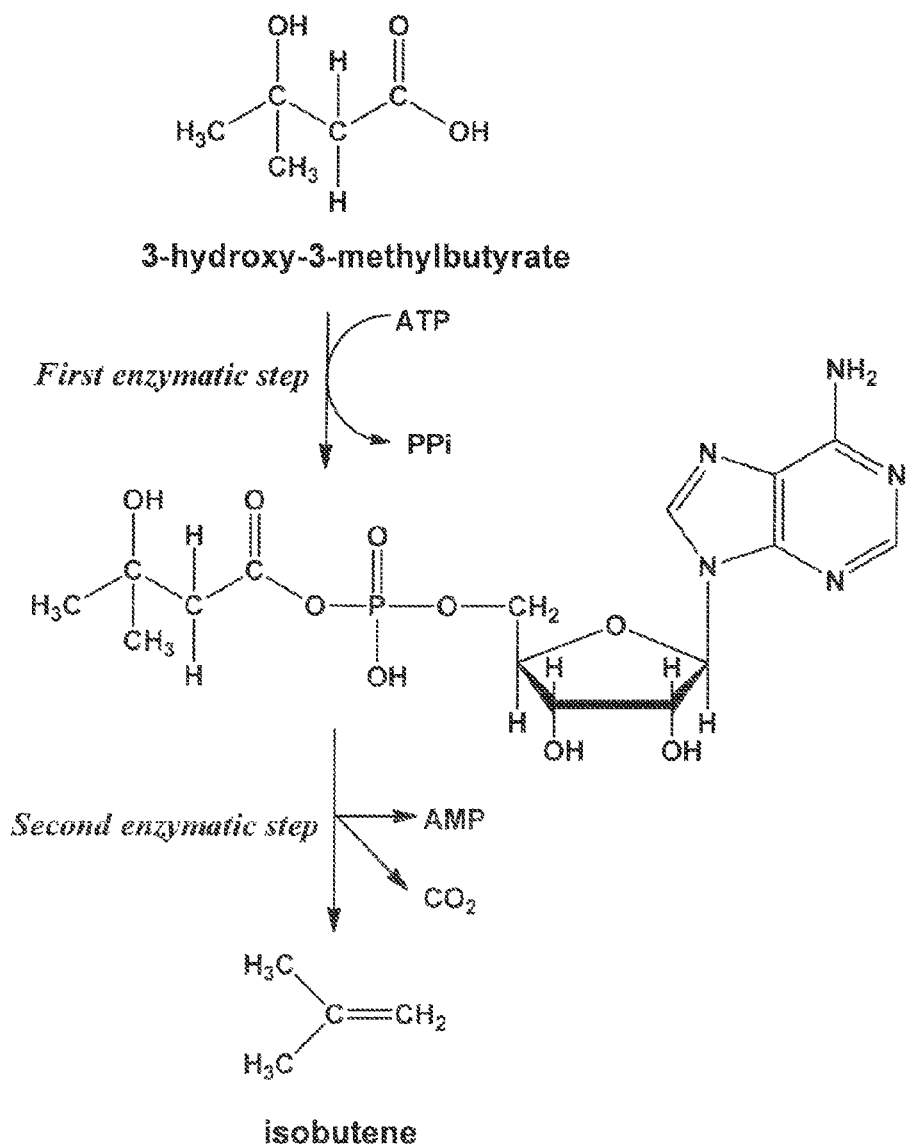

In one preferred embodiment the method according to the invention is a method for the production of isobutene and the 3-hydroxycarboxylate is 3-hydroxy-3-methylbutyrate (3-hydroxyisovalerate). The general reaction scheme for the overall conversion is shown in FIG. 6A. In a preferred embodiment, the conversion of 3-hydroxy-3-methylbutyrate into a corresponding 3-hydroxycarboxyl-nucleotidylate is carried out by using ATP or ADP as a co-substrate and the resulting 3-hydroxycarboxyl-nucleotidylate is 3-hydroxy-3-methylbutyryl-adenylate (3-hydroxyisovaleryl-adenylate). The corresponding reactions schemes are shown in FIGS. 6B and C, respectively.

Figure 7A:
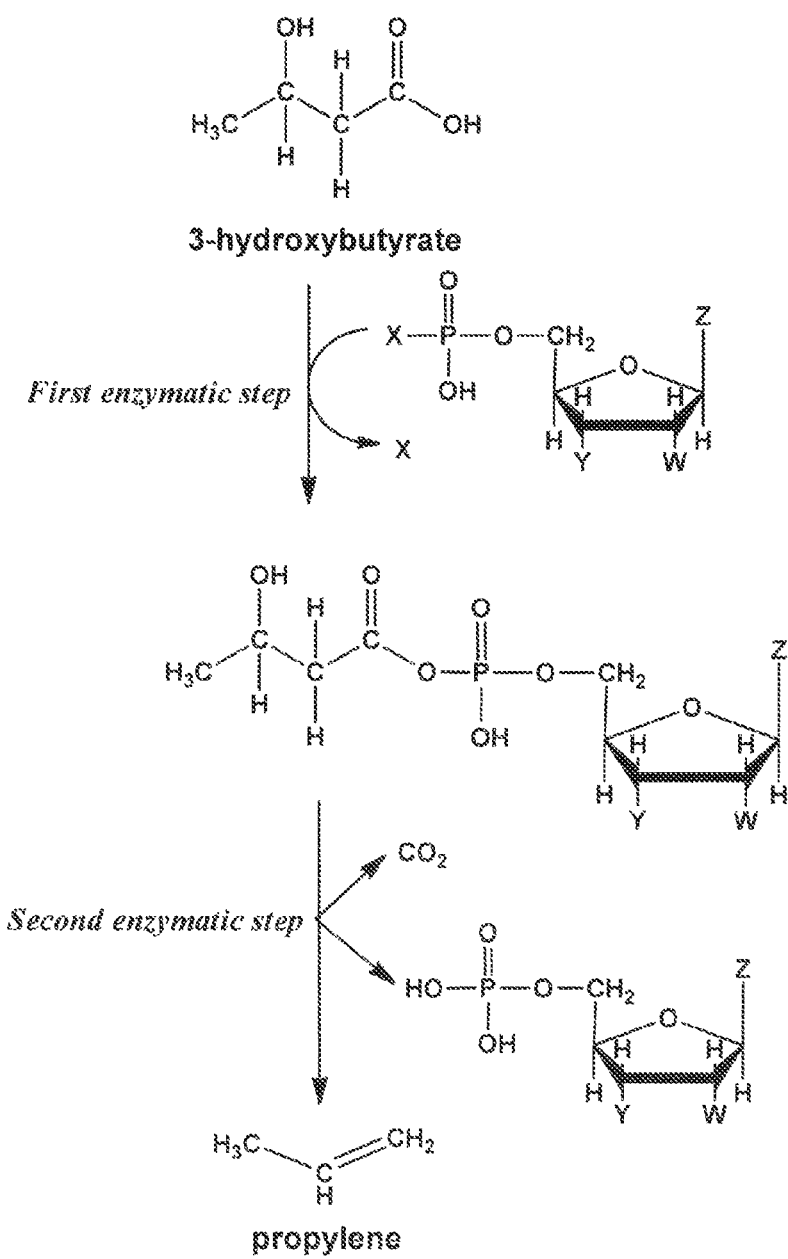
Figure 7B:
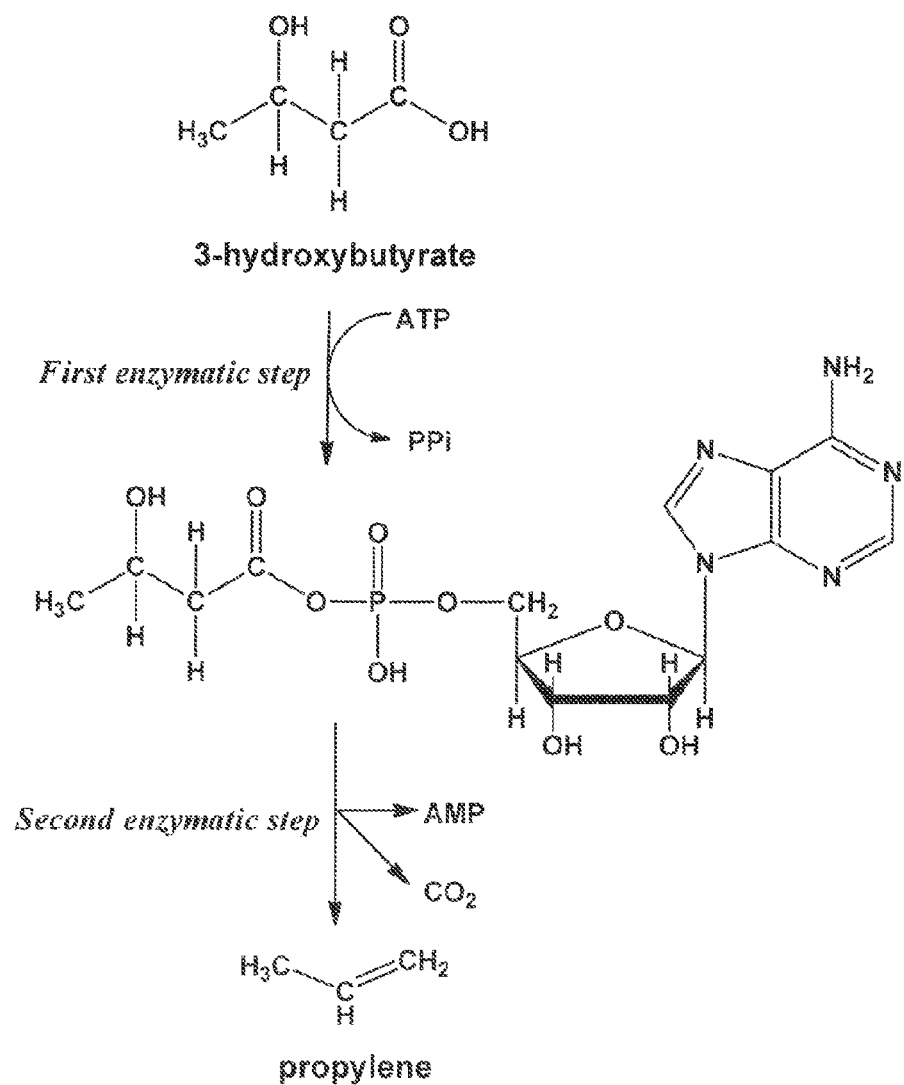

In another preferred embodiment the method according to the invention is a method for the production of propylene and the 3-hydroxycarboxylate is 3-hydroxybutyrate. The general reaction scheme for the overall conversion is shown in FIG. 7A. In a preferred embodiment, the conversion of 3-hydroxybutyrate into a corresponding 3-hydroxycarboxyl-nucleotidylate is carried out by using ATP or ADP as a co-substrate and the resulting 3-hydroxycarboxyl-nucleotidylate is 3-hydroxybutyryl-adenylate. The corresponding reactions schemes are shown in FIGS. 7B and C, respectively.

Figure 8A:
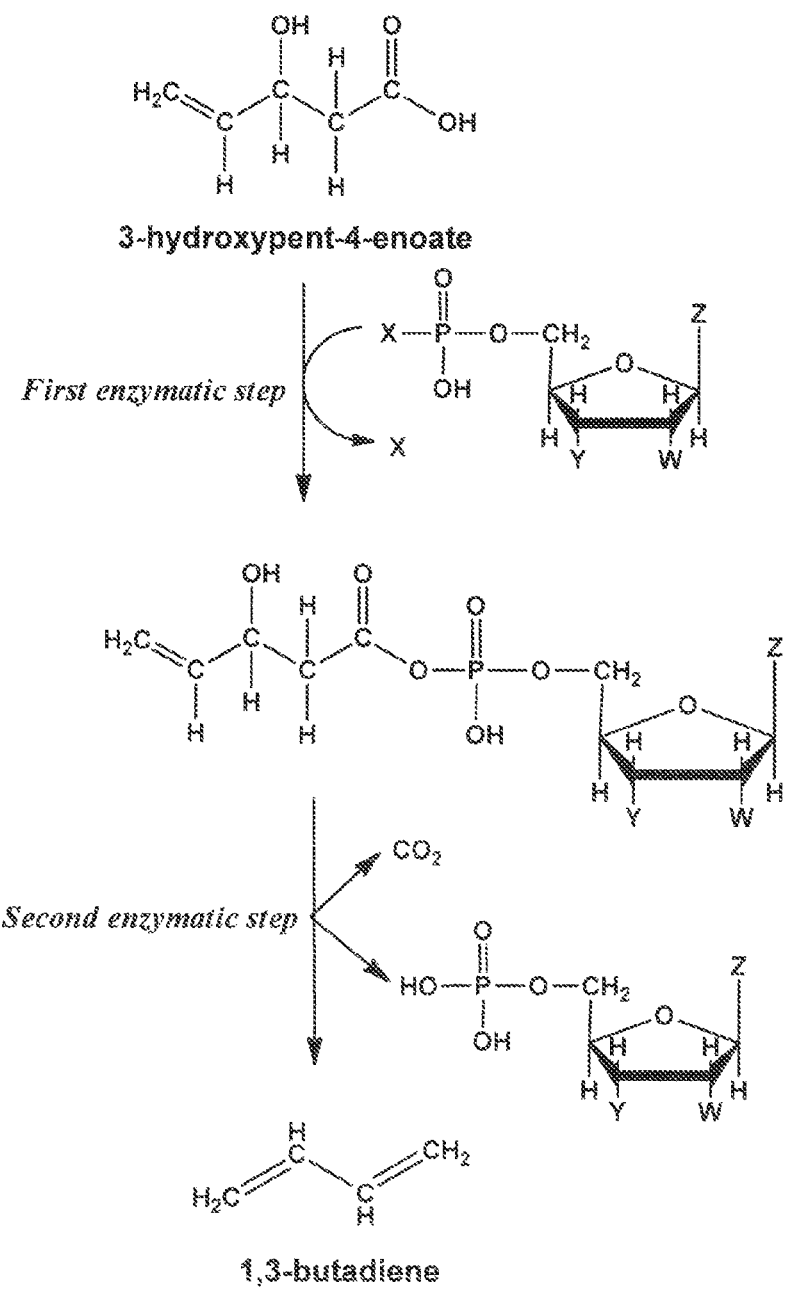
Figure 8B:
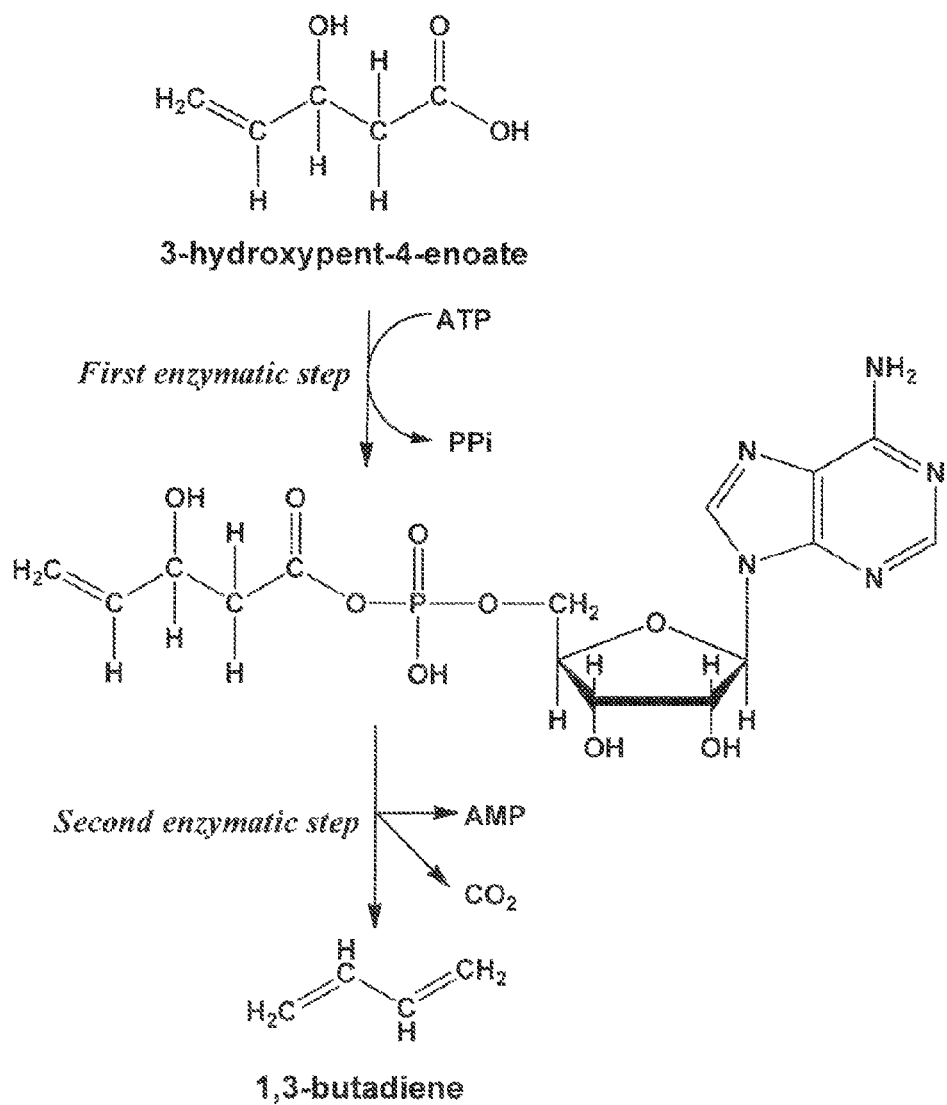

In a further preferred embodiment the method according to the invention is a method for the production of 1,3-butadiene and the 3-hydroxycarboxylate is 3-hydroxypent-4-enoate. The general reaction scheme for the overall conversion is shown in FIG. 8A. In a preferred embodiment, the conversion of 3-hydroxypent-4-enoate into a corresponding 3-hydroxycarboxyl-nucleotidylate is carried out by using ATP or ADP as a co-substrate and the resulting 3-hydroxycarboxyl-nucleotidylate is 3-hydroxypent-4-enoyl-adenylate. The corresponding reactions schemes are shown in FIGS. 8B and C, respectively.

An enzyme employed in the process according to the invention can be a naturally occurring enzyme or it can be an enzyme which is derived from a naturally occurring enzyme, e.g. by the introduction of mutations or other alterations which, e.g., alter or improve the enzymatic activity, the stability, etc (see also further below for a more detailed description).

When the present invention refers to an adenylate forming enzyme to be used for the conversion of a 3-hydroxycarboxylate into the 3-hydroxycarboxyl-nucleotidylate as described above, such reference to an adenylate forming enzyme also covers enzymes which are derived from such an adenylate forming enzyme, which are capable of catalyzing the conversion of a 3-hydroxycarboxylate into the 3-hydroxycarboxyl-nucleotidylate as described above but which only have a low affinity to their natural substrate or do no longer accept their natural substrate.

When the present invention refers to a certain enzyme to be used for the conversion of a 3-hydroxycarboxyl-nucleotidylate acid into the corresponding alkene as described above, such reference to an enzyme also covers enzymes which are derived from such an enzyme, which are capable of catalyzing the conversion of a 3-hydroxycarboxyl-nucleotidylate into the corresponding alkene as described above but which only have a low affinity to their natural substrate or do no longer accept their natural substrate.

Such a modification of the preferred substrate of an enzyme to be employed in a method according to the present invention allows to improve the conversion of the respective substrate of a reaction of a method according to the present invention and to reduce the production of unwanted by-product(s) due to the action of the enzyme on their natural substrate(s). Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic engineering in prokaryotic cells, a nucleic acid molecule encoding an enzyme can be introduced into plasmids which permit mutagenesis or sequence modification of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for their enzymatic activity and in particular for their capacity to convert a substrate as indicated in the respective reaction of a method according to the invention as a substrate rather than their natural substrate(s) as described above in connection with the description of the different enzymes which can be used in the context of the methods according to the present invention. Assays for measuring the capacity of an enzyme to catalyze a reaction as indicated in connection with a reaction of a method according to the invention are described in the Examples. The modified version of the enzyme having a low affinity to its natural substrate or no longer accepting its natural substrate may be derived from a naturally occurring enzyme or from an already modified, optimized or synthetically produced enzyme.

An enzyme employed in the process according to the present invention can be a natural version of the protein or a synthetic protein as well as a protein which has been chemically synthesized or produced in a biological system or by recombinant processes. The enzyme may also be chemically modified, for example in order to improve its/their stability, resistance, e.g. to temperature, for facilitating its purification or its immobilization on a support. The enzyme may be used in isolated form, purified form, in immobilized form, as a crude or partially purified extract obtained from cells synthesizing the enzyme, as chemically synthesized enzyme, as recombinantly produced enzyme, in the form of microorganisms producing them etc. The enzyme used in the invention can thus be natural or synthetic, and produced by chemical, biological or genetic means. It can also be chemically modified, for example in order to improve its activity, resistance, specificity, purification, or to immobilize it on a support.

It is also conceivable to use in the method according to the present invention fusion proteins which contain on the one hand the catalytic domain of an adenylate-forming enzyme which is required for achieving the conversion of the 3-hydroxycarboxylate into the 3-hydroxycarboxyl-nucleotidylate and on the other hand an OleC protein.

The methods according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form. In another embodiment the enzymes employed in the method are present in the reaction as a non-purified extract, or else in the form of non-lysed bacteria, so as to economize on protein purification costs.

For carrying out the process in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the corresponding alkene. The production of the alkene can be measured by methods known in the art, such as gas chromatography possibly linked to mass spectrometry detection or flame ionization detection (FID).

The enzymes may be in any suitable form allowing the enzymatic reaction to take place. They may be purified or partially purified or in the form of crude cellular extracts or partially purified extracts. It is also possible that the enzymes are immobilized on a suitable carrier.

The in vitro method according to the invention may be carried out in a one-pot-reaction, i.e. the substrate is combined in one reaction mixture with the above described enzymes necessary for the conversion into the corresponding alkene and the reaction is allowed to proceed for a time sufficient to produce the alkene. Alternatively, the method may also be carried out by effecting the different steps in a consecutive manner, i.e. by first mixing the 3-hydroxycarboxylate with one or more enzymes and allowing the reaction to proceed to the 3-hydroxycarboxyl-nucleotidylate and then adding one or more further enzymes to convert the 3-hydroxycarboxyl-nucleotidylate further into the corresponding alkene.

The recovery of the produced alkene may involve one step or multiples steps. For example, the alkene can be recovered using standard techniques such as adsorption/desorption, gas stripping, fractionation. Separation of the produced alkene from $CO_2$ can be achieved by the condensation of $CO_2$ at low temperature. $CO_2$ can also be removed by polar solvents, e.g. ethanolamine.

In another embodiment the method according to the invention is carried out in culture, in the presence of an organism, preferably a microorganism, producing an enzyme described above which can convert a 3-hydroxycarboxylate into a 3-hydroxycarboxyl-nucleotidylate and which also produces an enzyme necessary for further converting the 3-hydroxycarboxyl-nucleotidylate into the corresponding alkene as described herein above. Such organisms or microorganisms are also an object of the present invention.

If a (micro)organism is used which naturally expresses one of the required enzyme activities, it is possible to modify such a (micro)organism so that this activity is overexpressed in the (micro)organism. This can, e.g., be achieved by effecting mutations in the promoter region of the corresponding gene so as to lead to a promoter which ensures a higher expression of the gene. Alternatively, it is also possible to mutate the gene as such so as to lead to an enzyme showing a higher activity. By using (micro)organisms which express the enzymes which are necessary to convert a 3-hydroxycarboxylate into a 3-hydroxycarboxyl-nucleotidylate and which also produce an enzyme necessary for further converting the 3-hydroxycarboxyl-nucleotidylate into the corresponding alkene as described herein above, it is possible to carry out the method according to the invention directly in the culture medium, without the need to separate or purify the enzymes.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (microorganisms), i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

In one embodiment the (micro)organism according to the present invention or employed in the method according to the invention is an organism, preferably a microorganism, which has been genetically modified to contain one or more foreign nucleic acid molecules encoding one or more of the enzymes as described above in connection with the conversion of a 3-hydroxycarboxylate into a 3-hydroxycarboxyl-nucleotidylate and which also produces an enzyme necessary for further converting the 3-hydroxycarboxyl-nucleotidylate into the corresponding alkene as described herein above. The term "foreign" or "exogenous" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. is naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia, Alcaligenes* or *Bacillus* and even more preferably of the species *Escherichia coli, Alcaligenes eutrophus* or *Bacillus megaterium*.

In a further preferred embodiment the microorganism is a fungus, more preferably a fungus of the genus *Saccharomyces, Schizosaccharomyces, Aspergillus, Pichia, Trichoderma* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*.

In another preferred embodiment, the method according to the invention makes use of a photosynthetic microorganism expressing an enzyme which is capable of catalyzing the conversion of a 3-hydroxycarboxylate into a 3-hydroxycarboxyl-nucleotidylate and which also produces an enzyme which can catalyzes the conversion of the 3-hydroxycarboxyl-nucleotidylate into the corresponding alkene as described herein above. Preferably, the microorganism is a photosynthetic bacterium or a microalgae. In a further embodiment the microorganism is an algae, more preferably an algae belonging to the diatomeae.

It is also conceivable to use in the method according to the invention one microorganism that produces an enzyme catalyzing the conversion of a 3-hydroxycarboxylate into a 3-hydroxycarboxyl-nucleotidylate as described above and another microorganism that produces an enzyme catalyzing the conversion of the 3-hydroxycarboxyl-nucleotidylate into the corresponding alkene as described above.

In another preferred embodiment the method according to the invention makes use of a multicellular organism expressing an enzyme which can catalyzes the conversion of a 3-hydroxycarboxylate into a 3-hydroxycarboxyl-nucleotidylate and which also produces an enzyme which can catalyze the conversion of the 3-hydroxycarboxyl-nucleotidylate into the corresponding alkene as described herein above. Examples for such organisms are plants or animals.

The present invention also relates to the (micro)organism as described hereinabove in connection with the method according to the invention.

In a particularly preferred embodiment, the method involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In one embodiment the method according to the present invention employs an organism, preferably a microorganism, which is mesophilic and which can be cultured at temperatures of around 30° C. to 37° C.

In another preferred embodiment the method according to the present invention employs an organism, preferably a microorganism, which is thermophilic and which can be cultured at higher temperatures, e.g. higher than 60° C.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above.

Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from liters to cubic meters, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In a further embodiment the method of the invention is carried out under conditions under which the produced alkene is in a gaseous state. In such a case, it is furthermore preferred that the method is carried out under microaerophilic conditions. This means that the quantity of injected air is limiting so as to minimize residual oxygen concentrations in the gaseous effluents containing the alkene.

In another embodiment the method according to the invention furthermore comprises the step of collecting the gaseous alkene degassing out of the reaction. Thus in a preferred embodiment, the method is carried out in the presence of a system for collecting the alkene under gaseous form during the reaction.

As a matter of fact, short alkenes, and particularly ethylene, propylene, butene isomers and 1,3-butadiene, adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

In a particular embodiment, the method also comprises detecting the alkene (for example propylene, ethylene, isobutylene or 1,3-butadiene) which is present in the gaseous phase. The presence of the compound to be produced in an environment of air or another gas, even in small amounts, can be detected by using various techniques and in particular by using gas chromatography systems with infrared or flame ionization detection, or by coupling with mass spectrometry.

In a particular embodiment, the alkenes produced by a method according to the invention are condensed, then optionally reduced, by using techniques known to one of skill in the art, so as to produce longer chain alkenes, or longer chain alkanes. For example, isobutylene can be used to synthesize isooctane: the catalytic methods for successfully carrying out this reaction have already been fully described.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (*Hevea brasiliensis*).

When the process according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In a particularly preferred embodiment, the method according to the present invention is carried out by making use of an organism, preferably a microorganism, which produces the 3-hydroxycarboxylate according to formula I to be converted according to the method of the present invention. 3-hydroxyalkanoates are part of 3-hydroxycarboxylic acids and are naturally produced by a number of organisms, in particular microorganisms, such as bacteria of the geni *Burkholderia* (Rocha et al., World J. Microbiol. Biotechnol. 24 (2008), 427-431), Chromobacterium (Steinbüchel et al., Appl. Microbiol. Biotechnol. 39 (1993), 443-449) and *Bacillus* (Singh et al., Microbial Cell Factories 8 (2009), 38). Thus, for example, Steinbüchel et al. (loc. cit.) report on the production of 3-hydroxybutyrate in Chromobacterium *violaceum*. Moreover, the metabolic pathways leading to 3-hydroxycarboxylic acids such as 3-hydroxybutyric acid are well established (see, e.g., Tokiwa and Ugwu (J. Biotechnol. 132 (2007), 264-272) and Jian et al. (Appl. Microbiol. Biotechnol. 82 (2009), 995-1003). In addition to that, several corresponding synthetic pathways have already been introduced into other organisms, such as *E. coli* (see, e.g., Zhao et al. (FEMS Microbiol. Lett. 218 (2003), 59-64); Madison and Huisman (Microbiol. Mol. Biol. Rev. 63 (1999), 21-53); Tseng et al. (Appl. Environ. Microbiol. 75 (2009), 3137-3145)).

The enzymes used in the method according to the invention can be a naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. A detailed description of genetic modification of microorganisms will be given further below. Preferably, the nucleic acid molecule introduced into the microorganism is a nucleic acid molecule which is heterologous/exogenous with respect to the microorganism, i.e. it does not naturally occur in said microorganism.

In the context of the present invention, an "increased activity" means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), lp1, rac (Koros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention also relates to organisms, preferably microorganisms, which produce the enzymes necessary for the conversion of a 3-hydroxycarboxylate into a 3-hydroxycarboxyl-nucleotidylate and for further converting the 3-hydroxycarboxyl-nucleotidylate into the corresponding alkene as described herein above. Thus, the present invention, in particular, relates to a (micro)organism which expresses (a) an adenylate forming enzyme; and
(b) an OleC protein as defined herein above.

As regards the preferred embodiments of the enzymes to be expressed in such a microorganism, the same applies as has been set forth above in connection with the method according to the present invention. In one preferred embodiment, the adenylate forming enzyme of (a) is not an OleC protein. In a preferred embodiment such an organism is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism.

Thus, the present invention also relates to an organism, preferably a microorganism, comprising a nucleic acid molecule coding for an enzyme as defined in (a) above and comprising a nucleic acid molecule coding for an enzyme as defined in (b) above. In a preferred embodiment at least one of the nucleic acid molecules is heterologous to the organism which means that it does not naturally occur in said organism. The microorganism is preferably a bacterium, a yeast or a fungus. In another preferred embodiment the organism is a plant or non-human animal. As regards other preferred embodiments, the same applies as has been set forth above in connection with the method according to the invention.

In a preferred embodiment the microorganism according to the present invention also produces a 3-hydroxycarboxylate according to formula I which is to be converted according to the method according to the present invention.

Moreover, the present invention also relates to a composition comprising a microorganism according to the present invention, a suitable culture medium and a 3-hydroxycarboxylate of formula I or a carbon source that can be converted by the microorganism to a 3-hydroxycarboxylate of formula I.

The present invention also relates to a composition comprising an adenylate forming enzyme and a 3-hydroxycarboxylate of formula I with the proviso that the adenylate forming enzyme is not 3-hydroxypropionyl-CoA synthetase and the 3-hydroxycarboxylate is not 3-hydroxypropionate.

The present invention also relates to a composition comprising
 (a) an OleC protein; and
 (b) a 3-hydroxycarboxyl-nucleotidylate of formula III.

Moreover, the present invention also relates to a composition comprising
 (a) an adenylate forming enzyme; and
 (b) an OleC protein
as defined herein above.

In a preferred embodiment such a composition also comprises a 3-hydroxycarboxylate of formula I. In another preferred embodiment the adenylate forming enzyme of (a) is not an OleC protein.

The present invention also relates to the use of an adenylate forming enzyme for the conversion of a 3-hydroxycarboxylate of formula I into a 3-hydroxycarboxyl-nucleotidylate of formula III as described herein above.

Furthermore, the present invention relates to the use of an OleC protein for the conversion of a 3-hydroxycarboxyl-nucleotidylate of formula III into an alkene of formula IV as described herein above.

The present invention also relates to the use of a combination comprising
 (a) an adenylate forming enzyme; and
 (b) an OleC protein
for the conversion of a 3-hydroxycarboxylate of formula I into an alkene of formula IV as described herein above. In one preferred embodiment the adenylate forming enzyme of (a) is not an OleC protein.

As regards the preferred embodiments of the different components recited, the same applies as has been set forth above in connection with the method according to the invention.

Other aspects and advantages of the invention will be described in the following examples, which are given for purposes of illustration and not by way of limitation. Each publication, patent, patent application or other document cited in this application is hereby incorporated by reference in its entirety.

FIG. 1: shows the general reaction scheme for converting a 3-hydroxycarboxylate into a 3-hydroxycarboxyl-nucleotidylate.

FIG. 2: shows the general reaction scheme for converting a 3-hydroxycarboxylate and ATP or ADP as a co-substrate into a 3-hydroxycarboxyl-adenylate.

FIG. 3: shows the general reaction scheme for converting a 3-hydroxycarboxylate and ATP or ADP as a co-substrate into a 3-hydroxycarboxyl-adenylate and further converting it into an alkene.

FIG. 4A: shows the general reaction scheme for converting a 3-hydroxycarboxyl-nucleotidylate into the corresponding alkene.

Figure 4B:
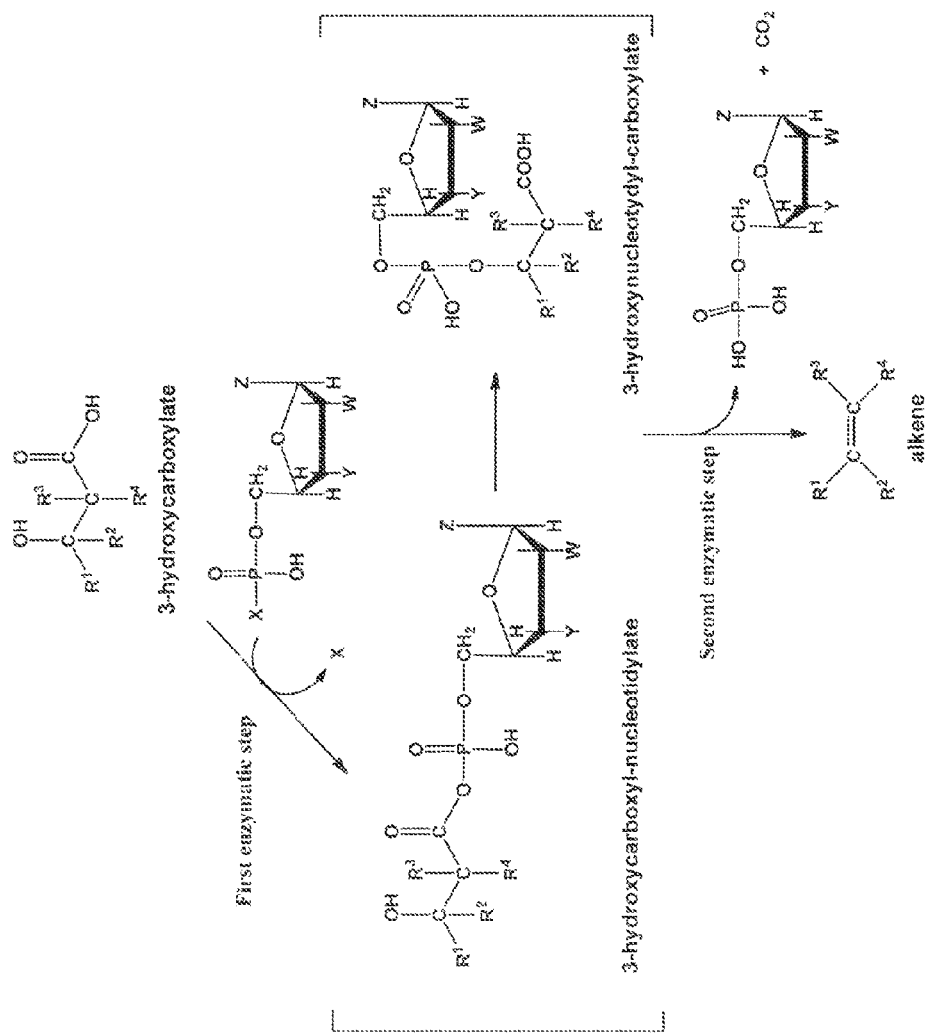

FIG. 4B: shows the reaction scheme for converting a 3-hydroxycarboxyl-nucleotidylate into the corresponding alkene via a 3-hydroxynucleotydyl-carboxylate.

FIG. 5: shows the general reaction scheme for converting a 3-hydroxycarboxyl-adenylate into the corresponding alkene.

FIG. 6A: shows the general scheme for converting 3-hydroxy-3-methylbutyrate into isobutene by using a method according to the present invention.

FIG. 6B: shows the general scheme for converting 3-hydroxy-3-methylbutyrate into isobutene by using a method according to the present invention employing ATP as a co-substrate.

Figure 6C:
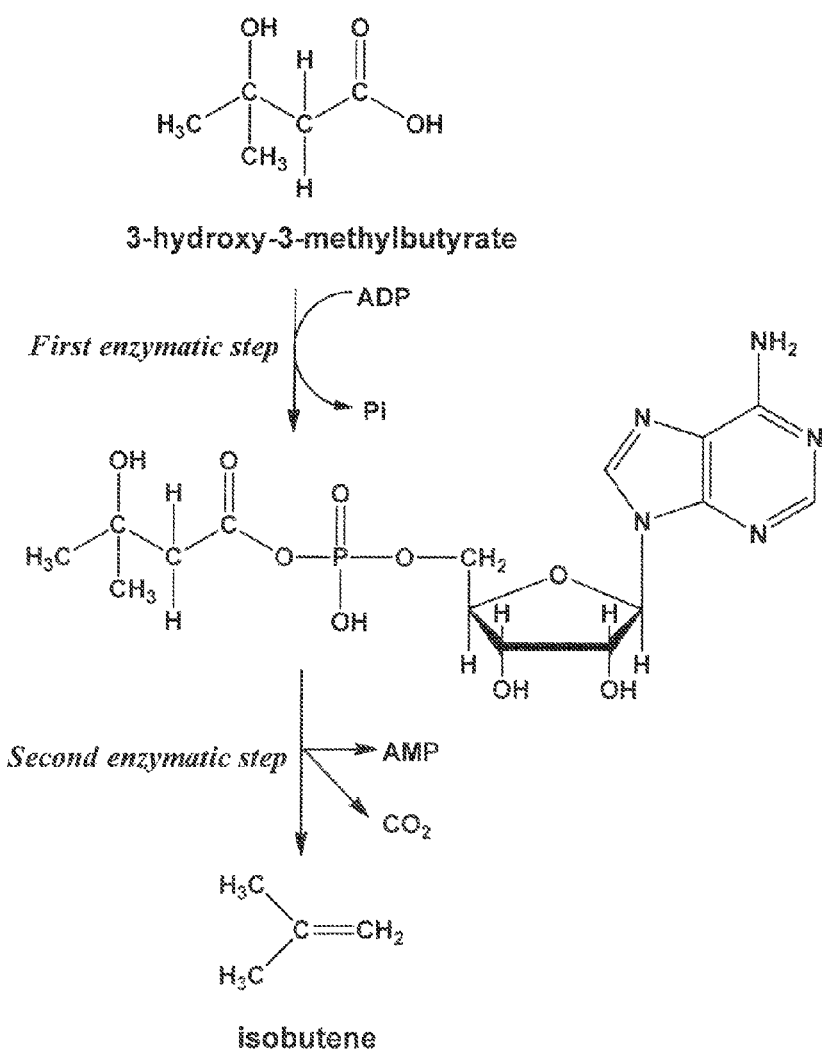

FIG. 6C: shows the general scheme for converting 3-hydroxy-3-methylbutyrate into isobutene by using a method according to the present invention employing ADP as a co-substrate.

FIG. 7A: shows the general scheme for converting 3-hydroxybutyrate into propylene by using a method according to the present invention.

FIG. 7B: shows the general scheme for converting 3-hydroxybutyrate into propylene by using a method according to the present invention employing ATP as a co-substrate.

Figure 7C:
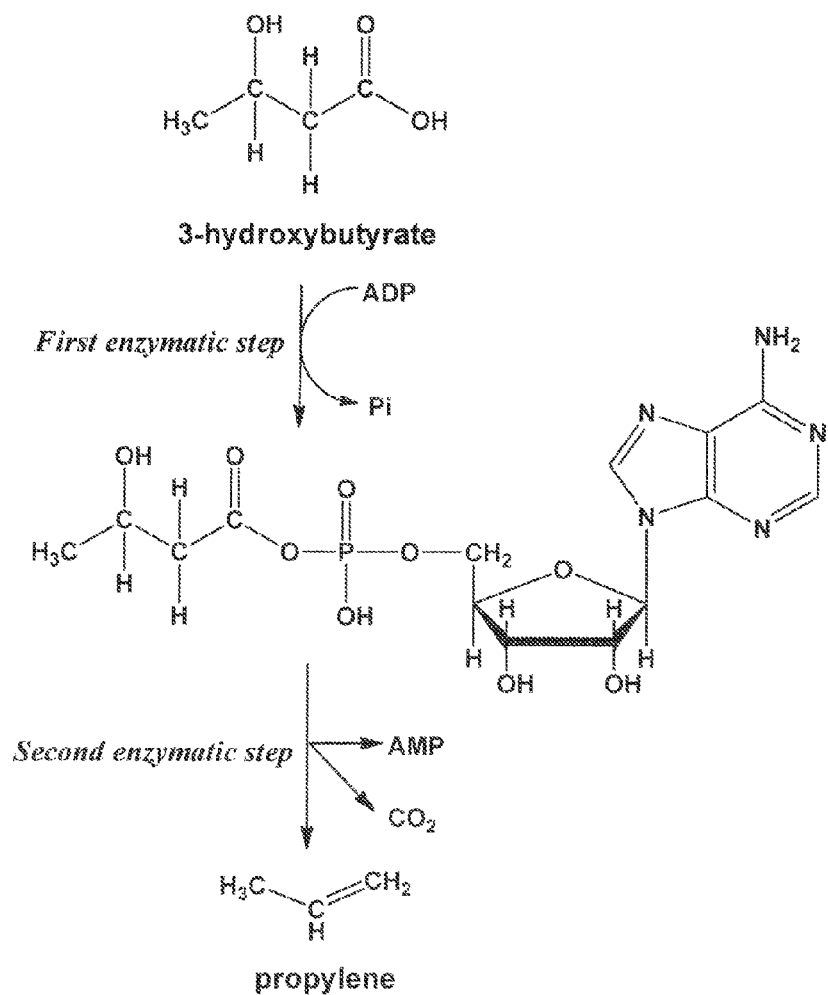

FIG. 7C: shows the general scheme for converting 3-hydroxybutyrate into propylene by using a method according to the present invention employing ADP as a co-substrate.

FIG. 8A: shows the general scheme for converting 3-hydroxypent-4-enoate into 1,3-butadiene by using a method according to the present invention.

FIG. 8B: shows the general scheme for converting 3-hydroxypent-4-enoate into 1,3-butadiene by using a method according to the present invention employing ATP as a co-substrate.

Figure 8C:
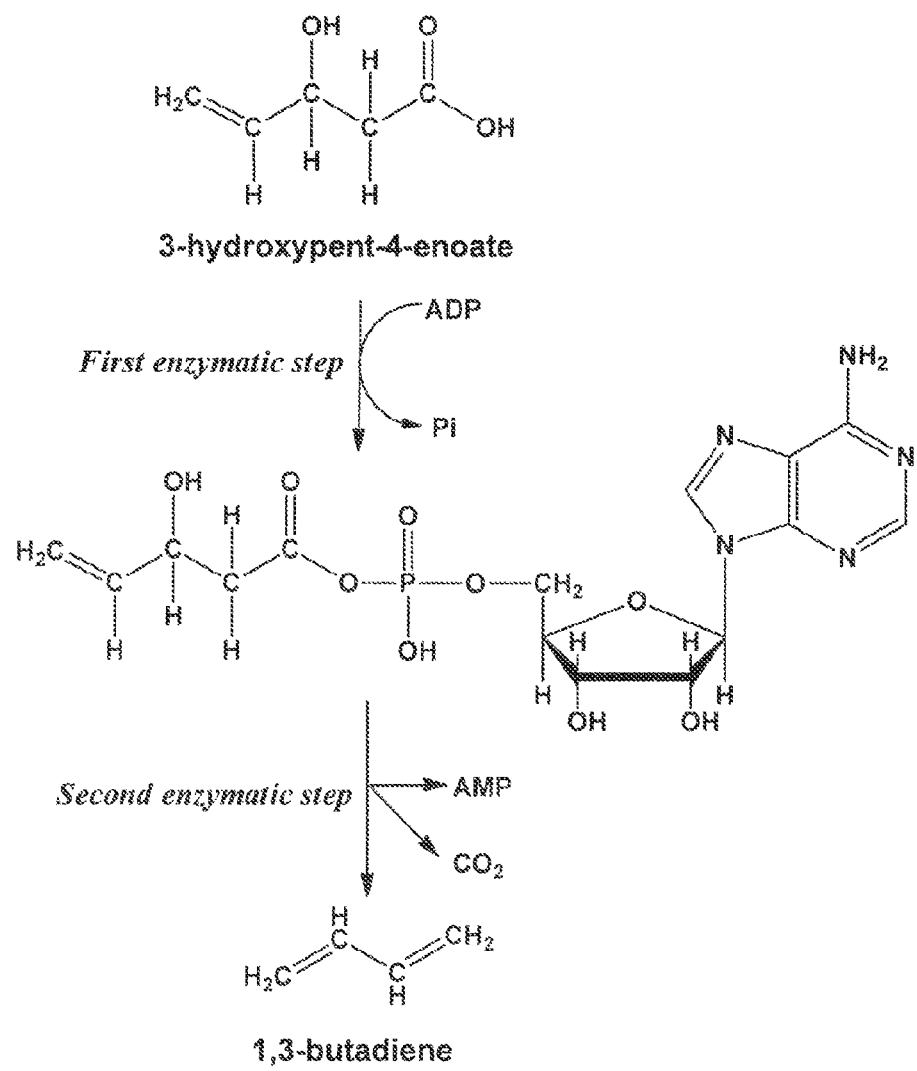

FIG. 8C: shows the general scheme for converting 3-hydroxypent-4-enoate into 1,3-butadiene by using a method according to the present invention employing ADP as a co-substrate.

Figure 9:
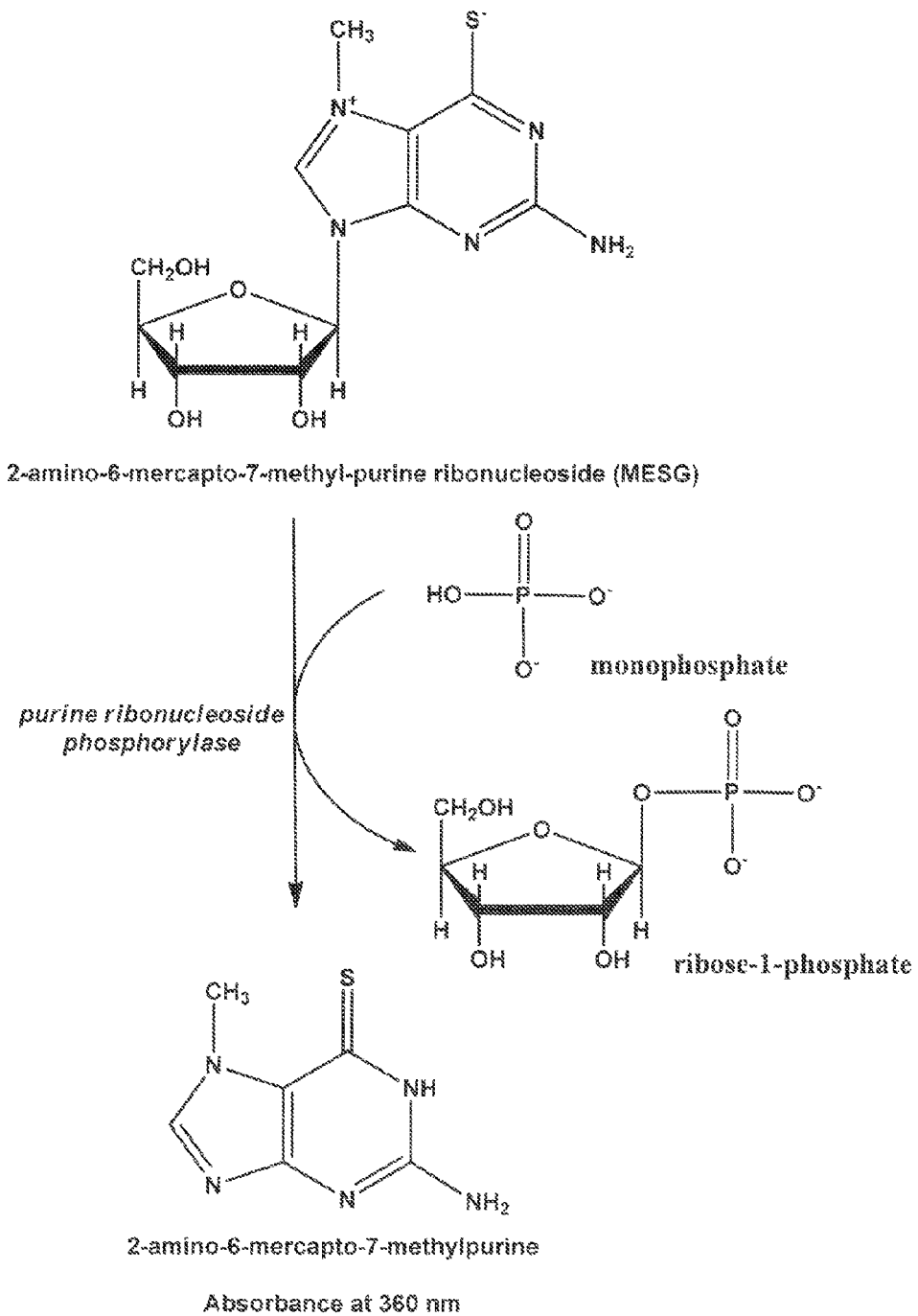

FIG. 9: shows a scheme of the diphosphate or monophosphate quantification assay, monitoring 2-amino-6-mercapto-7-methylpurine formation by the increase of absorbance at 360 nm.

Figure 10:
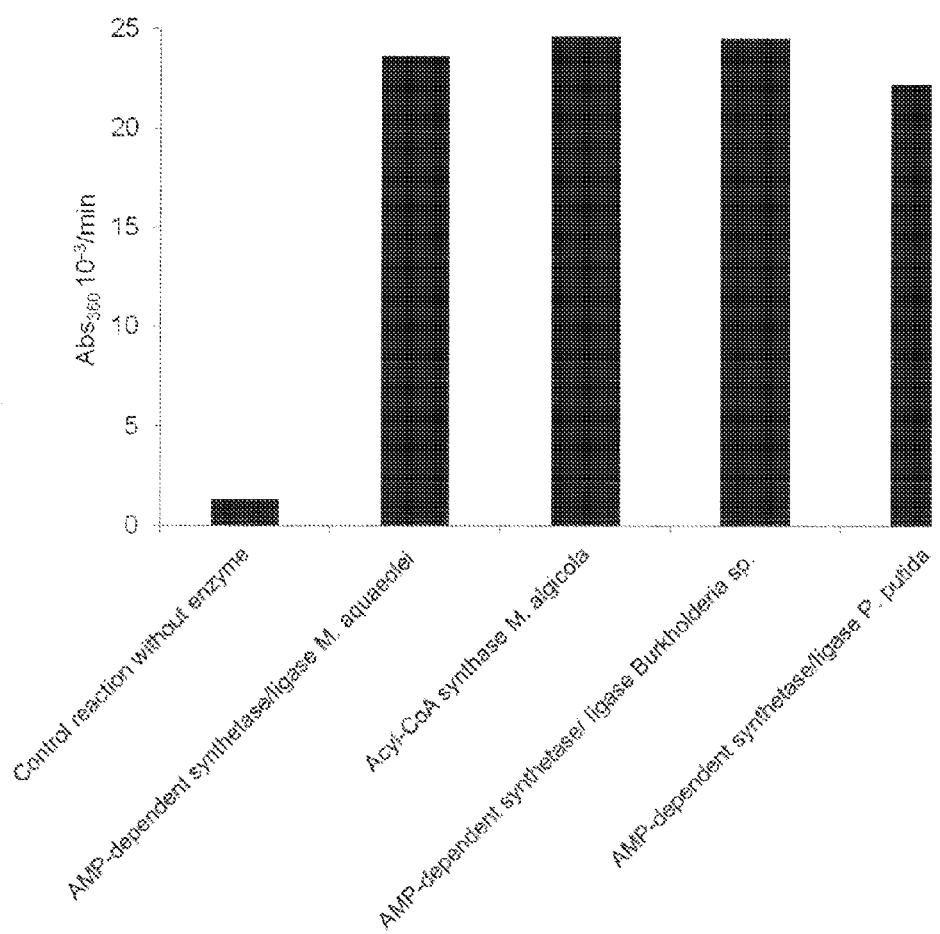

FIG. 10: shows adenylation activity of several studied enzymes for 3-hydroxypropionate monitored by recording the increase of absorbance of 2-amino-6-mercapto-7-methylpurine at 360 nm.

Figure 11:
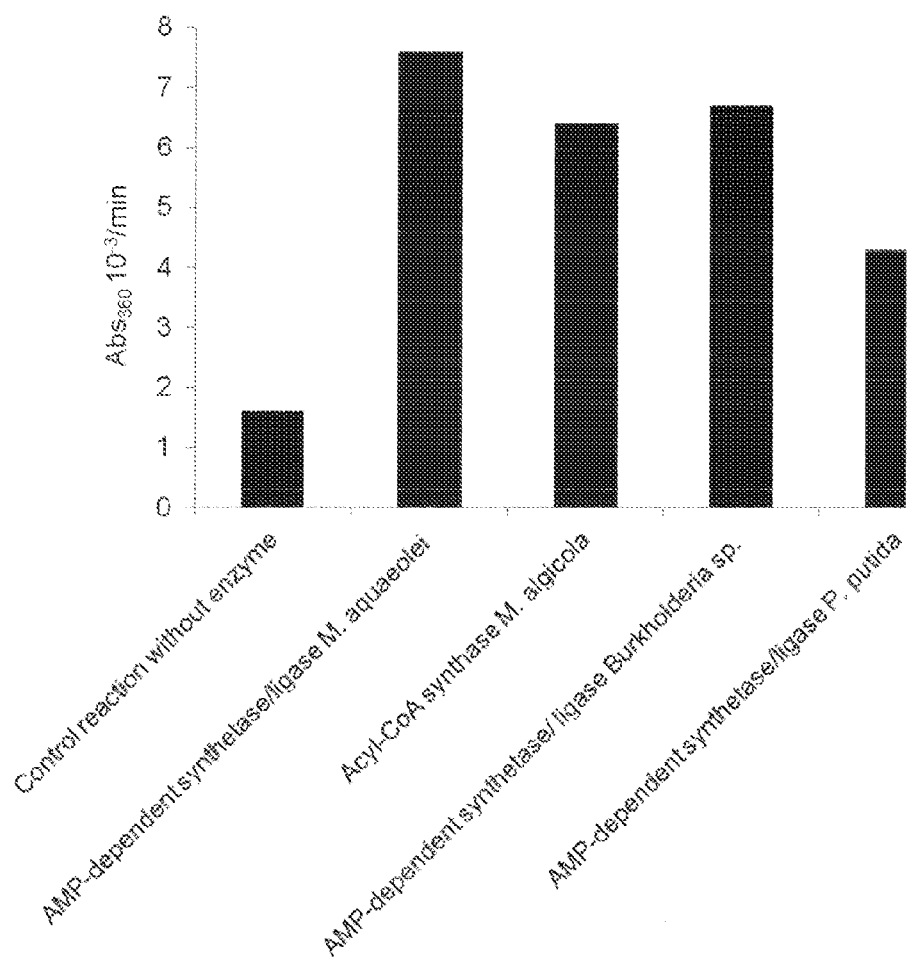

FIG. 11: shows adenylation activity of several studied enzymes for R-3-hydroxyvalerate monitored by recording the increase of absorbance of 2-amino-6-mercapto-7-methylpurine at 360 nm.

Figure 12:
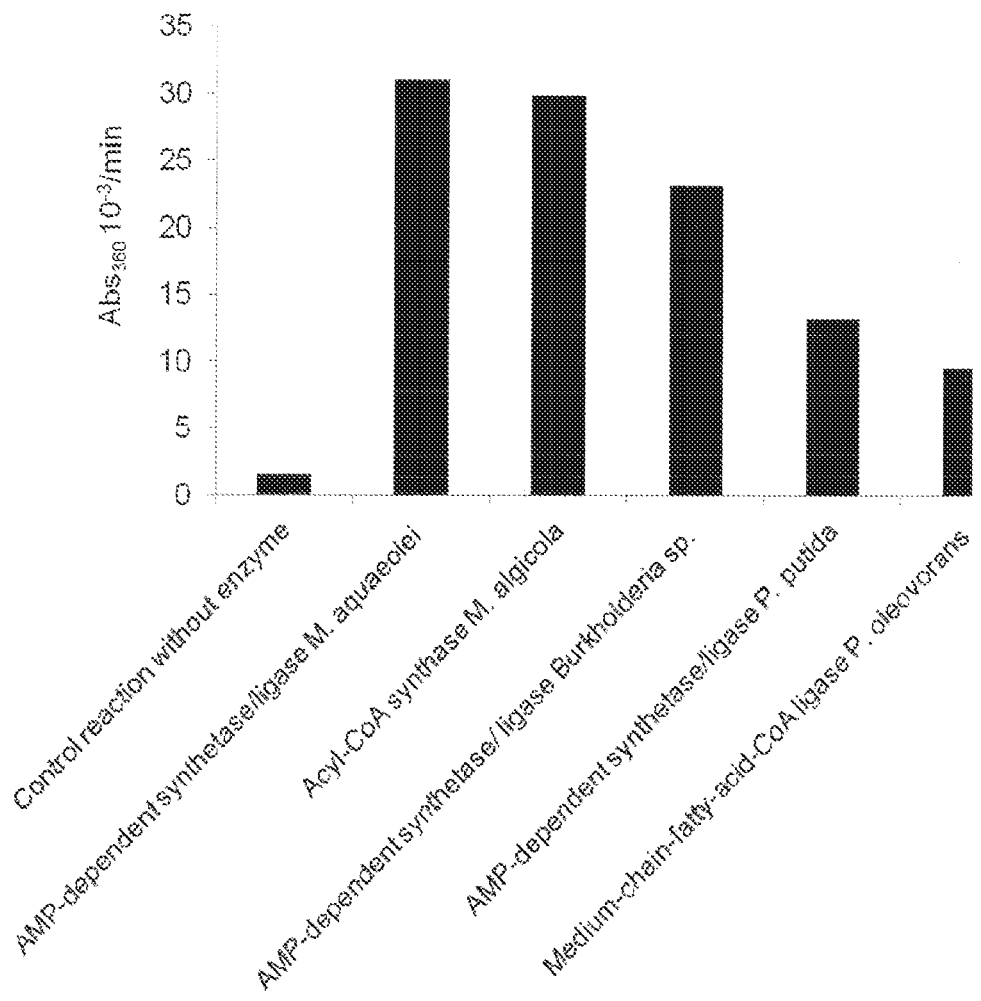

FIG. 12: shows adenylation activity of several studied enzymes for (R,S)-3-hydroxypent-4-enoate monitored by recording the increase of absorbance of 2-amino-6-mercapto-7-methylpurine at 360 nm.

Figure 13:
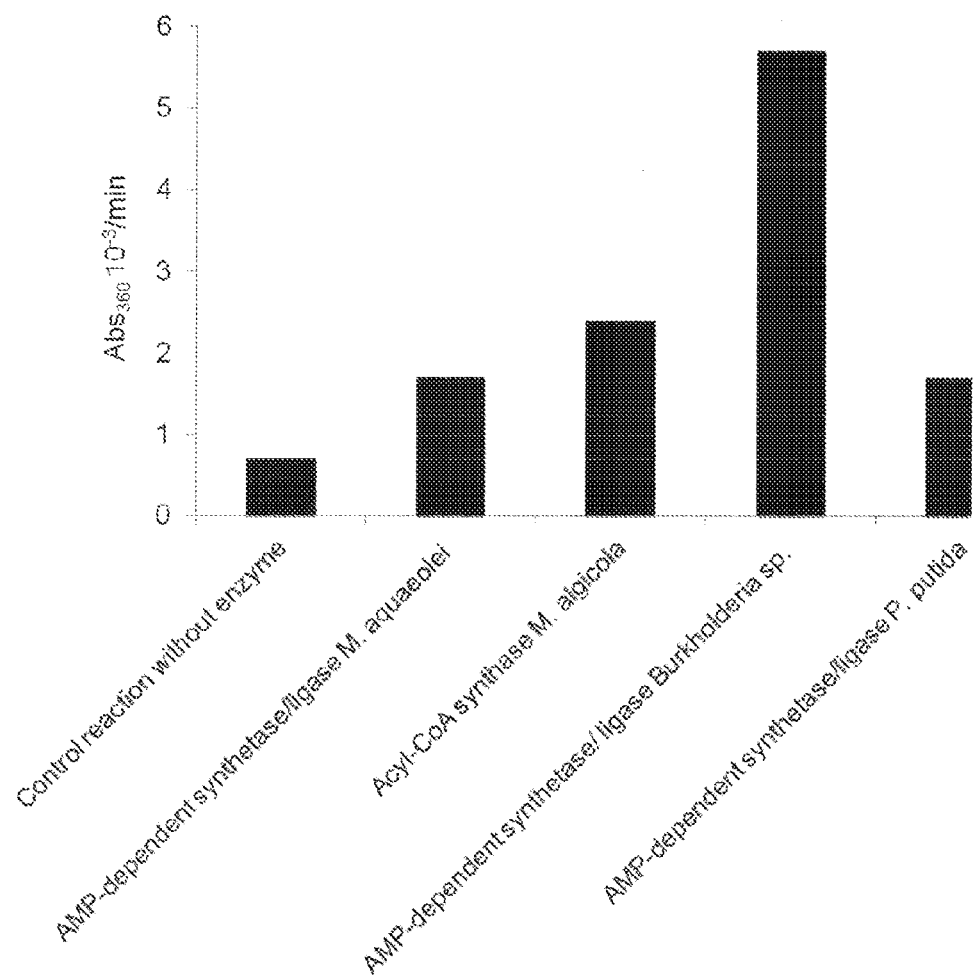

FIG. 13: shows adenylation activity of several studied enzymes for 3-hydroxyisovalerate monitored by recording the increase of absorbance of 2-amino-6-mercapto-7-methylpurine at 360 nm.

Figure 14:
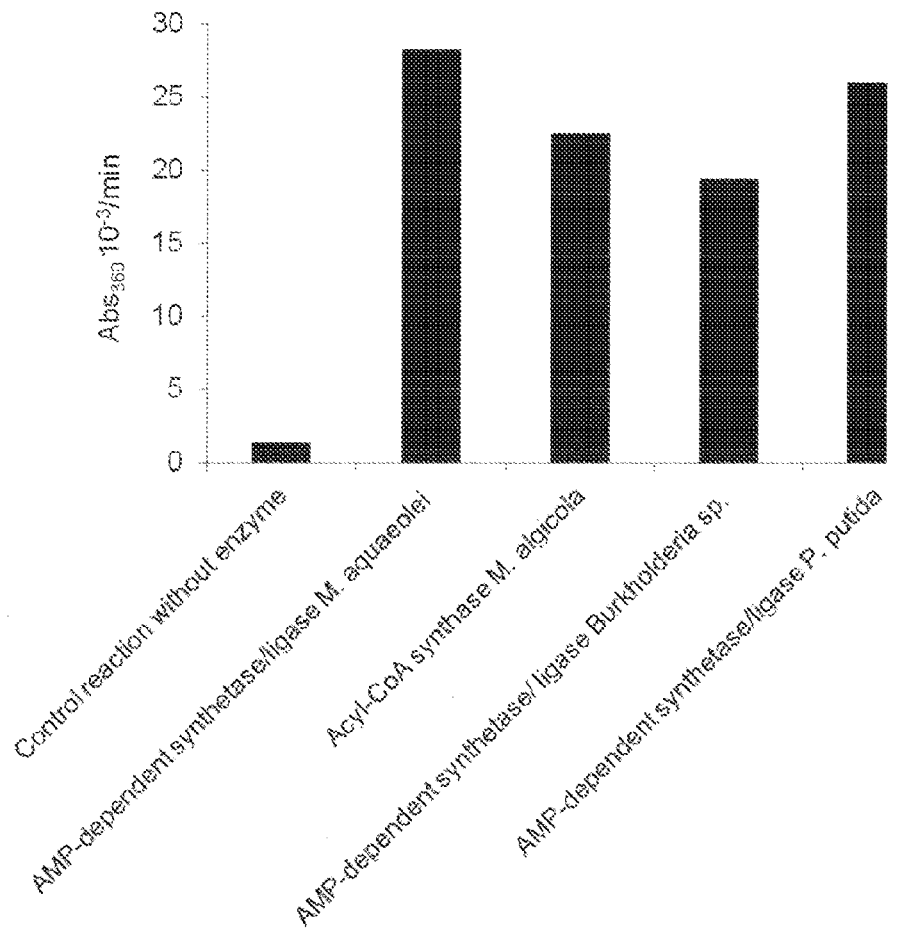

FIG. 14: shows adenylation activity of several studied enzymes for (R,S)-3-hydroxybutyrate monitored by recording the increase of absorbance of 2-amino-6-mercapto-7-methylpurine at 360 nm.

Figure 15:
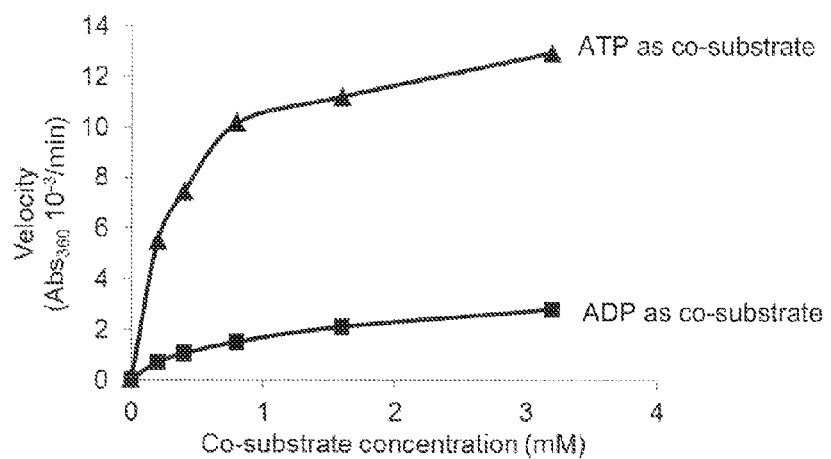

FIG. 15: shows a plot of the velocity as a function of co-substrates concentration for the adenylation reaction of (R,S)-3-hydroxybutyrate catalyzed by acyl-CoA synthase from *M. algicola*. Reaction was monitored by recording the increase of absorbance of 2-amino-6-mercapto-7-methylpurine at 360 nm.

Figure 16:
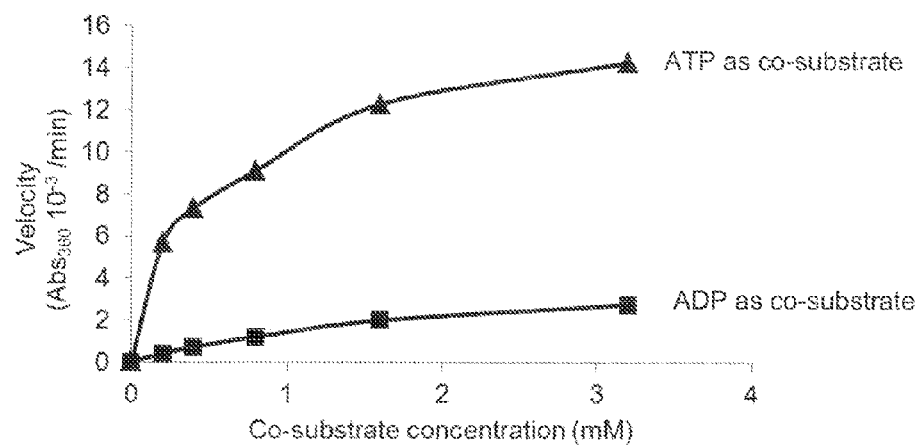

FIG. 16: shows a plot of the velocity as a function of co-substrates concentration for the adenylation reaction of (R,S)-3-hydroxybutyrate catalyzed by AMP-dependent synthetase/ligase from *Burkholderia* sp. Reaction was monitored by recording an increase of absorbance of 2-amino-6-mercapto-7-methylpurine at 360 nm.

Figure 17:
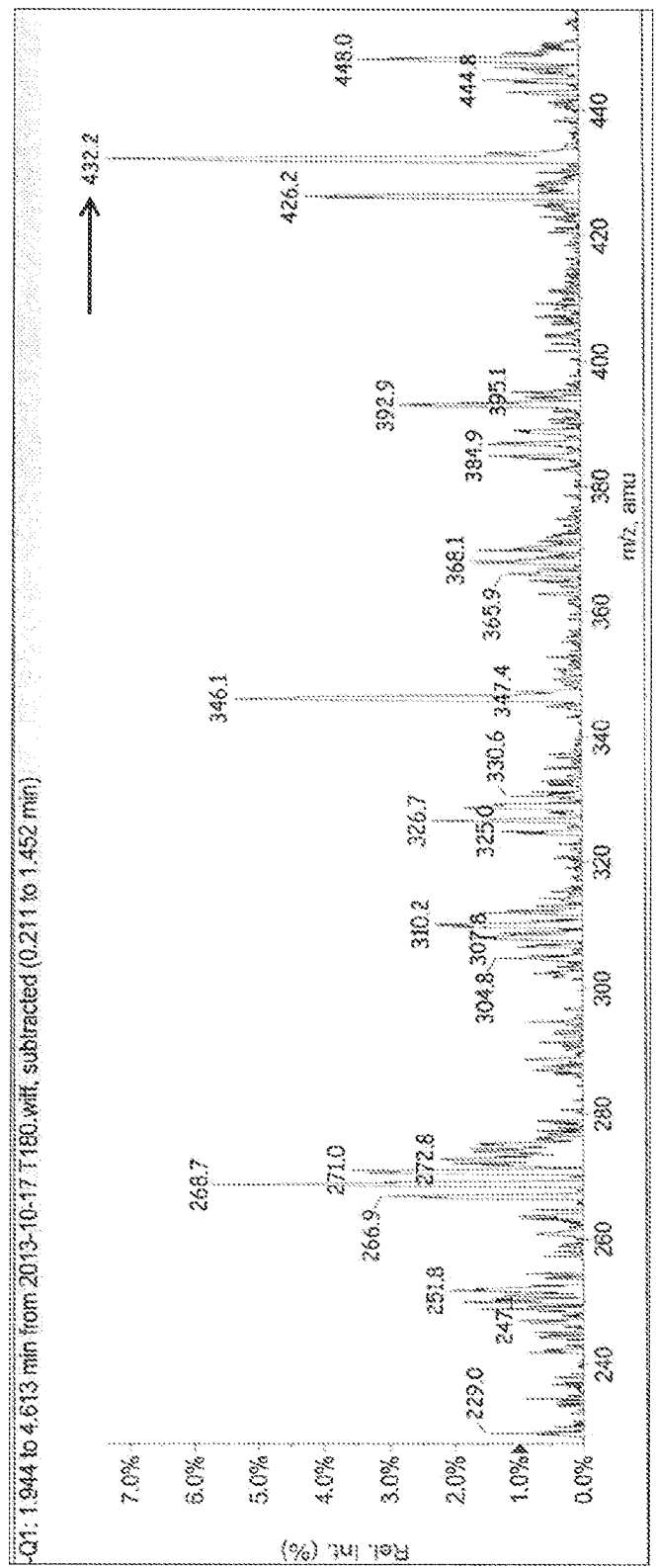

FIG. 17: shows an electrospray MS spectra of the adenylation reaction of (R,S)-3-hydroxybutyrate catalyzed by AMP-dependent synthetase/ligase from *Burkholderia* sp. MS analysis showed characteristic peak at m/z value of 432.2 for the mono-deprotonated form of 3-hydroxybutyryl-adenylate, [M-H]$^-$.

Figure 18:
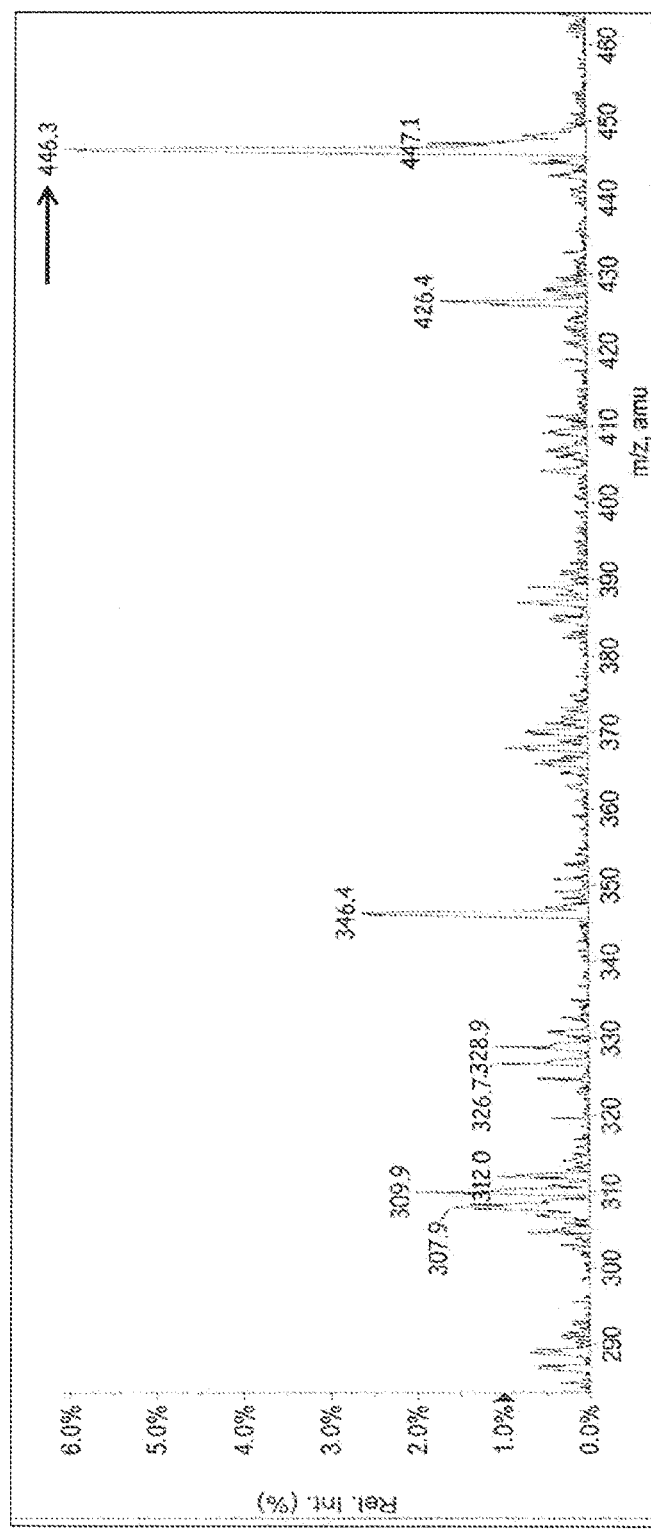

FIG. 18: shows an electrospray MS spectra of the adenylation reaction of R-3-hydroxyvalerate catalyzed by AMP-dependent synthetase/ligase from *Burkholderia* sp. MS analysis showed characteristic peak at m/z value of 446.3 for the mono-deprotonated form of 3-hydroxyvaleryl-adenylate, [M-H]$^-$.

Figure 19:
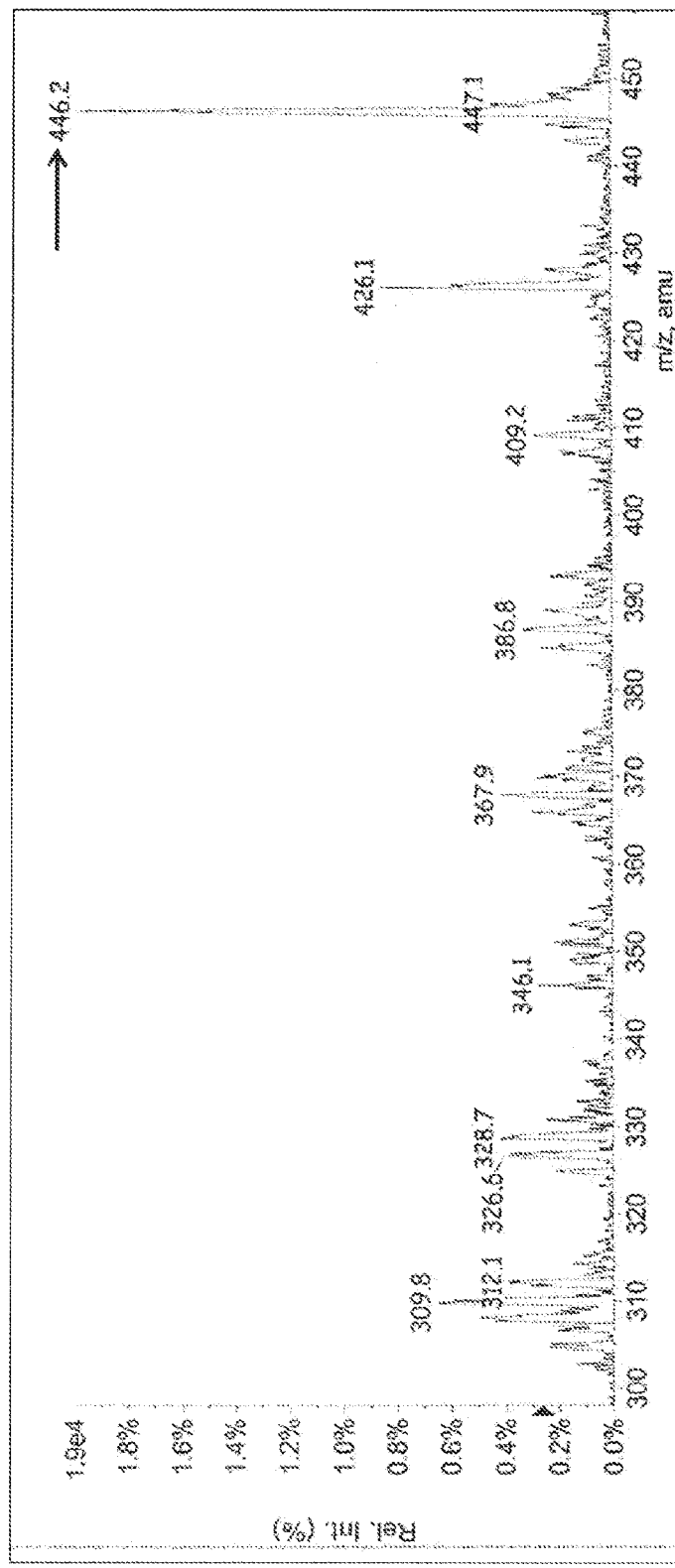

FIG. 19: shows an electrospray MS spectra of the adenylation reaction of 3-hydroxyisovalerate catalyzed by AMP-dependent synthetase/ligase from *Burkholderia* sp. MS analysis showed characteristic peak at m/z value of 446.2 for the mono-deprotonated form of 3-hydroxyisovaleryl-adenylate, [M-H]$^-$.

Figure 20:
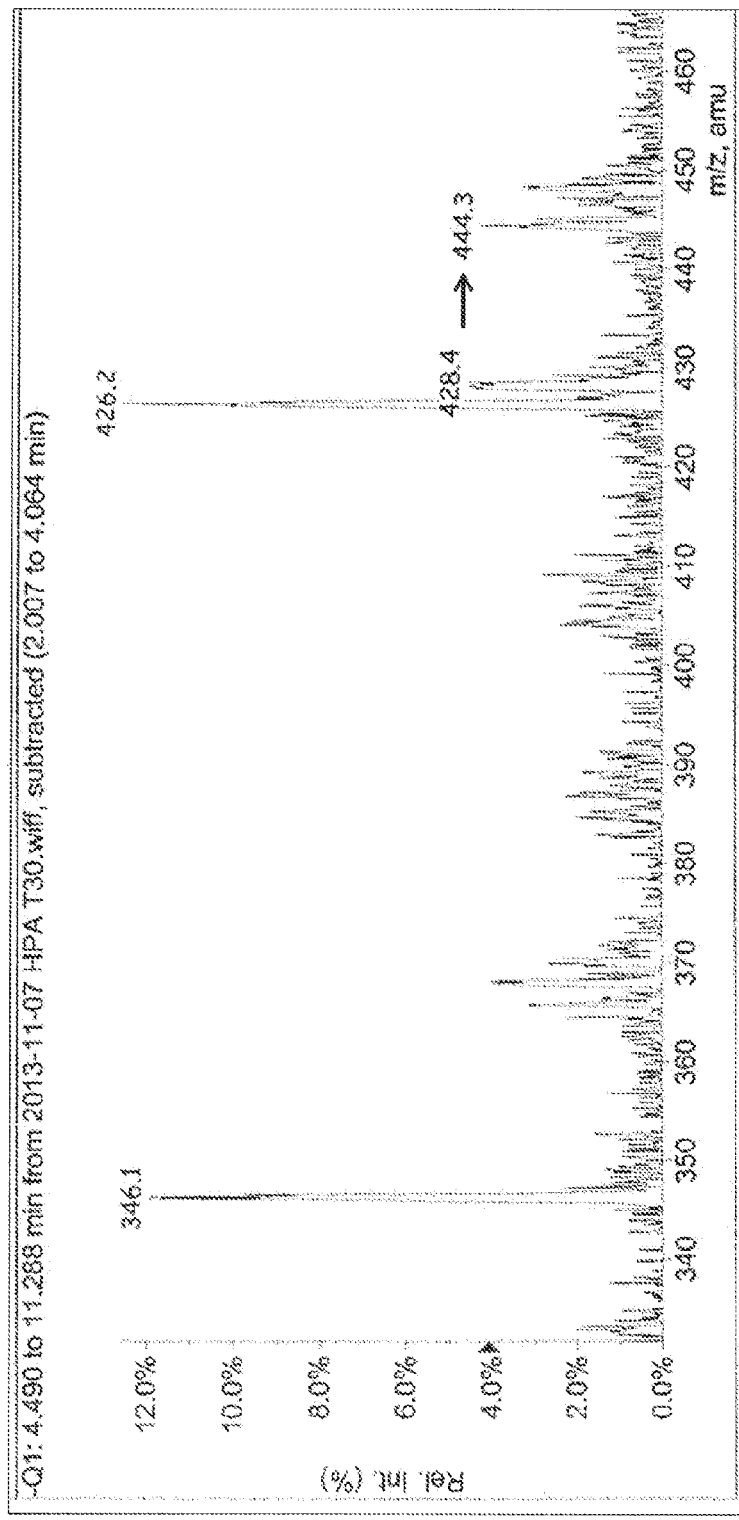

FIG. 20: shows an electrospray MS spectra of the adenylation reaction of (R,S)-3-hydroxypent-4-enoate catalyzed by AMP-dependent synthetase/ligase from *Burkholderia* sp. MS analysis showed characteristic peak at m/z value of 444.3 for the mono-deprotonated form of 3-hydroxypent-4-enoyl-adenylate, [M-H]$^-$.

Figure 21:
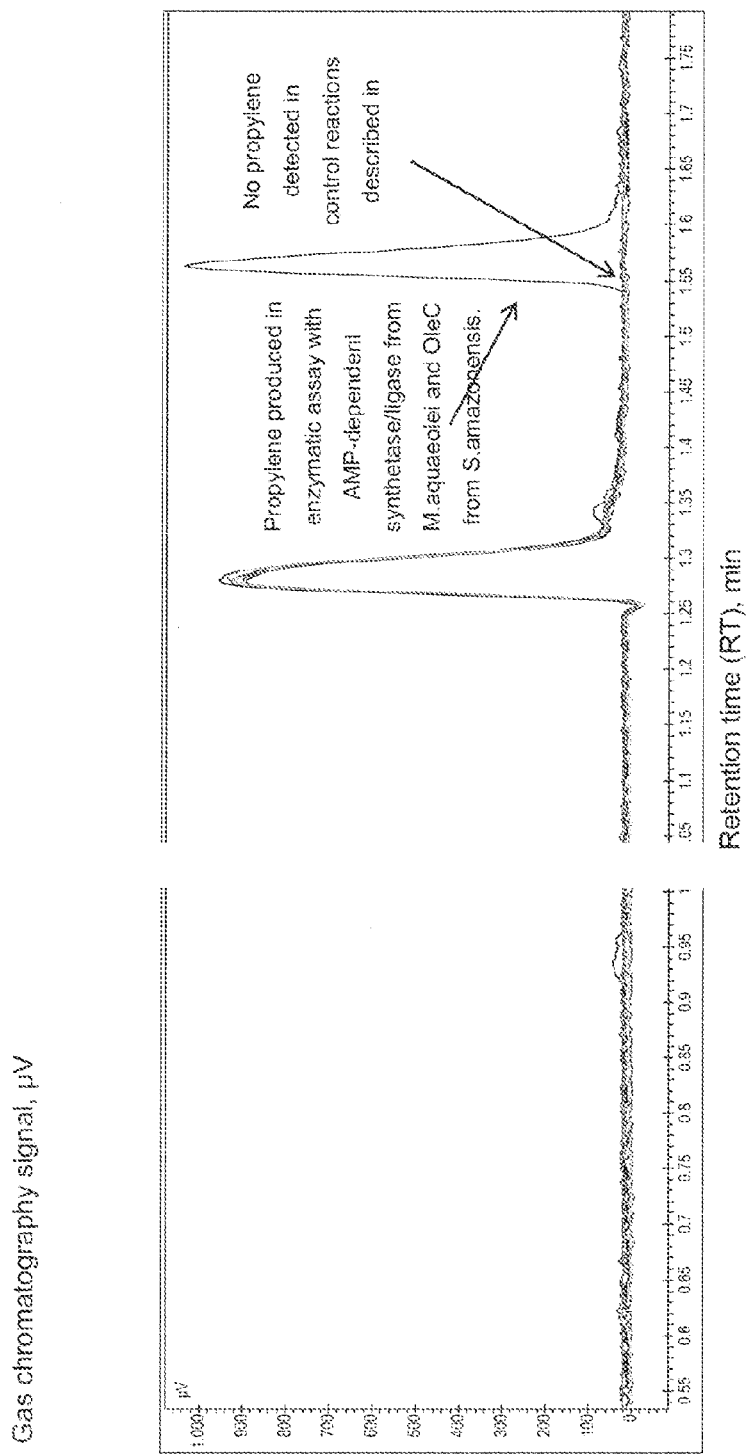

FIG. 21: shows GC/FID chromatograms obtained for enzymatic and enzyme-free reactions with (R,S)-3-hydroxybutyrate as a substrate and ATP as a co-substrate.

Figure 22:
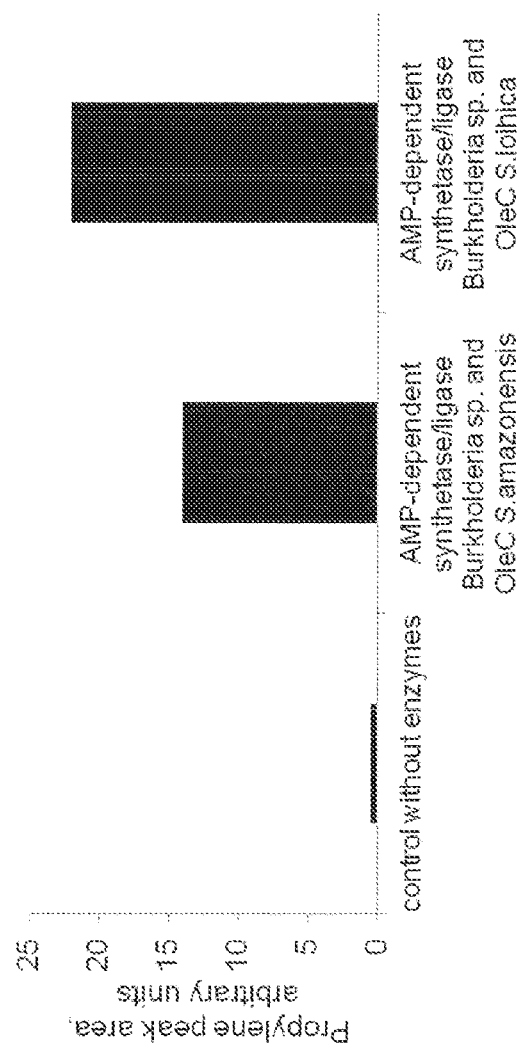

FIG. 22: shows enzyme-catalyzed propylene production from (R,S)-3-hydroxybutyrate as outlined in Example 12.

Figure 23:
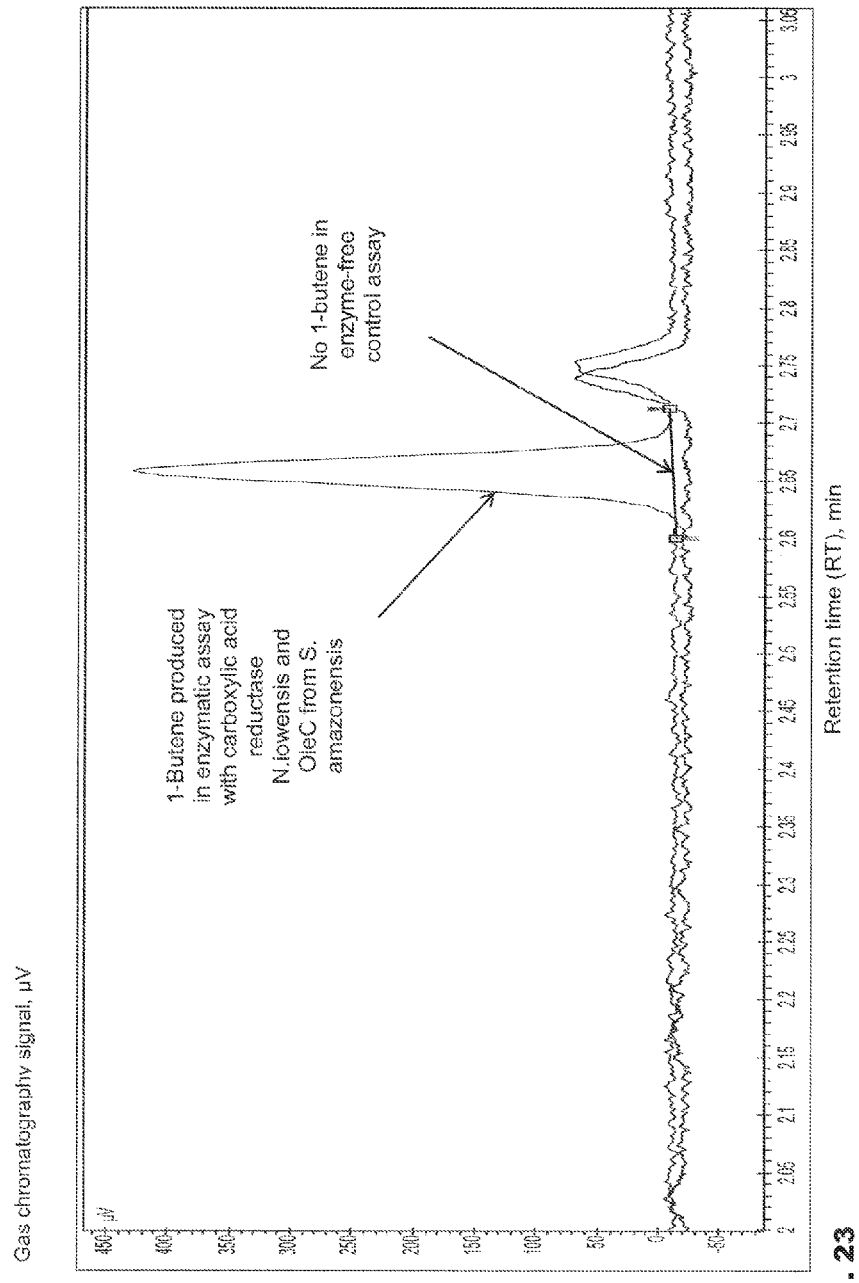

FIG. 23: shows GC/FID chromatograms obtained for enzymatic and enzyme-free reactions with (R)-3-hydroxyvalerate as a substrate and ATP as a co-substrate.

Figure 24:
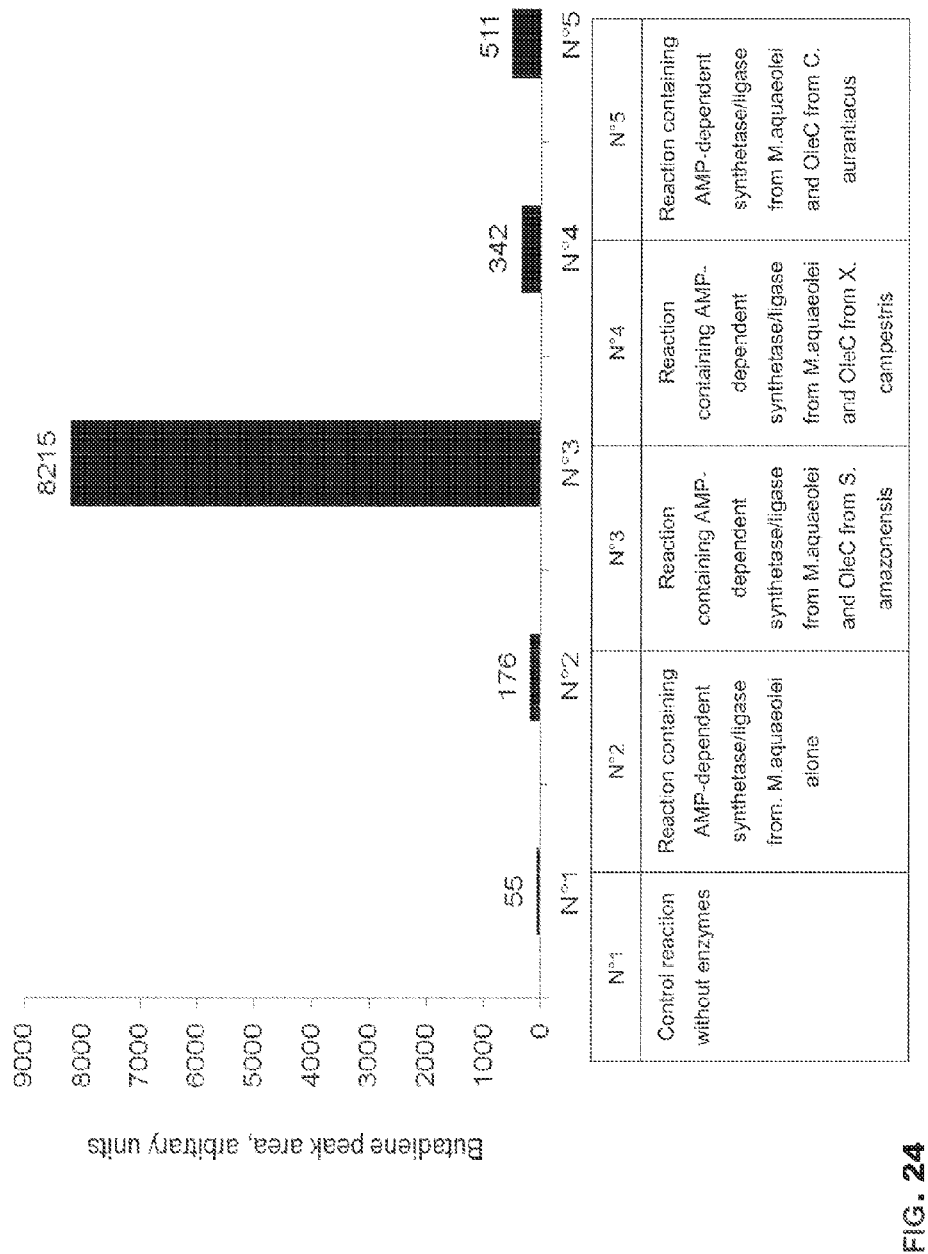

FIG. 24: shows enzyme-catalyzed 1,3-butadiene production from (R,S)-3-hydroxypent-4-enoate as outlined in Example 16.

Figure 25:
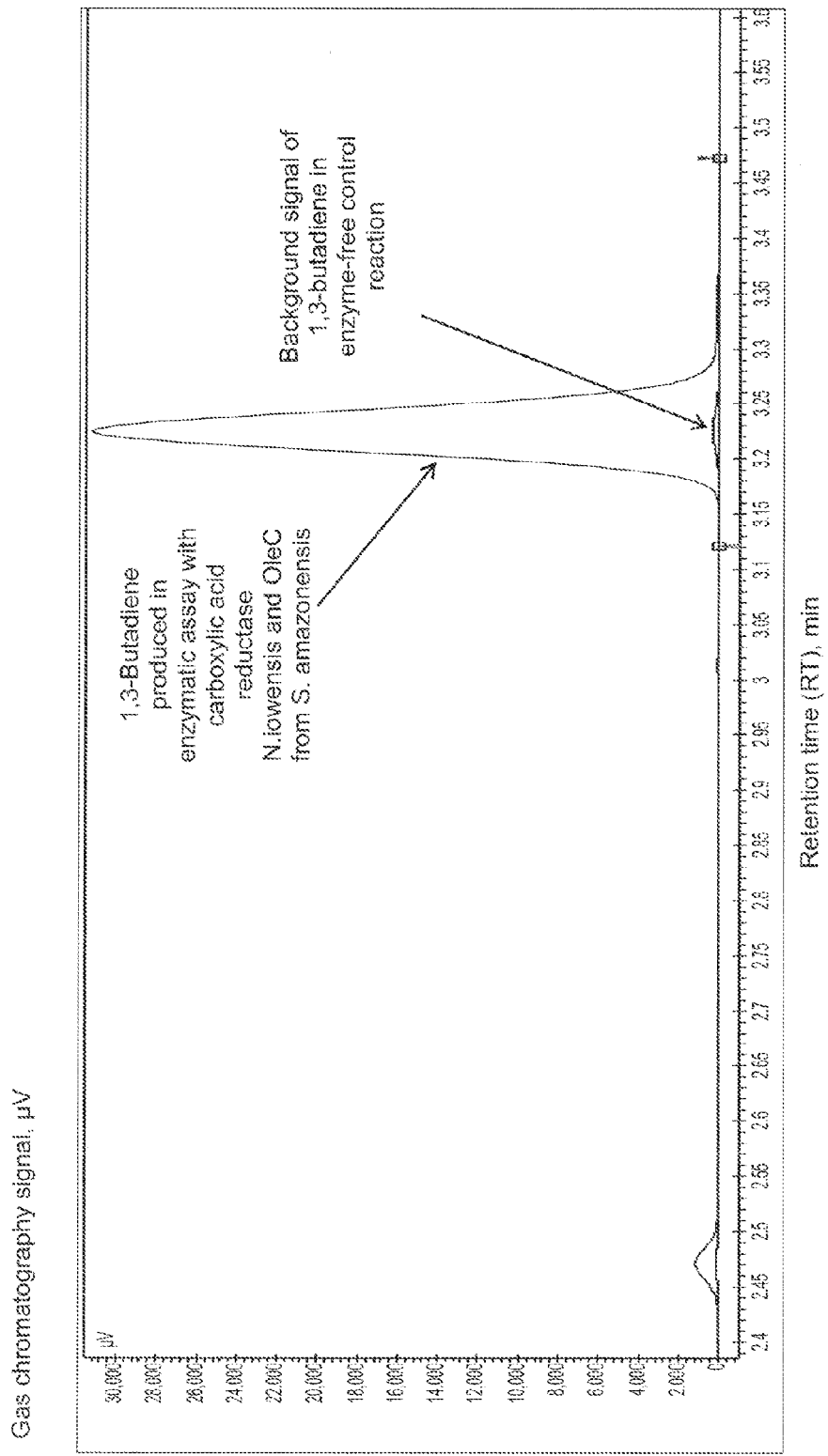

FIG. 25: shows GC/FID chromatograms obtained for enzymatic and enzyme-free reactions with (R,S)-3-hydroxypent-4-enoate as a substrate and ATP as a co-substrate.

Figure 26:
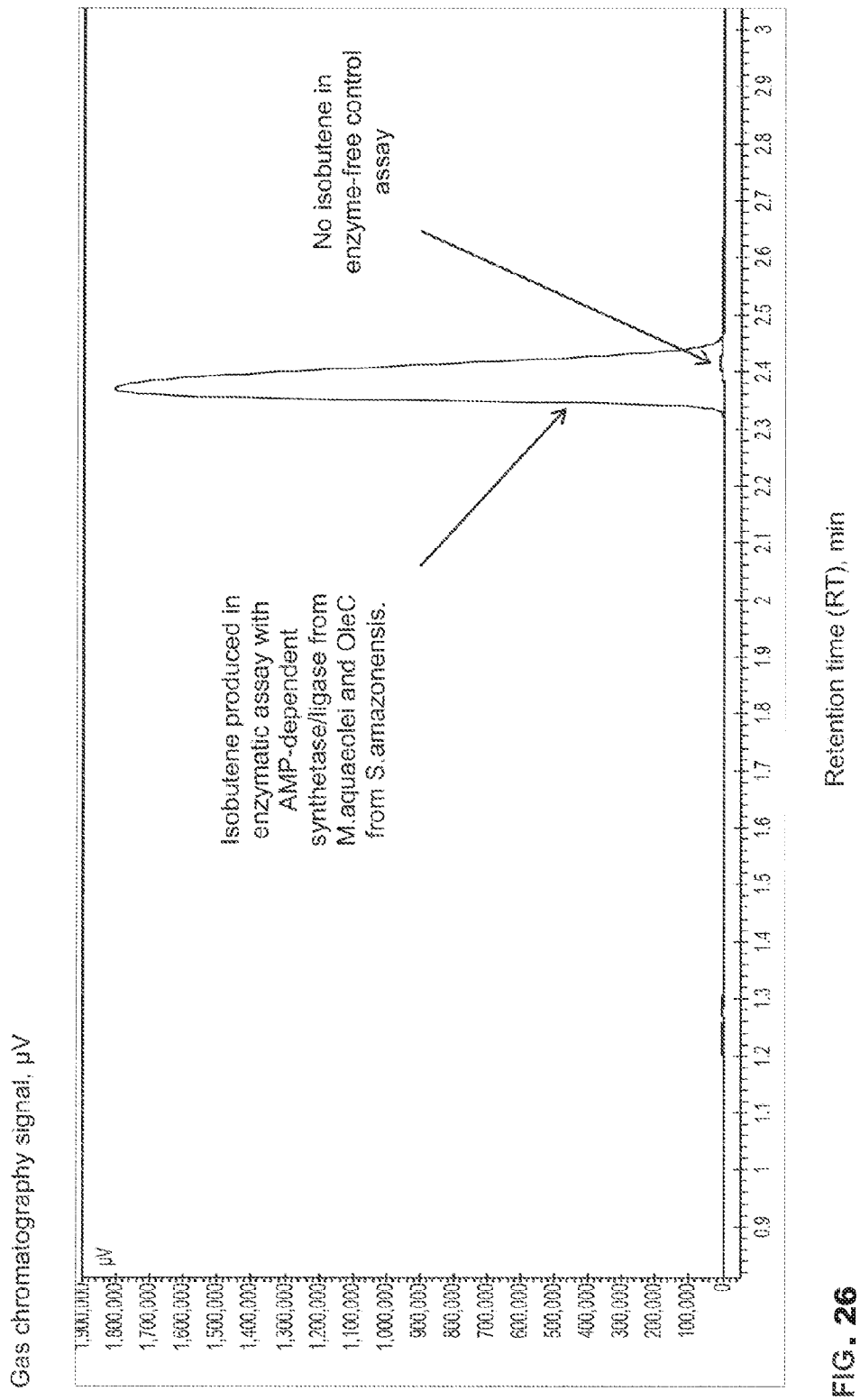

FIG. 26: shows GC/FID chromatograms obtained for enzymatic and enzyme-free reactions with 3-hydroxyisovalerate as a substrate and ATP as co-factor.

Figure 27:
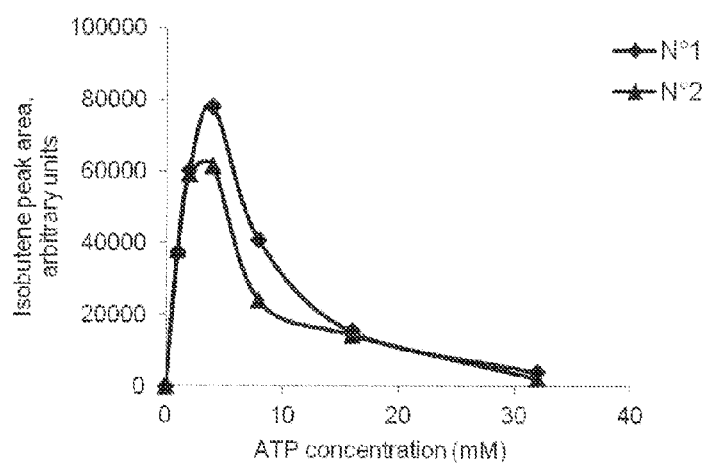

FIG. 27: shows a plot of isobutene formation from 3-hydroxyisovalerate as a function of ATP concentration. Reaction was catalyzed:

No 1: by AMP-dependent synthetase/ligase from *Burkholderia* sp. and OleC from *S. amazonensis*.

No 2: by AMP-dependent synthetase/ligase from *M. algicola* and OleC from *S. amazonensis*.

Figure 28:
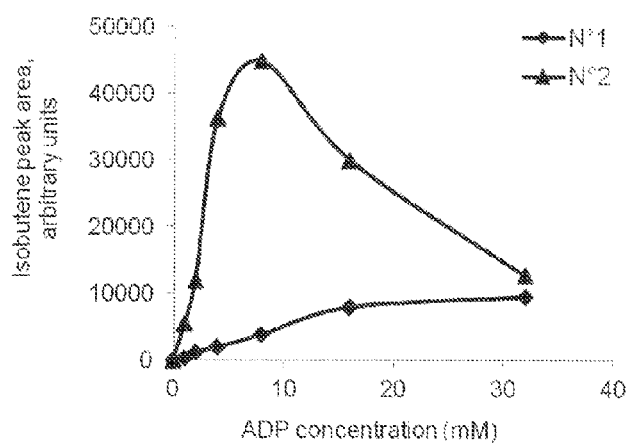

FIG. 28: shows a plot of isobutene formation from 3-hydroxyisovalerate as a function of ADP concentration. Reaction was catalyzed:

No 1: by AMP-dependent synthetase/ligase from *M. algicola* and OleC from *S. amazonensis*.

No 2: by AMP-dependent synthetase/ligase from *Burkholderia* sp. and OleC from *S. amazonensis*.

FIG. 29: shows the scheme of the reaction catalyzed by Ole ABCD (Wang and Lu, frontiers in Bioengineering an Biotechnology 1 (2013), Article 10).

It is to be understood that the present invention specifically relates to each and every combination of features and process parameters described herein, including any combination of general and/or preferred features/parameters. In particular, the invention specifically relates to all combinations of preferred features (including all degrees of preference) of the process provided herein.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1: Cloning, Expression and Purification of Enzymes

Gene Synthesis, Cloning and Expression of Recombinant Proteins

The sequences of the studied enzymes inferred from the genomes of prokaryotic and eukaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a pET-25b(+) expression vector (vectors were constructed by GeneArt®), except for *Nocardia iowensis* carboxylic acid reductase gene.

Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 37° C. and protein expression was continued at 28° C. or 18° C. overnight (approximately 16 h). The cells were collected by centrifugation at 4° C., 10,000 rpm for 20 min and the pellets were stored at −80° C.

The gene coding for the carboxylic acid reductase from *Nocardia iowensis* (Uniprot Q6RKB1) was codon-optimized by GeneArt® (Life Technologies). The gene construction provided by GeneArt® was flanked by PacI and NotI restriction sites and provided within master vector pMK. The gene thus synthesized was then subcloned into a modified version of pUC18 (New England Biolabs), containing a modified Multiple Cloning Site (MCS) (WO 2013/007786).

Competent MG1655 *E. coli* cells were transformed with this vector using standard heat shock procedure. The transformed cells were grown in LB-ampicillin medium for 24 h at 30° C., 160 rpm shaking.

The cells were collected by centrifugation at 4° C., 10,000 rpm for 20 min and the pellets were stored at −80° C.

Protein Purification and Concentration

The pellets from 200 ml of culture cells were thawed on ice and resuspended in 5 ml of 50 mM Tris-HCl buffer pH 7.5 containing 500 mM NaCl, 10 mM $MgCl_2$, 10% glycerol, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×30 seconds. The bacterial extracts were then clarified by centrifugation at 4° C., 10,000 rpm for 20 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 50 mM Tris-HCl buffer pH 7.5 containing 300 mM NaCl, 10% glycerol, 1 mM DTT, 250 mM imidazole. Eluates were then concentrated, desalted on Amicon Ultra-4 10 kDa filter unit (Millipore) and enzymes were resuspended in solution containing 50 mM Tris-HCl pH 7.5, containing 100 mM NaCl, 10% glycerol, 1 mM DTT. In the case of the OleC enzymes this resuspension buffer was supplemented with 1 mM AMP.

Protein concentrations were quantified by direct UV 280 nm measurement on the NanoDrop 1000 spectrophotometer (Thermo Scientific). The purity of proteins thus purified varied from 70% to 90% as estimated by SDS-PAGE analysis.

Example 2: Continuous Spectrophotometric Assay for Adenylation Enzyme Activity with 3-Hydroxypropionate as a Substrate and ATP as a Co-Substrate The genes coding for the adenylate-forming enzymes were synthesized and the corresponding enzymes were further produced according to the procedure described in Example 1. 3-hydroxypropionic acid (TCI) stock solution was prepared in water with the pH adjusted to 7.5 with 1 M NaOH. The release of diphosphate which is associated with 3-hydroxypropionyl-adenylate formation from 3-hydroxypropionate was quantified using the EnzCheck® Pyrophosphatase Assay Kit (E6645, Life Technologies).

In this assay, diphosphate was hydrolyzed to inorganic phosphate by inorganic pyrophosphatase and phosphate production coupled to phosphorolysis of the 2-amino-6-mercapto-7-methylpurine ribonucleoside (MESG), catalyzed by the enzyme purine nucleoside phosphorylase (PNP). The chromophoric product, 2-amino-6-mercapto-7-methylpurine, was monitored by absorbance at 360 nm (FIG. 9).

Standard reaction mixture contained:
100 mM Tris-HCl pH 7.5
5 mM 3-hydroxypropionate
2 mM $MgCl_2$
0.1 mM DTT
2 mM ATP
0.1 mg/ml of studied enzyme
2-amino-6-mercapto-7-methylpurine ribonucleoside (MESG), purine nucleoside phosphorylase (PNP) and inorganic pyrophosphatase were added to the reaction mix according to the procedure described in the EnzCheck® Pyrophosphatase Assay Kit. Control reactions were performed in which either no adenylate-forming enzyme was added, or no 3-hydroxypropionate was added. Each reaction was started by the addition of ATP. Reactions were performed in 96-well plates at 37° C.

Each sample was continuously monitored for the increase of 2-amino-6-mercapto-7-methylpurine at 360 nm on a SpectraMax Plus 384 UV/Vis Microplate Reader (Molecular Devices).

Several enzymes showed adenylation activity with 3-hydroxypropionate (FIG. 10).

Example 3: Continuous Spectrophotometric Assay for Adenylation Enzyme Activity with 3-Hydroxyvalerate as a Substrate and ATP as a Co-Substrate Spectrophotometric assay was performed according to the procedure described in Example 2. R-3-hydroxyvaleric acid was purchased from EMPA (Switzerland). R-3-hydroxyvaleric acid stock solution was prepared in water with the pH adjusted to 7.5 with 1 M NaOH. The composition of the reaction mixture was the same as that described in Example 2 using 5 mM R-3-hydroxyvalerate as a substrate instead of 3-hydroxypropionate. Control reactions were performed in which either no adenylate-forming enzyme was added, or no 3-hydroxyvalerate was added. Each reaction was started by the addition of ATP. Reactions were performed in 96-well plates at 37° C. Each sample was continuously monitored for the increase of 2-amino-6-mercapto-7-methylpurine at 360 nm on a SpectraMax Plus 384 UV/Vis Microplate Reader (Molecular Devices). Several enzymes demonstrated adenylation activity with 3-hydroxyvalerate (FIG. 11).

Example 4: Continuous Spectrophotometric Assay for Adenylation Enzyme Activity with 3-Hydroxypent-4-Enoate as a Substrate and ATP as a Co-Substrate Spectrophotometric assay was performed according to the procedure described in Example 2. (R,S)-3-hydroxypent-4-enoic acid (Epsilon Chimie) stock solution was prepared in water with the pH adjusted to 7.5 with 1 M NaOH. The composition of the reaction mixture was the same as that described in Example 2 using 5 mM (R,S)-3-hydroxypent-4-enoate as a substrate instead of 3-hydroxypropionate. Control reactions were performed in which either no adenylate-forming enzyme was added, or no 3-hydroxypent-4-enoate was added. Reactions were performed in 96-well plates at 37° C. Each sample was continuously monitored for the increase of 2-amino-6-mercapto-7-methylpurine at 360 nm on a SpectraMax Plus 384 UV/Vis Microplate Reader (Molecular Devices). Several enzymes demonstrated adenylation activity with 3-hydroxypent-4-enoate (FIG. 12).

Example 5: Continuous Spectrophotometric Assay for Adenylation Enzyme Activity with 3-Hydroxyisovalerate as a Substrate and ATP as a Co-Substrate Spectrophotometric assay was performed according to the procedure described in Example 2. 3-hydroxyisovaleric acid (3-hydroxy-3-methylbutyric acid) (TCI) stock solution was prepared in water with the pH adjusted to 7.5 with 1 M NaOH. The composition of the reaction mixture was the same as that described in Example 2 using 5 mM 3-hydroxyisovalerate as a substrate instead of 3-hydroxypropionate. Control reactions were performed in which either no adenylate-forming enzyme was added, or no 3-hydroxyisovalerate was added. Reactions were performed in 96-well plates at 37° C. Each sample was continuously monitored for the increase of 2-amino-6-mercapto-7-methylpurine at 360 nm on a SpectraMax Plus 384 UV/Vis Microplate Reader (Molecular Devices). Several enzymes demonstrated adenylation activity with 3-hydroxyisovalerate (FIG. 13).

Example 6: Continuous Spectrophotometric Assay for Adenylation Enzyme Activity with 3-Hydroxybutyrate as a Substrate and ATP as a Co-Substrate Spectrophotometric assay was performed according to the procedure described in Example 2. (R,S)-3-hydroxybutyric acid (Sigma-Aldrich) stock solution was prepared in water with the pH adjusted to 7.5 with 1 M NaOH. The composition of the reaction mixture was the same as that described in Example 2 using 5 mM (R,S)-3-hydroxybutyrate as a substrate instead of 3-hydroxypropionate. Control reactions were performed in which either no adenylate-forming enzyme was added, or no 3-hydroxybutyrate was added. Reactions were performed in 96-well plates at 37° C. Each sample was continuously monitored for the increase of 2-amino-6-mercapto-7-methylpurine at 360 nm on a SpectraMax Plus 384 UV/Vis Microplate Reader (Molecular Devices). Several enzymes demonstrated adenylation activity with 3-hydroxybutyrate (FIG. 14).

Example 7: Study of Adenylation of 3-Hydroxybutyrate with ATP or ADP as Co-Substrates Spectrophotometric assay was performed according to the procedure described in Example 2. The specificity of acyl-CoA synthase from *M. algicola* and AMP-dependent synthetase/ligase from *Burkholderia* sp. with respect to co-substrates was analyzed. Standard reaction contained:
  100 mM Tris-HCl pH 7.5
  5 mM (R,S)-3-hydroxybutyrate
  2 mM $MgCl_2$
  0.1 mM DTT
  0-3.2 mM ATP or ADP
  0.1 mg/ml of purified enzyme
  2-amino-6-mercapto-7-methylpurine ribonucleoside (MESG), purine nucleoside phosphorylase (PNP) and inorganic pyrophosphatase were added to the reaction mix according to the procedure described in the EnzCheck® Pyrophosphatase Assay Kit. A reaction mixture without inorganic pyrophosphatase was used for assays with ADP as co-substrate. Control assays were performed in which either no enzyme was added, or no 3-hydroxybutyrate was added. Each assay was started with the addition of co-substrate (ATP or ADP). Each sample was continuously monitored for the increase of 2-amino-6-mercapto-7-methylpurine at 360 nm on a SpectraMax Plus 384 UV/Vis Microplate Reader (Molecular Devices).

Plots of velocity of 2-amino-6-mercapto-7-methylpurine formation as a function of co-substrates concentration are shown on FIGS. 15 and 16. The acyl-CoA synthase from *M. algicola* and AMP-dependent synthetase/ligase from *Burkholderia* sp. were able to catalyze the formation of 3-hydroxybutyryl-adenylate by using ATP or ADP as co-substrate.

Example 8: Mass Spectrometry Analysis of the Enzyme-Catalyzed Adenylation Reaction of Different 3-Hydroxycarboxylates The studied enzymatic reactions were carried out under the following conditions:
  50 mM Tris-HCl pH 7.5
  2 mM 3-hydroxycarboxylate
  2 mM ATP
  20 mM $MgCl_2$
  100 mM NaCl
  1 mM DTT
  2 mg/ml purified AMP-dependant synthase/ligase from *Burkholderia* sp.

Each reaction was started by addition of ATP and incubated for 40 minutes at 37° C. Following incubation reactions mix were analyzed by mass spectrometry (MS) using negative ion mode. Typically, an aliquot of each assay was removed every 15 minutes, centrifuged and transferred into a clean vial. An aliquot of 5 µl was then directly injected into mass spectrometer. Detection was performed by a PE SCIEX API 2000 quadrupole spectrometer interfaced to an electrospray ionisation (ESI) source. Mass spectra of the enzymatic reactions using 3-hydroxybutyrate, 3-hydroxyvalerate, 3-hydroxyisovalerate and 3-hydroxypent-4-enoate as substrates are presented in FIGS. 17, 18, 19, 20, respectively. The formation of 3-hydroxycarboxyl-adenylate during the enzyme-catalyzed reaction were demonstrated for each of the studied 3-hydroxycarboxylate.

Example 9: Kinetic Parameters of the Reactions of Adenylation of 3-Hydroxycarboxylates Catalyzed by AMP-Dependent Synthetase/Ligase from *Marinobacter aquaeolei*

Kinetic parameters were determined by using the spectrophotometric assay described in Example 2. Reaction mixture for the assay of adenylation activity contained:
  100 mM Tris-HCl pH 7.5
  0-10 mM 3-hydroxycarboxylate
  2 mM ATP
  2 mM $MgCl_2$
  0.1 mM DTT
  0.1 mg/ml of purified AMP-dependent synthetase/ligase from *M. aquaeolei*
  2-amino-6-mercapto-7-methylpurine ribonucleoside (MESG), purine nucleoside phosphorylase (PNP) and inorganic pyrophosphatase were added to the reaction mix according to the procedure described in the EnzCheck® Pyrophosphatase Assay Kit. Kinetic parameters for adenylation reaction with different 3-hydroxycarboxylates are shown in Table 2.

TABLE 2

| Substrate | $K_M$, mM | $k_{cat}$ $10^{-3}$, $s^{-1}$ |
|---|---|---|
| 3-hydroxypropionate | 5 | 40 |
| (R,S)-3-hydroxybutyrate | 2 | 30 |
| 3-hydroxyisovalerate | 10 | 7 |
| R-3-hydroxyvalerate | 4 | 12 |
| (R,S)-3-hydroxypent-4-enoate | 3 | 23 |

Example 10: Analysis of Propylene Production from 3-Hydroxybutyrate by the Combined Action of AMP-Dependent Synthetase/Ligase from *Marinobacter aquaeolei* and OleC Proteins The studied enzymes were produced and purified according to the procedure described in Example 1. The studied reaction was carried out under the following conditions
  50 mM Tris-HCl pH 7.5
  50 mM (R,S)-3-hydroxybutyrate
  10 mM ATP
  20 mM $MgCl_2$
  100 mM NaCl
  1 mM DTT
  2 mg/ml purified AMP-dependent synthetase/ligase from *M. aquaeolei*
  2 mg/ml purified OleC protein from *Shewanella amazonensis* or from *Chloroflexus aurantiacus*
  Reaction volume was 0.3 ml.
  For the no enzymes control, buffer was used in place of enzymes.
  Controls reactions without ATP were realized in parallel.

The reaction mixtures were incubated in 2 ml sealed vials (Interchim) for 18 hours at 37° C. with shaking. Propylene production was analyzed by Gas Chromatography (GC) using Bruker 450-GC gas chromatograph equipped with Flame Ionization Detector (FID). Nitrogen was used as carrier gas with a flow rate of 6 ml/min. Volatile compounds were chromatographically separated on GS-Alumina column (30 m×0.53 mm ID) (Agilent) using an isothermal mode at 130° C. The enzymatic reaction product were identified by comparison with standard of propylene (Sigma-Aldrich), the retention time of propylene in these conditions was 1.57 min.

A significant production of propylene from 3-hydroxybutyrate was observed in enzymatic reactions contained AMP-dependent synthetase/ligase from *M. aquaeolei* and OleC protein (Table 3). No propylene signal was observed in controls reactions described above (FIG. 21).

TABLE 3

| Reaction | Propylene peak area, arbitrary units |
|---|---|
| Control reaction without enzymes | 0 |
| AMP-dependent synthetase/ligase from *M. aquaeolei* alone | 0 |
| AMP-dependent synthetase/ligase from *M. aquaeolei* + OleC protein from *S. amazonensis* | 50.8 |
| AMP-dependent synthetase/ligase from *M. aquaeolei* + OleC from *C. aurantiacus* | 3.4 |

These data indicated that the two enzymes present in the assay were performing complementarily the two steps of reaction to produce propylene from 3-hydroxybutyrate: transfer of the adenylyl group of ATP to the carboxyl group of 3-hydroxybutyrate followed by combined deadenylation/decarboxylation of the reaction intermediate into propylene.

Example 11: Analysis of Propylene Production from 3-Hydroxybutyrate by the Combined Action of Carboxylic Acid Reductase from *Nocardia iowensis* and OleC Protein from *Shewanella amazonensis*

The studied reaction was carried out under the following conditions
  50 mM Tris-HCl pH 7.5
  10 mM (R,S)-3-hydroxybutyrate
  2 mM ATP
  25 mM $MgCl_2$
  100 mM NaCl
  1 mM DTT
  2 mg/ml purified carboxylic acid reductase from *N. iowensis*
  2 mg/ml purified OleC protein from *S. amazonensis*
  Reaction volume was 0.3 ml.
  For the no enzymes control, buffer was used in place of enzymes.

The reactions were incubated in 2 ml sealed vials (Interchim) for 3 hours at 37° C. and then stopped by 1-minute incubation at 80° C. Propylene production was analyzed according to GC-FID procedure described in Example 10. A significant production of propylene from 3-hydroxybutyrate was observed in enzymatic reactions containing carboxylic acid reductase *N. iowensis* and OleC protein from *S. amazonensis*. Propylene peak area was measured to be 16.7 arbitrary units. No propylene signal was observed in the control reaction.

Example 12: Analysis of Propylene Production from 3-Hydroxybutyrate by the Combined Action of AMP-Dependent Synthetase/Ligase from *Burkholderia* sp and OleC Proteins from *Shewanella* Genus The studied reaction was carried out under the following conditions
  50 mM Tris-HCl pH 7.5
  10 mM (R,S)-3-hydroxybutyrate
  2 mM ATP
  25 mM $MgCl_2$
  100 mM NaCl
  1 mM DTT
  2 mg/ml purified AMP-dependent synthetase/ligase from *Burkholderia* sp.
  2 mg/ml purified OleC protein from *S. amazonensis* or *S. loihica*
  Reaction volume was 0.3 ml.

The reactions were incubated in 2 ml sealed vials (Interchim) for 3 hours at 37° C. and then stopped by 1-minute incubation at 80° C.

Propylene production was analyzed according to GC-FID procedure described in Example 10. A significant propylene production was observed in coupled enzyme reactions (FIG. 22).

Example 13: Analysis of 1-Butene Production from 3-Hydroxyvalerate by the Combined Action of AMP-Dependent Synthetase/Ligase from *Marinobacter aquaeolei* and the OleC Protein from *Shewanella amazonensis*

The studied reaction was carried out under the following conditions:

50 mM Tris-HCl pH 7.5

10 mM R-3-hydroxyvalerate 4 mM ATP 20 mM MgCl$_2$ 100 mM NaCl 1 mM DTT 2 mg/ml purified AMP-dependent synthetase and ligase from *M. aquaeolei*

2 mg/ml purified OleC protein from *S. amazonensis*

Reaction volume was 0.3 ml.

For the no enzymes control, buffer was used in place of enzymes.

The assays were incubated in 2 ml sealed vials (Interchim) for 16 hours at 37° C. with shaking.

1-Butene production was then analyzed by Gas Chromatography (GC) using Bruker 450-GC gas chromatograph equipped with Flame Ionization Detector (FID). Nitrogen was used as carrier gas with a flow rate of 6 ml/min. Volatile compounds were chromatographically separated on GS-Alumina column (30 m×0.53 mm ID) (Agilent) using an isothermal mode at 130° C. The enzymatic reaction product were identified by comparison with standard of 1-butene (Sigma-Aldrich), the retention time of 1-butene in these conditions was 2.65 min.

A significant production of 1-butene from 3-hydroxyvalerate was observed in the enzymatic reaction, containing the AMP-dependent synthetase/ligase from *M. aquaeolei* and the OleC protein from *S. amazonensis*. 1-Butene peak area was measured to be 32 arbitrary units. No 1-butene signal was observed in control reaction without enzyme.

These data indicated that the two enzymes present in the assay were performing complementarily the two steps of reaction to produce 1-butene from 3-hydroxyvalerate: transfer of the adenylyl group of ATP to the carboxyl group of 3-hydroxyvalerate followed by combined deadenylation/decarboxylation of the reaction intermediate into 1-butene.

Example 14: Analysis of 1-Butene Production from 3-Hydroxyvalerate by the Combined Action of Carboxylic Acid Reductase from *Nocardia iowensis* and OleC Protein from *Shewanella amazonensis*

The studied reaction was carried out under the following conditions:

50 mM Tris-HCl pH 7.5

10 mM R-3-hydroxyvalerate 2 mM ATP 25 mM MgCl$_2$ 100 mM NaCl 1 mM DTT 2 mg/ml purified carboxylic acid reductase from *N. iowensis*

2 mg/ml purified OleC protein from *S. amazonensis*

Reaction volume was 0.3 ml.

For the no enzymes control, buffer was used in place of enzymes.

The reactions were incubated in 2 ml sealed vials (Interchim) for 3 hour at 37° C. and then stopped by 1-minute incubation at 80° C.

1-Butene production was then analyzed according to GC-FID procedure described in Example 13. Chromatograms of enzyme-catalyzed reaction and control reaction are shown on FIG. 23.

Example 15: Analysis of 1-Butene Production from 3-Hydroxyvalerate by the Combined Action of AMP-Dependent Synthetase/Ligase from *Burkholderia* sp and OleC Proteins from *Shewanella Phylum*

The studied reaction was carried out under the following conditions 50 mM Tris-HCl pH 7.5

10 mM R-3-hydroxyvalerate 2 mM ATP 25 mM MgCl$_2$ 100 mM NaCl 1 mM DTT 2 mg/ml purified AMP-dependent synthetase/ligase from *Burkholderia* sp.

2 mg/ml purified OleC protein from *S. amazonensis* or *S. loihica*

Reaction volume was 0.3 ml. The assays were incubated as described in Example 14 and analyzed according to GC-FID procedure described in Example 13.

TABLE 4

| Reaction | 1-butene peak area, arbitrary units |
| --- | --- |
| Control reaction without enzymes | 1 |
| Reaction containing AMP-dependent synthetase/ligase from *Burkholderia* sp.and OleC from *S. amazonensis* | 50 |
| Reaction containing AMP-dependent synthetase/ligase from *Burkholderia* sp. and OleC from *S. loihica* | 51 |

Example 16: Analysis of 1,3-Butadiene Production from 3-Hydroxypent-4-Enoate by the Combined Action of AMP-Dependent Synthetase/Ligase from *Marinobacter aquaeolei* and OleC Proteins The studied reaction was carried out under the following conditions 50 mM Tris-HCl pH 7.5

50 mM (R,S)-3-hydroxypent-4-enoate 10 mM ATP 20 mM MgCl$_2$ 100 mM NaCl 1 mM DTT Reaction volume was 0.3 ml 0.6 mg of AMP-dependent synthetase/ligase from *M. aquaeolei* and 0.6 mg of OleC protein were added to 0.3 ml of reaction mixture. A reaction mix containing only 0.6 mg of AMP-dependent synthetase/ligase from *M. aquaeolei* was used as reference.

The reactions were incubated in 2 ml sealed vials (Interchim) for 18 hours at 37° C. with shaking. 1,3-butadiene production was analyzed by Gas Chromatography (GC) using Bruker 450-GC gas chromatograph equipped with Flame Ionization Detector (FID). Nitrogen was used as carrier gas with a flow rate of 6 ml/min. Volatile compounds were chromatographically separated on GS-Alumina column (30 m×0.53 mm ID) (Agilent) using an isothermal mode at 130° C. The enzymatic reaction product were identified by comparison with standard of 1,3-butadiene (Sigma-Aldrich), the retention time of 1,3-butadiene in these conditions was 3.22 min.

A significant production of 1,3-butadiene was observed in the enzymatic reactions, containing AMP-dependent synthetase/ligase from *M. aquaeolei* and OleC protein. A negligible signal of 1,3-butadiene corresponding to the spontaneous decomposition of 3-hydroxypent-4-enoate was observed in control reaction (FIG. 24).

These data indicated that the two enzymes present in the assay were performing complementarily the two steps of reaction to produce 1,3-butadiene from 3-hydroxypent-4-enoate: transfer of the adenylyl group of ATP to the carboxyl group of 3-hydroxypent-4-enoate followed by combined deadenylation/decarboxylation of the reaction intermediate into butadiene.

Example 17: Analysis of 1,3-Butadiene Production from 3-Hydroxypent-4-Enoate by Combining Carboxylic Acid Reductase from *Nocardia iowensis* and OleC Protein from *Shewanella amazonensis*

The studied reaction was carried out under the following conditions:
50 mM Tris-HCl pH 7.5
10 mM (R,S)-3-hydroxypent-4-enoate
2 mM ATP
25 mM MgCl$_2$
100 mM NaCl
1 mM DTT
2 mg/ml purified carboxylic acid reductase from *N. iowensis*
2 mg/ml purified OleC protein from *S. amazonensis*.
Reaction volume was 0.3 ml.

For the no enzymes control, buffer was used in place of enzymes. The reactions were incubated in 2 ml sealed vials (Interchim) for 3 hours at 37° C. and the reactions were stopped by 1-minute incubation at 80° C. 1,3-Butadiene production was analyzed according to GC-FID procedure described in Example 16. A significant quantity of butadiene was produced in the enzymatic reaction. A background level of butadiene was observed in the enzyme-free control reaction due to the spontaneous decomposition of 3-hydroxypent-4-enoate (FIG. 25).

Example 18: Analysis of 1,3-Butadiene Production from 3-Hydroxypent-4-Enoate by Combining Action of AMP-Dependent Synthetase/Ligase from *Burkholderia* Sp and OleC Proteins from *Shewanella Phylum*

The studied reaction was carried out under the following conditions
50 mM Tris-HCl pH 7.5
10 mM (R,S)-3-hydroxypent-4-enoate
2 mM ATP
25 mM MgCl$_2$
100 mM NaCl
1 mM DTT
2 mg/ml purified AMP-dependent synthetase/ligase from *Burkholderia* sp
2 mg/ml purified OleC protein from *S. amazonensis* or *S. loihica*
Reaction volume was 0.3 ml. The assays were incubated and analyzed according to the procedure described in Example 16. A significant production of 1,3-butadiene was observed in coupled enzymatic reactions, a negligible signal of butadiene was observed in control reaction without enzymes due to the spontaneous decomposition of 3-hydroxypent-4-enoate (Table 5).

TABLE 5

| Reaction | 1,3-butadiene peak area, arbitrary units |
| --- | --- |
| Control reaction without enzymes | 10 |
| Reaction containing AMP-dependent synthetase/ligase from *Burkholderia* sp. and OleC from *S. amazonensis* | 559 |
| Reaction containing AMP-dependent synthetase/ligase from *Burkholderia* sp.and OleC from *S. loihica* | 1550 |

Example 19: Analysis of Isobutene Production from 3-Hydroxyisovalerate by the Combined Action of AMP-Dependent Synthetase/Ligase from *Marinobacter aquaeolei* and OleC Proteins The studied reaction was carried out under the following conditions
50 mM Tris-HCl pH 7.5
50 mM 3-hydroxyisovalerate
10 mM ATP
20 mM MgCl$_2$
100 mM NaCl
1 mM DTT
Reaction volume was 0.3 ml 0.6 mg of AMP-dependent synthetase/ligase from *M. aquaeolei* and 0.6 mg of OleC protein were added to 0.3 ml of reaction mixture. A reaction mixture containing only 0.6 mg of AMP-dependent synthetase/ligase from *M. aquaeolei* was used as reference. The assays were incubated in 2 ml sealed vials (Interchim) for 18 hours at 37° C. with shaking. Isobutene production was analyzed by Gas Chromatography (GC) using Bruker 450-GC gas chromatograph equipped with Flame Ionization Detector (FID). Nitrogen was used as carrier gas with a flow rate of 6 ml/min. Volatile compounds were chromatographically separated on GS-Alumina column (30 m×0.53 mm ID) (Agilent) using an isothermal mode at 130° C. The enzymatic reaction product were identified by comparison with standard of isobutene (Sigma-Aldrich), the retention time of isobutene in these conditions was 2.40 min.

A significant production of Isobutene was observed in combined enzymatic reactions, contained the AMP-dependent synthetase/ligase from *M. aquaeolei* and OleC protein (Table 6). A negligible signal of isobutene corresponding to spontaneous decomposition of 3-hydroxyisovalerate was observed in control assay without enzyme.

TABLE 6

| Reaction | Isobutene peak area, arbitrary units |
| --- | --- |
| Control reaction without enzymes | 341 |
| Reaction containing AMP-dependent synthetase/ligase from. *M. aquaeolei* alone | 414 |
| Reaction containing AMP-dependent synthetase/ligase from *M. aquaeolei* and OleC from *S. amazonensis* | 113259 |
| Reaction containing AMP-dependent synthetase/ligase from *M. aquaeolei* and OleC from *C. aurantiacus* | 4824 |

TABLE 6-continued

| Reaction | Isobutene peak area, arbitrary units |
|---|---|
| Reaction containing AMP-dependent synthetase/ligase from *M. aquaeolei* and OleC from *S. maltophilia* | 1419 |

An example of chromatogram obtained for the coupled reaction with enzyme from *M. aquaeolei* and OleC protein from *S. amazonensis* is shown in FIG. 26.

These data indicated that the two enzymes present in the assay were performing complementarily the two steps of reaction to produce isobutene from 3-hydroxyisovalerate: transfer of the adenylyl group of ATP to the carboxyl group of 3-hydroxyisovalerate followed by combined deadenylation/decarboxylation of the reaction intermediate into isobutene.

Example 20: Study of Isobutene Production as a Function of ATP Concentration

The studied reaction was carried out under the following conditions
50 mM Tris-HCl pH 7.5
40 mM 3-hydroxyisovalerate
0-32 mM ATP
25 mM $MgCl_2$
100 mM NaCl
1 mM DTT
2 mg/ml purified adenylate-forming enzyme
2 mg/ml purified OleC protein from *S. amazonensis*

The reactions mix were incubated in 2 ml sealed vials (Interchim) for 3 hours at 37° C. and the reactions were stopped by 1-minute incubation at 80° C. The isobutene production as function of ATP is shown in FIG. 27.

Example 21: Study of Isobutene Production as a Function of ADP Concentration

The studied reactions were performed according to the protocol described in Example 20 using ADP as co-substrate instead of ATP. The isobutene production as function of ADP is shown in FIG. 28.

The invention claimed is:

1. A method for producing an alkene from a 3-hydroxycarboxylate wherein a 3-hydroxycarboxylate of the following general formula I:

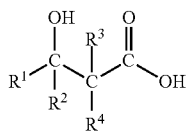

Formula I wherein $R^1$ and $R^3$ are independently selected from hydrogen (—H), methyl (—CH$_3$), ethyl (—CH$_2$—CH$_3$), isopropyl (—CH$_2$(CH$_3$)$_2$), vinyl (—CH═CH$_2$) and isopropenyl (—C(CH$_3$)═CH$_2$) and in which $R^2$ and $R^4$ are independently selected from hydrogen (—H) and methyl (—CH$_3$),
is, in a first step, enzymatically converted using an adenylate forming enzyme (EC 6.2.1) together with a co-substrate of the following formula II:

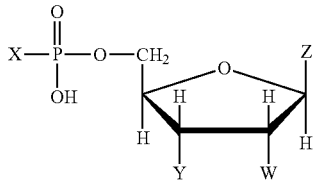

Formula II wherein X is selected from the group consisting of
O—PO$_3$H$_2$ monophosphate,
O—PO$_2$H—O—PO$_3$H$_2$ diphosphate, and
O—SO$_3$H sulfate,
and wherein Y is selected from the group consisting of
OH hydroxyl and
O—PO$_3$H$_2$ monophosphate,
and wherein Z is a nucleobase selected from the group consisting of adenine, guanine, thymine, cytosine, uracil and hypoxanthine,
and wherein W is selected from the group consisting of hydrogen (—H) hydroxyl (OH),
into a 3-hydroxycarboxyl-nucleotidylate of the following general formula III:

Formula III

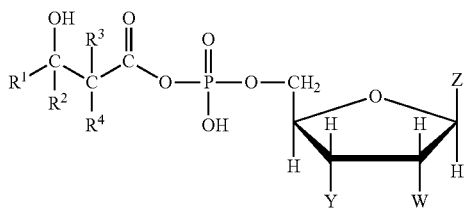

wherein $R^1$, $R^2$, $R^3$ and $R^4$ have the same meaning as specified above in connection with formula I and wherein W, Y and Z have the same meaning as specified above in connection with formula II,
and in that the thus produced 3-hydroxycarboxyl-nucleotidylate is subsequently enzymatically converted, using a recombinant OleC protein, into an alkene of the following general formula IV:

Formula IV

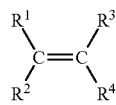

wherein $R^1$, $R^2$, $R^3$ and $R^4$ have the same meaning as specified above in connection with formula I.

2. The method of claim 1, wherein the adenylate forming enzyme is selected from the group consisting of:
an AMP-dependent synthetase and ligase
an adenylation domain of a non-ribosomal peptide synthetase (NRPS);
an acyl- or aryl-CoA synthetases; and
an adenylation domain of a polyketide synthase (PKS).

3. The method of claim 1, wherein the adenylate forming enzyme is selected from the group consisting of:
acetate:CoA ligase (AMP forming) (EC 6.2.1.1);
butanoate:CoA ligase (AMP forming) (EC 6.2.1.2);
long-chain fatty acid:CoA ligase (AMP-forming) (EC 6.2.1.3);
4-Coumarate-CoA ligase (EC 6.2.1.12);
long-chain-fatty-acid:[acyl-carrier protein] ligase (AMP-forming) (EC 6.2.1.20);
4-chlorobenzoate:CoA ligase (EC 6.2.1.33); and
3-hydroxypropionate:CoA ligase (AMP-forming) (EC 6.2.1.36).

4. The method of claim 1, wherein the method is carried out in vitro.

5. The method of claim 1, wherein the method is carried out in the presence of a microorganism producing the adenylated forming enzyme (EC 6.2.1).

6. The method according to claim 1, comprising a step of collecting the gaseous alkene degassing out of the reaction.

7. The method of claim 1, wherein the co-substrate is selected from ATP, UTP, CTP, GTP, ITP, ADP, CDP, GCP, UDP, IDP, dATP, dCTP, dGTP, dTTP, dITP, 3'-phosphoadenosin-5'-phosphosulfate (PAPS), or adenosin-5'-phosphosulfate (APS).

8. The method of claim 1, wherein the adenylate forming enzyme is a polypeptide comprising the amino acid sequence of SEQ ID NO:1.

9. The method of claim 1, wherein the adenylate forming enzyme is a polypeptide comprising the amino acid sequence of SEQ ID NO:1, SEQ ID NO:2, SEQ ID NO:3, SEQ ID NO:4 or SEQ ID NO:5.

10. The method of claim 1, wherein the OleC protein comprises the amino acid sequence of SEQ ID NO:8, SEQ ID NO:9, SEQ ID NO:10, SEQ ID NO:11, or SEQ ID NO:12.

11. The method of claim 5, wherein the microorganism is selected from bacteria, yeasts, fungi or mold.

12. The method of claim 11, wherein the microorganism is a thermophilic bacterium or an anaerobic bacterium.

13. The method of claim 12, wherein the bacterium is of the genus *Thermus, Thermoplasma*, or *Clostridiae*.

14. The method of claim 11, wherein the bacterium is *Escherichia coli, Alcaligenes eutrophus*, or *Bacillus megaterium*.

15. The method of claim 11, wherein the fungus is of the genus *Saccharomyces, Schizosaccharomyces, Aspergillus, Trichoderma, Pichia*, or *Kluyveromyces*.

* * * * *

UNITED STATES PATENT AND TRADEMARK OFFICE
CERTIFICATE OF CORRECTION

PATENT NO. : 10,017,787 B2
APPLICATION NO. : 15/101148
DATED : July 10, 2018
INVENTOR(S) : Maria Anissimova, Mathieu Allard and Philippe Marlière It is certified that error appears in the above-identified patent and that said Letters Patent is hereby corrected as shown below:

In the Claims

Column 86, Claim 5, Line 49, should read:
-- The method of claim 1, wherein the method is carried out in the presence of a microorganism producing the adenylated forming enzyme (EC 6.2.1) and the recombinant OleC protein. --

Signed and Sealed this
Twentieth Day of August, 2019

Andrei Iancu
*Director of the United States Patent and Trademark Office*